(12) United States Patent
Dai et al.

(10) Patent No.: US 11,369,584 B2
(45) Date of Patent: Jun. 28, 2022

(54) ANDROGRAPHOLIDE DERIVATIVES AND METHOD OF USING THE SAME FOR TREATMENT OR PREVENTION OF FIBROSIS

(71) Applicant: Zhengzhou University, Zhengzhou (CN)

(72) Inventors: Guifu Dai, Zhengzhou (CN); Haiwei Xu, Zhengzhou (CN); Zhenzhen Guan, Zhengzhou (CN); Yake Wang, Zhengzhou (CN); Di Wu, Zhengzhou (CN); Pengpeng Shen, Zhengzhou (CN); Ning Shang, Zhengzhou (CN); Fengjuan Wu, Zhengzhou (CN); Jin Zhao, Zhengzhou (CN); Xiaopei Zhang, Zhengzhou (CN)

(73) Assignee: ZHENGZHOU UNIVERSITY, Zhengzhou (CN)

( * ) Notice: Subject to any disclaimer, the term of this patent is extended or adjusted under 35 U.S.C. 154(b) by 73 days.

(21) Appl. No.: 16/589,101

(22) Filed: Sep. 30, 2019

(65) Prior Publication Data
US 2020/0030280 A1    Jan. 30, 2020

Related U.S. Application Data

(63) Continuation-in-part of application No. PCT/CN2018/080776, filed on Mar. 28, 2018.

(30) Foreign Application Priority Data

Apr. 1, 2017   (CN) .................. 201710214066.4
Mar. 2, 2018   (CN) .................. 201810174773.X
Mar. 2, 2018   (CN) .................. 201810174798.X

(51) Int. Cl.
| | | |
|---|---|---|
| *A61K 31/341* | (2006.01) | |
| *A61P 19/04* | (2006.01) | |
| *A61K 31/4025* | (2006.01) | |
| *A61K 31/443* | (2006.01) | |
| *C07D 307/60* | (2006.01) | |
| *A61K 31/365* | (2006.01) | |
| *C07D 405/12* | (2006.01) | |

(52) U.S. Cl.
CPC .......... *A61K 31/341* (2013.01); *A61K 31/365* (2013.01); *A61K 31/4025* (2013.01); *A61K 31/443* (2013.01); *A61P 19/04* (2018.01); *C07D 307/60* (2013.01); *C07D 405/12* (2013.01)

(58) Field of Classification Search
CPC ............... A61K 31/341; A61K 31/365; A61K 31/4025; A61K 31/443; C07D 307/60; C07D 405/12; A61P 19/04; A61P 1/16
USPC ........................................ 549/295; 514/461
See application file for complete search history.

(56) References Cited

PUBLICATIONS

Reddy et al. Phytochemistry 2003, 62, 1271-1275. (Year: 2003).*

* cited by examiner

*Primary Examiner* — Taylor V Oh
(74) *Attorney, Agent, or Firm* — Matthias Scholl P.C.; Matthias Scholl

(57) ABSTRACT

A method of treatment or prevention of fibrosis of human tissue or organ. The method includes administering a patient in need thereof a compound of formula (I).

12 Claims, 47 Drawing Sheets

ANDROGRAPHOLIDE DERIVATIVES AND METHOD OF USING THE SAME FOR TREATMENT OR PREVENTION OF FIBROSIS

CROSS-REFERENCE TO RELATED APPLICATIONS

This application is a continuation-in-part of International Patent Application No. PCT/CN2018/080776 with an international filing date of Mar. 28, 2018, designating the United States, now pending, and further claims foreign priority benefits to Chinese Patent Application No. 201710214066.4 filed Apr. 1, 2017, Chinese Patent Application No. 201810174798.X filed Mar. 2, 2018, and Chinese Patent Application No. 201810174773.X filed Mar. 2, 2018. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to an andrographolide derivative and a method of using the same for treatment or prevention of fibrosis, and more particularly to a 15-methylene-14-deoxy-11,12-dehydro-andrographolide derivative.

Fibrosis is characterized by the excess accumulation of extracellular matrix components, leading to disrupted tissue function in affected organs. Fibrosis can develop in nearly every part of the body, and is an important driver of end-stage organ failure and death in a variety of chronic diseases.

Andrographolide is a labdane diterpenoid that has been isolated from the stem and leaves of *Andrographis paniculata*. Andrographolide has been studied for its effects on cell signaling, immunomodulation, and stroke, and can be used for anti-bacteria and anti-inflammatory. Till now, there is no reports about 15-methylene-14-deoxy-11,12-dehydro-andrographolide derivatives as an active ingredient for treatment or prevention of fibrosis.

SUMMARY

The disclosure provides a 15-methylene-14-deoxy-11,12-dehydro-andrographolide derivative and its applications for treatment or prevention of fibrosis.

The disclosure provides a 15-methylene-14-deoxy-11,12-dehydro-andrographolide derivative represented by Formula (I):

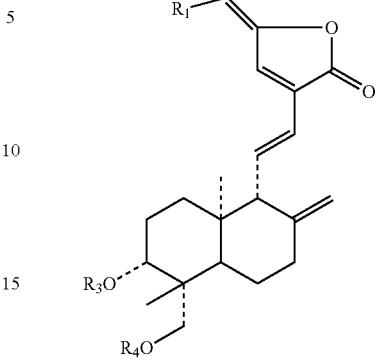

where $R_1$, $R_2$ independently, at each occurrence, represent H or a $C_{1-5}$ alkyl; or $R_1$, $R_2$ independently, at each occurrence, represent H, a phenyl, 2-methoxyphenyl, 3-methoxyphenyl, 4-methoxyphenyl, 2,3,5-trimethoxyphenyl, 2-hydroxyphenyl, 3-hydroxyphenyl, 4-hydroxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromophenyl, 3-fluoro-4-bromophenyl, 3-chloro-4-bromophenyl, 2,3,4-trichlorophenyl, 2-methoxy-4-chlorophenyl, 2-hydroxy-4-chlorophenyl, 2-hydroxy-4-methoxyphenyl, 3-amino-4-chlorophenyl, 2-amino-4-chlorophenyl, 2-nitro-4-fluorophenyl, 2-nitro-4-chlorophenyl, a $C_{1-5}$ alkyl substituted phenyl, a halogen and morpholinyl substituted phenyl, a halogen and methylpiperidine substituted phenyl, or N,N-dialkylaminophenyl; or pyridyl, furyl, thienyl, pyrrolyl, indoyl or halogen-substituted pyridyl, furyl, thienyl, pyrrolyl, indoyl; or benzofuranyl, benzimidazolyl, benzothiopyranyl, benzothiazolyl, benzotetrazolyl, benzisoxazolyl, benzisothiazolyl, benzimidazolyl, benzopyrazolyl, benzotriazolyl, benzothienyl, or benzoxazolyl; or $R_1$ and $R_2$ are taken together to form a cyclohexyl; $R_1$ and $R_2$ are the same or different, but do not synchronously represent H; $R_3$ and $R_4$ both represent H; or $R_3$ and $R_4$ independently, at each occurrence, represent a methylsulfonyl, a triphenylmethyl, or a 3-pyridyl; or $R_3$ and $R_4$ independently, at each occurrence, represent $CH_2CH_2COOH$, $CH_2CH_2CH_2CH_2COOH$, $CH_2CH_2CH_2CH_2CH_2COOH$, or $CH_2CH_2CH_2CH_2CH_2CH_2CH_2COOH$; or $R_3$ and $R_4$ both represent $COR_5$, and $R_5$ is a 3-pyridyl, $CH_2CH_2COOH$, $CH_2CH_2CH_2CH_2COOH$, $CH_2CH_2CH_2CH_2CH_2COOH$, or $CH_2CH_2CH_2CH_2CH_2CH_2CH_2COOH$, where $R_3$ and $R_4$ can be the same or different substituent groups.

When one of $R_1$ and $R_2$ is H, the other can be selected from a methyl, ethyl or propyl, phenyl, 2-methoxyphenyl, 3-methoxyphenyl, 4-methoxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4- dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4 dibromophenyl, 2-chloro-4-fluorophenyl, 2-bromo-4-fluorophenyl, 3-chloro-4-fluorobenzene, 3-bromo-4-fluorophenyl, 2-fluoro-4-bromophenyl, 2-chloro-4-bromophenyl, 3-fluoro-4-bromophenyl, 3-chloro-4-bromophenyl, 2-methoxy-4-chlorophenyl, 4-n-propylphenyl, 4-isopropylphenyl, 4-isobutylphenyl, 4-(N,N-dimethylamino)phenyl, 3-fluoro-4-(4-morpholinyl)phenyl, 3-fluoro-4-(4-methylpiperazinyl)phenyl, 2-furyl, 2-pyrrolyl, 6-chloro-3-indolyl, 3-indolyl, 5-chloro-3-indolyl, 6-chloro-2-pyridyl, 3-pyridyl; or $R_1$ and $R_2$ are taken together to form a cyclohexyl; $R_3$ and $R_4$ both represent H; or $R_3$ and $R_4$ independently, at each occurrence, represent $CH_2CH_2COOH$, $CH_2CH_2CH_2CH_2COOH$, $CH_2CH_2CH_2CH_2CH_2COOH$, or $CH_2CH_2CH_2CH_2CH_2CH_2COOH$; or $R_3$ and $R_4$ both represent $COR_5$, and $R_5$ is a 3-pyridyl or $CH_2CH_2COOH$, where $R_3$ and $R_4$ are the same or different substituent group.

When one of $R_1$ and $R_2$ is H, the other can be selected from a phenyl, 2-methoxyphenyl, 3-methoxyphenyl, 4-methoxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4 dibromophenyl, 2-chloro-4-fluorophenyl, 2-bromo-4-fluorophenyl, 3-chloro-4-fluorobenzene, 3-bromo-4-fluorophenyl, 2-fluoro-4-bromophenyl, 2-chloro-4-bromophenyl, 3-fluoro-4-bromophenyl, 3-chloro-4-bromobenzene Base, 2-methoxy-4-chlorophenyl; $R_3$ and $R_4$ both represent H; or $R_3$ and $R_4$ independently, at each occurrence, represent $CH_2CH_2COOH$, $CH_2CH_2CH_2CH_2COOH$, $CH_2CH_2CH_2CH_2CH_2COOH$, or $CH_2CH_2CH_2CH_2CH_2CH_2COOH$; or $R_3$ and $R_4$ both represent $COR_5$, and $R_5$ is $CH_2CH_2COOH$, where $R_3$ and $R_4$ are the same substituent group.

When one of $R_1$ and $R_2$ is H, the other can be selected from a methyl, an ethyl, a propyl, 2-furyl, 2-pyrrolyl, 6-chloro-3-indolyl, 3-indolyl, 5-chloro-3-indolyl, 6-chloro-2-pyridyl, 3-pyridyl, 4-n-propylphenyl, 4-isopropylphenyl, 4-isobutylphenyl, 3-fluoro-4-(4-methylpiperazinyl)phenyl, or $R_1$ and $R_2$ are taken together to form a cyclohexyl group, $R_3$ and $R_4$ both represent H.

The compound can be:
A: $R_1$=H, $R_2$=$C_6H_5$, $R_3$=$R_4$=H;
B: $R_1$=H, $R_2$=2-F—$C_6H_4$, $R_3$=$R_4$=H;
C: $R_1$=H, $R_2$=2-Cl—$C_6H_4$, $R_3$=$R_4$=H;
D: $R_1$=H, $R_2$=2-Br—$C_6H_4$, $R_3$=$R_4$=H;
E: $R_1$=H, $R_2$=3-F—$C_6H_4$, $R_3$=$R_4$=H;
F: $R_1$=H, $R_2$=3-Cl—$C_6H_4$, $R_3$=$R_4$=H;
G: $R_1$=H, $R_2$=3-Br—$C_6H_4$, $R_3$=$R_4$=H;
H: $R_1$=H, $R_2$=4-Cl—$C_6H_4$, $R_3$=$R_4$=H;
I: $R_1$=H, $R_2$=4-F—$C_6H_4$, $R_3$=$R_4$=H;
J: $R_1$=H, $R_2$=4-Br—$C_6H_4$, $R_3$=$R_4$=H;
K: $R_1$=H, $R_2$=4-$CH_3O$—$C_6H_4$, $R_3$=$R_4$=H;
L: $R_1$=H, $R_2$=2-$CH_3O$-4-Cl—$C_6H_3$, $R_3$=$R_4$=H;
M: $R_2$=H, $R_1$=2-Br—$C_6H_4$, $R_3$=$R_4$=H;
N: $R_2$=H, $R_1$=3-Cl—$C_6H_4$, $R_3$=$R_4$=H;
O: $R_2$=H, $R_1$=2-F-4-Cl—$C_6H_3$, $R_3$=$R_4$=H;
P: $R_2$=H, $R_1$=2, 4-diCl—$C_6H_3$, $R_3$=$R_4$=H;
Q: $R_2$=H, $R_1$=4-F—$C_6H_4$, $R_3$=$R_4$=H;
R: $R_2$=H, $R_1$=$C_6H_5$, $R_3$=$R_4$=H;
S: $R_1$=H, $R_2$=3-F-4-Cl—$C_6H_3$, $R_3$=$R_4$=H;
T: $R_1$=H, $R_2$=2, 4-diF—$C_6H_3$, $R_3$=$R_4$=H;
U: $R_1$=H, $R_2$=3, 4-diCl—$C_6H_3$, $R_3$=$R_4$=H;
V: $R_1$=H, $R_2$=4-Cl—$C_6H_4$, $R_3$=$R_4$=$COR_5$, $R_5$=3-pyridyl;
W: $R_1$=H, $R_2$=4-Cl—$C_6H_4$, $R_3$=$R_4$=$CH_2CH_2COOH$;
X: $R_1$=H, $R_2$=4-Cl—$C_6H_4$, $R_3$=$R_4$=$COR_5$, $R_5$=$CH_2CH_2COOH$;
Y: $R_2$=H, $R_1$=4-Cl—$C_6H_4$, $R_3$=$R_4$=H;
Z: $R_2$=H, $R_1$=4-Cl—$C_6H_4$, $R_3$=$R_4$=$COR_5$, $R_5$=3-pyridyl.

a. $R_1$=$CH_3$, $R_2$=$CH_3$, $R_3$=$R_4$=H;
b. 15-cyclohexylidene-14-deoxy-11,12-dehydro-andrographolide; $R_3$=$R_4$=H;
c. $R_1$=H, $R_2$=3-F-4-(4-methylpiperazine group)-$C_6H_3$, $R_3$=$R_4$=H;
d. $R_1$=H, $R_2$=

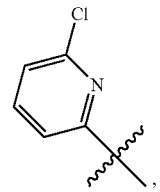 [SMILES: *c1cccc(Cl)n1]

$R_3$=$R_4$=H;
e. $R_1$=H, $R_2$=

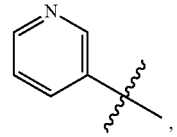 [SMILES: *c1cccnc1]

$R_3$=$R_4$=H;
f. $R_1$=H, $R_2$=

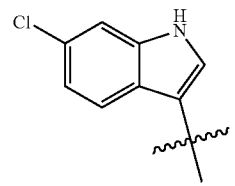

$R_3$=$R_4$=H;
g. $R_1$=H, $R_2$=

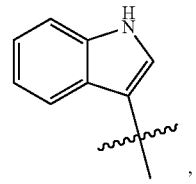 [SMILES: *c1c[nH]c2ccccc12]

$R_3$=$R_4$=H;
h. $R_1$=H, $R_2$=

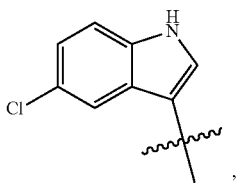 [SMILES: *c1c[nH]c2ccc(Cl)cc12]

$R_3=R_4=H$;
i. $R_1=H$, $R_2=$

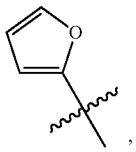 [SMILES: *c1ccco1]

$R_3=R_4=H$;
j. $R_1=H$, $R_2=$

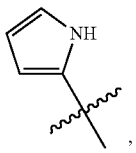 [SMILES: *c1ccc[nH]1]

$R_3=R_4=H$;
k. $R_1=H$, $R_2=$

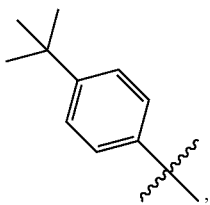 [SMILES: *c1ccc(C(C)(C)C)cc1]

$R_3=R_4=H$.

The compounds a-k are characterized as follows:

a: $C_{23}H_{32}O_4$; $^1$H NMR (400 MHz, DMSO-d6) δ 7.98 (s, 1H), 6.52 (dd, J=15.7, 10.6 Hz, 1H), 6.21 (d, J=15.7 Hz, 1H), 5.50 (s, 1H), 5.12 (s, 1H), 4.30 (s, 1H), 3.94 (d, J=10.9 Hz, 1H), 3.40 (d, J=10.9 Hz, 1H), 3.23 (dd, J=10.9, 4.1 Hz, 1H), 2.48 (d, J=10.8 Hz, 1H), 2.01 (s, 2H), 1.95 (s, 3H), 1.94 (s, 3H) 1.68-1.48 (m, 3H), 1.46 (s, 3H), 1.26 (dd, J=10.6, 6.2 Hz, 1H), 1.17 (br, 1H), 1.08 (s, 3H), 0.80 (s, 3H). $^{13}$C NMR (100 MHz, DMSO-d6) δ 169.06, 144.93, 137.67, 132.91, 132.57, 126.13, 123.18, 122.65, 122.32, 79.37, 62.99, 60.16, 49.98, 42.11, 38.28, 36.11, 27.82, 23.71, 23.22, 22.68, 18.84, 18.80, 15.99. HRMS (ESI): m/z calcd for $C_{23}H_{32}NaO_4$ [M+Na]$^+$, 395.2198; found, 395.2196.

b: $C_{26}H_{36}O_4$, $^1$H NMR (400 MHz, DMSO-d6) δ 8.02 (s, 1H), 6.52 (dd, J=15.7, 10.6 Hz, 1H), 6.21 (d, J=15.7 Hz, 1H), 5.50 (s, 1H), 5.12 (s, 1H), 4.30 (s, 1H), 3.94 (d, J=10.9 Hz, 1H), 3.40 (d, J=11.1 Hz, 1H), 3.22 (dd, J=10.9, 4.1 Hz, 1H), 2.48 (d, J=11.0 Hz, 1H), 2.45-2.36 (m, 4H), 2.01 (s, 2H), 1.59 (s, 6H), 1.57-1.47 (m, 3H), 1.46 (s, 3H), 1.26 (dd, J=10.6, 6.3 Hz, 1H), 1.17 (br, 1H), 1.08 (s, 3H), 0.79 (s, 3H). $^{13}$C NMR (100 MHz, DMSO-d6) δ 169.15, 142.54, 137.70, 132.59, 132.57, 130.84, 126.33, 122.65, 122.33, 79.37, 62.99, 60.16, 49.97, 42.11, 38.28, 36.11, 28.94, 28.72, 28.16, 27.82, 27.49, 26.08, 23.71, 23.22, 22.67, 15.99. HRMS (ESI): m/z calcd for $C_{26}H_{36}NaO_4$ [M+Na]$^+$, 435.2511; found, 435.2516.

c: $C_{32}H_{41}FN_2O_4$; $^1$H NMR (400 MHz, DMSO-d6) δ 7.69 (s, 1H), 7.52 (dd, J=14.9, 1.7 Hz, 1H), 7.46 (dd, J=8.6, 1.5 Hz, 1H), 7.06 (t, J=9.0 Hz, 1H), 6.58 (dd, J=15.7, 10.6 Hz, 1H), 6.29 (d, J=15.7 Hz, 1H), 6.26 (s, 1H), 5.50 (s, 1H), 5.12 (d, J=4.9 Hz, 1H), 4.31 (d, J=5.0 Hz, 1H), 3.94 (d, J=9.5 Hz, 1H), 3.45-3.39 (m, 1H), 3.22 (dd, J=10.4, 4.9 Hz, 1H), 3.14-3.06 (m, 4H), 2.51 (s, 1H), 2.49-2.44 (m, 4H), 2.22 (s, 3H), 2.01 (s, 2H), 1.64-1.49 (m, 3H), 1.47 (s, 3H), 1.25 (dd, J=10.5, 6.3 Hz, 1H), 1.22-1.13 (m, 1H), 1.08 (s, 3H), 0.80 (s, 3H). $^{13}$C NMR (100 MHz, DMSO-d6) δ 168.93, 154.54 (d, J=243 Hz), 147.10, 140.65 (d, J=9 Hz), 138.68, 137.17, 132.47, 127.89 (d, J=2 Hz), 127.33 (d, J=8 Hz), 125.61, 122.75, 122.28, 119.53, 119.49, 117.58, 117.36, 112.47 (d, J=2 Hz), 79.37, 62.99, 60.24, 54.94, 49.95, 49.91, 46.20, 42.12, 38.31, 36.21, 27.82, 23.71, 23.22, 22.70, 16.02. HRMS (ESI): m/z calcd for $C_{32}H_{42}FN_2O_4$ [M+H]$^+$, 537.3129; found, 537.3129.

d: $C_{26}H_{30}ClNO_4$; $^1$H NMR (400 MHz, DMSO) δ 7.96 (d, J=1.6 Hz, 1H), 7.95 (s, 1H), 7.82 (s, 1H), 7.48-7.42 (m, 1H), 6.89 (dd, J=15.8, 10.2 Hz, 1H), 6.33 (d, J=15.8, 10.2 Hz, 1H), 6.31 (d, J=16.8 Hz, 1H), 5.05 (d, J=4.5 Hz, 1H), 4.76 (s, 1H), 4.44 (s, 1H), 4.14 (d, J=4.9 Hz, 1H), 3.85 (d, J=10.8 Hz, 1H), 3.32-3.27 (m, 1H), 3.27-3.20 (m, 1H), 2.47 (d, J=10.1 Hz, 1H), 2.38 (d, J=13.6 Hz, 1H), 1.99 (dd, J=12.9, 8.4 Hz, 1H), 1.74 (d, J=13.2 Hz, 1H), 1.61 (dd, J=25.5, 7.3 Hz, 2H), 1.49-1.30 (m, 2H), 1.24-1.14 (m, 2H), 1.10 (s, 3H), 0.80 (s, 3H). $^{13}$C NMR (101 MHz, DMSO) δ 168.00, 152.75, 150.45, 148.71, 140.47, 136.64, 128.01, 124.09, 110.84, 78.59, 62.64, 60.74, 53.68, 42.39, 36.22, 27.63, 23.15, 23.00, 15.46.

e: $C_{26}H_{31}NO_4$; $^1$H NMR (400 MHz, DMSO) δ 8.83 (s, 1H), 8.52 (d, J=3.6 Hz, 1H), 8.18-8.164 (m, 1H), 7.79 (s, 1H), 7.48 (m, 4.8 Hz, 1H), 6.87 (dd, J=16.7, 9.2 Hz, 1H), 6.39 (s, 1H), 6.27 (d, J=16.6 Hz, 1H), 5.05 (s, 1H), 4.76 (s, 1H), 4.45 (s, 1H), 4.15 (dd, J=7.4, 2.6 Hz, 1H), 3.85 (dd, J=10.9, 2.6 Hz, 1H), δ 3.26 (m, 2H), 2.44 (d, J=11.9 Hz, 1H), 2.38 (d, 12 Hz, 1H), 1.99 (t, J=11.0 Hz, 1H), 1.74 (d, J=13.4 Hz, 1H), 1.58-1.60 (m, 2H), 1.45-1.3 (m, 2H), 1.23-1.18 (overlap, 1H), 1.10 (s, 3H), 0.80 (s, 3H).

f: $C_{29}H_{32}ClNO_4$; $^1$H NMR (400 MHz, DMSO) δ 11.89 (s, 1H), 7.95 (s, 1H), 7.90 (d, J=8.5 Hz, 1H), 7.69 (s, 1H), 7.52 (d, J=1.8 Hz, 1H), 7.17 (dd, J=8.5, 1.9 Hz, 1H), 6.77 (dd, J=15.7, 10.1 Hz, 1H), 6.70 (s, 1H), 6.25 (d, J=15.7 Hz, 1H), 5.03 (d, J=4.7 Hz, 1H), 4.75 (s, 1H), 4.46 (s, 1H), 4.14 (d, J=4.6 Hz, 1H), 3.86 (d, J=11.1 Hz, 1H), δ 3.29-3.18 (m, 2H), 2.40 (t, J=11.5 Hz, 2H), 1.99 (t, J=10.9 Hz, 1H), 1.74 (d, J=13.4 Hz, 1H), 1.66-1.52 (m, 2H), 1.50-1.30 (m, 2H), 1.18 (dd, J=19.8, 7.6 Hz, 2H). 1.11 (s, 3H), 0.79 (s, 3H).

g: $C_{29}H_{33}NO_4$; $^1$H NMR (400 MHz, DMSO) δ 11.84 (s, 1H), 7.94 (s, 1H), 7.89 (d, J=7.6 Hz, 1H), 7.68 (s, 1H), 7.48 (d, J=7.8 Hz, 1H), 7.18 (ddd, J=14.8, 13.8, 6.6 Hz, 2H), 6.82-6.74 (m, 1H), 6.71 (s, 1H), 6.24 (d, J=15.7 Hz, 1H), 5.04 (s, 1H), 4.75 (s, 1H), 4.47 (s, 1H), 4.15 (s, 1H), 3.88 (d, J=10.9 Hz, 1H), δ 3.33-3.20 (m, 2H), 2.43-2.33 (m, 2H), 1.99 (dd, J=13.0, 8.4 Hz, 1H), 1.72 (t, J=13.5 Hz, 1H), 1.60 (dd, J=15.2, 10.3 Hz, 2H), 1.49-1.31 (m, 2H), 1.17 (dd, J=18.2, 8.9 Hz, 2H). 1.11 (s, 3H), 0.79 (s, 3H). $^{13}$C NMR (101 MHz, DMSO) δ 168.67, 148.99, 144.24, 136.22, 136.04, 134.45, 129.52, 126.20, 123.10, 122.45, 121.83, 120.42, 118.59, 112.17, 109.69, 106.98, 78.66, 62.69, 60.86, 53.78, 42.37, 36.26, 27.68, 23.16, 22.99, 15.48.

h: $C_{29}H_{32}ClNO_4$ $^1$H NMR (400 MHz, DMSO) δ 11.96 (s, 1H), 8.00 (d, J=1.9 Hz, 1H), 7.98 (s, 1H), 7.66 (s, 1H), 7.48 (d, J=8.6 Hz, 1H), 7.20 (dd, J=8.6, 2.0 Hz, 1H), 6.83-6.76

(m, 1H), 6.74 (s, 1H), 6.25 (d, J=15.7 Hz, 1H), 5.03 (s, 1H), 4.75 (s, 1H), 4.47 (s, 1H), 4.13 (s, 1H), 3.87 (d, J=10.9 Hz, 1H), δ 3.27 (d, J=18.7 Hz, 2H), 2.39 (t, J=10.1 Hz, 2H), 2.00 (t, J=10.7 Hz, 1H), 1.74 (d, J=12.9 Hz, 1H), 1.60 (dd, J=15.6, 10.5 Hz, 2H), 1.41 (m, J=17.2, 13.2, 9.4 Hz, 2H), 1.17 (m, J=20.4, 7.6 Hz, 2H). 1.11 (s, 3H), 0.79 (s, 3H). $^{13}$C NMR (101 MHz, DMSO) δ 168.58, 148.97, 144.44, 136.15, 134.80, 134.54, 130.85, 127.37, 125.13, 123.54, 122.39, 121.77, 118.27, 113.74, 109.51, 108.15, 106.41, 78.65, 62.67, 60.88, 53.77.

i: $C_{25}H_{30}O_5$; $^1$H NMR (400 MHz, DMSO) δ 7.87 (d, J=1.3 Hz, 1H), 7.70 (s, 1H), 6.93-6.88 (m, 1H), 6.85-6.77 (m, 1H), 6.69-6.66 (m, 1H), 6.39 (s, 1H), 6.29 (dd, J=23.3, 15.8 Hz, 1H), 5.04 (d, J=4.9 Hz, 1H), 4.75 (s, 1H), 4.44 (s, 1H), 4.14 (dd, J=7.4, 2.8 Hz, 1H), 3.85 (dd, J=10.9, 2.6 Hz, 1H), δ 3.31-3.18 (m, 2H), 2.41 (dd, J=21.6, 11.7 Hz, 2H), 1.98 (d, J=11.6 Hz, 1H), 1.73 (d, J=12.9 Hz, 1H), 1.66-1.52 (m, 2H), 1.44 (m, J=14.0, 10.3 Hz, 1H), 1.35 (br, 1H), 1.17 (br, 2H). 1.10 (s, 3H), 0.79 (s, 2H). $^{13}$C NMR (101 MHz, DMSO) δ 168.25, 148.97, 148.82, 146.56, 145.42, 145.21, 136.76, 135.80, 128.34, 126.00, 121.44, 114.86, 113.19, 101.15, 78.60, 62.65, 60.76, 53.71, 42.38, 36.23, 27.63, 26.31, 23.16, 22.99, 15.45.

j: $C_{25}H_{31}NO_4$; $^1$H NMR (400 MHz, DMSO) δ 11.17 (s, 1H), 7.69 (s, 1H), 7.10-6.97 (m, 1H), 6.73 (dd, J=15.8, 10.1 Hz, 1H), 6.64 (s, 1H), 6.25 (s, 1H), 6.22 (dd, J=14.2, 9.1 Hz, 2H), 5.03 (d, J=4.8 Hz, 1H), 4.75 (s, 1H), 4.45 (s, 1H), 4.13 (dd, J=7.3, 2.5 Hz, 1H), 3.86 (dd, J=10.9, 2.1 Hz, 1H), δ 3.25 (m, 2H), 2.39 (t, J=11.8 Hz, 2H), 1.99 (dd, J=13.1, 8.5 Hz, 1H), 1.73 (d, J=13.0 Hz, 1H), 1.59 (dd, J=15.4, 10.3 Hz, 2H), 1.50-1.28 (m, 2H), 1.25-1.12 (m, 2H). 1.10 (s, 3H), 0.78 (s, 3H). $^{13}$C NMR (101 MHz, DMSO) δ 168.58, 148.98, 143.12, 136.08, 134.72, 126.18, 123.37, 123.25, 121.66, 114.79, 110.78, 108.14, 104.83, 78.64, 62.67, 60.80, 53.76, 48.57, 42.38, 36.25, 27.65, 23.16, 23.00, 15.47.

k: $C_{31}H_{40}O_4$; s$^1$H NMR (400 MHz, DMSO) δ 7.73 (s, 1H), 7.68 (d, J=8.5 Hz, 2H), 7.48 (d, J=8.5 Hz, 2H), 6.83 (dd, J=15.8, 10.1 Hz, 1H), 6.31 (s, 1H), 6.26 (d, J=15.8 Hz, 1H), 5.05 (d, J=4.4 Hz, 1H), 4.75 (s, 1H), 4.45 (s, 1H), 4.14 (d, J=5.2 Hz, 1H), 3.86 (d, J=10.8 Hz, 1H), δ 3.31-3.18 (m, 2H), 2.41 (dd, J=20.9, 11.9 Hz, 2H), 1.99 (t, J=10.6 Hz, 1H), 1.71 (t, J=16.9 Hz, 1H), 1.67-1.51 (m, 2H), 1.49-1.31 (m, 2H), 1.29 (s, 9H), 1.24-1.13 (m, 2H), 1.10 (s, 3H), 0.79 (s, 3H).

To study the application effect of the compounds for treatment or prevention of fibrosis, hepatic stellate cells LX-2, as a material, are used to determine the inhibitory effect of the compound of the disclosure on cell migration and activation, evaluating the anti-fibrotic activity of the compounds; furthermore, a SD rat model of $CCl_4$-induced liver fibrosis, a Wistar rat model of pig serum-induced liver fibrosis and a SD rat model of bile duct ligation (BDL)-induced liver fibrosis are used as representatives, the anti-liver fibrosis activity of the compounds was evaluated by measuring the collagen content of the liver tissue (Masson's trichrome staining) and the expression level of the HSC activation marker molecule α-SMA. Further, through the $CCl_4$ model, systematic studies have demonstrated the main relevant roles and mechanisms of representative compounds that play a role in anti-fibrosis. The anti-pulmonary fibrosis activity of the compounds was evaluated by using the human alveolar type II cell A549 to study the inhibitory activity of the compound of the disclosure on TGF-β1-induced A549 cells to mesenchymal cells transition. A rat model of bleomycin-induced pulmonary fibrosis was further used to study the in vivo anti-pulmonary fibrosis effect of the compound. The inhibitory activity of the compounds of the disclosure on TGF-beta1-induced HK-2 cell to mesenchymal cell transition was evaluated using proximal renal tubular epithelial cell HK-2, and the anti-renal fibrosis activity of the compounds was evaluated. Unilateral Ureteral Obstruction (UUO) rat model was further used to study the anti-renal fibrosis activity of the compound of the disclosure. After stimulation of primary cardiac fibroblast HCFB with AngII, the anti-myocardial fibrosis effect of the compounds of the disclosure was evaluated based on the detection of cell proliferation rate.

The cis- and trans-isomers of the compounds have anti-fibrotic activity. Using the compounds as effective pharmaceutical ingredients, or various prodrugs of the compounds, or alone or in combination with other drugs, according to various conventional pharmaceutical methods and process requirements, and after mixing with acceptable and/or added ingredients in pharmaceuticals to form various anti-fibrotic pharmaceutical dosages such as an oral preparation and an injection preparation. Preferably, the medicament is prepared for treating or preventing various types of fibrotic diseases such as liver, lung, kidney, and heart. The oral preparation is a tablet, a pill, a capsule, a granule or a syrup; the injection preparation includes an injection or a freeze-dried powder injection.

The above compounds can fight against the fibrosis of organ and/or tissue. The experiment proves that the compounds of the disclosure can improve anti-liver, anti-lung, anti-kidney and/or anti-myocardial fibrosis compared to the parent compound, andrographolide (AD). Therefore, the use of the compounds for treatment or prevention of fibrosis provides a new concept for the treatment and prevention of diseases associated with fibrosis.

DETAILED DESCRIPTION

Figure 1A:
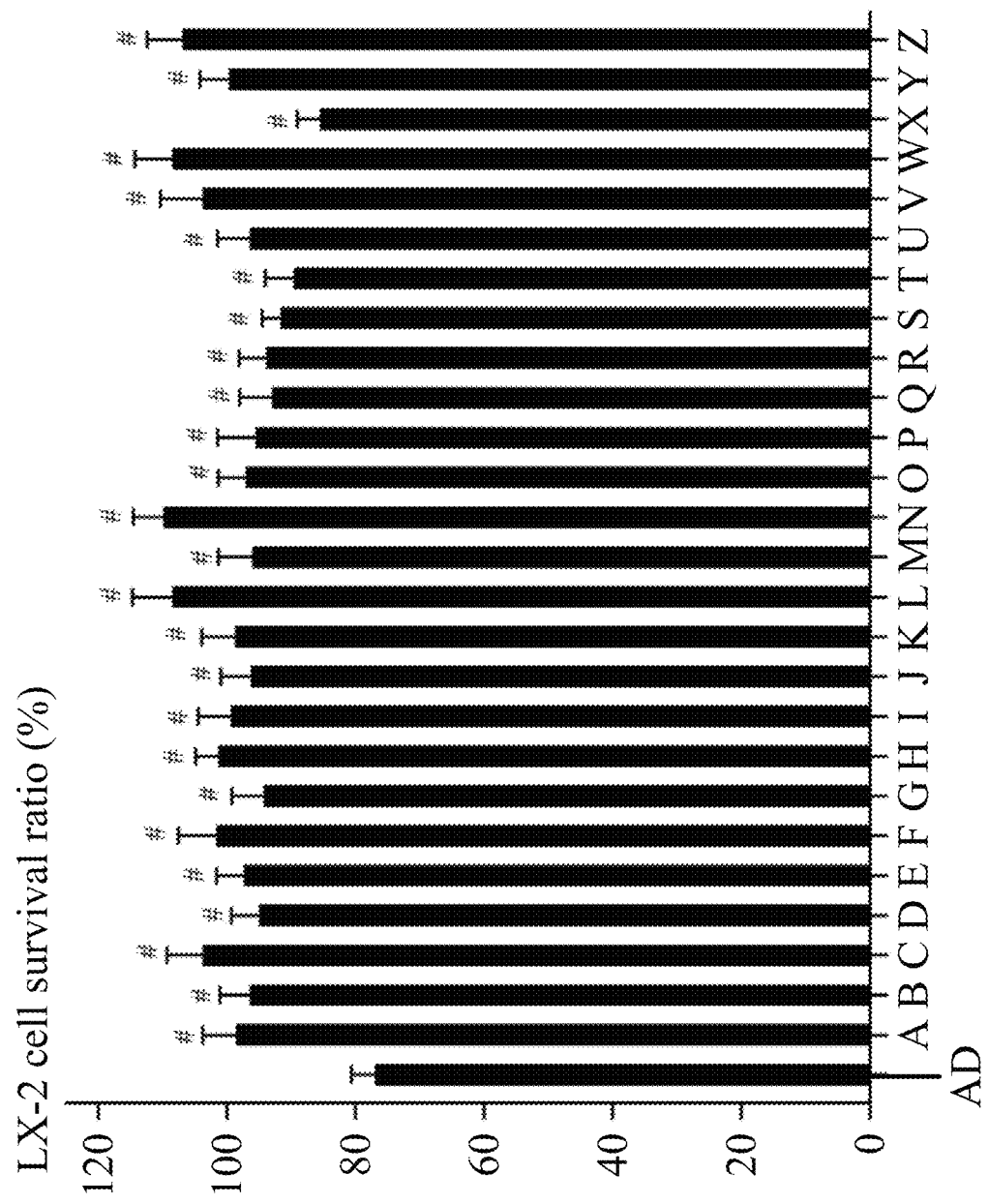
FIG. 1A shows the effect of AD and the representative compounds (15.00 μM) of the disclosure on the activity of human hepatic stellate cells LX-2; compared with the AD group, $^\#$P<0.05.

The invention is illustrated below in conjunction with specific embodiments. It is to be understood that these embodiments are only illustrative of the disclosure and are not intended to limit the scope of the disclosure. The compound is not limited to the representative structure used in the embodiments. For example, a different substituent at the 15-position can be replaced to obtain a compound having anti-fibrotic activity; or various factors inducing fibrosis are used as research objects to demonstrate that the compounds of the disclosure have anti-fibrotic effects; or other in vitro and in vivo research methods (models) are utilized to demonstrate that the compounds of the disclosure have an anti-fibrotic effect.

Example 1

The Compounds of the Disclosure Inhibit LX-2 Migration in Human Hepatic Stellate Cells Hepatic stellate cells migrate to the inflammatory site of damaged liver tissue under the stimulation of various inflammatory mediators and growth factors, and further proliferate and activate, in which the synthesis of ECM components such as collagen is crucial to the development of liver fibrosis. The effect of the compound fighting against liver fibrosis are evaluated by a scratch test method.

1. Cell Culture and Drug Treatment

The human hepatic stellate cell LX-2 (provided by Beijing Beina Chuanglian Biotechnology Institute) was used to compared with andrographolide (AD) to determine the in vitro anti-fibrosis effect of the compounds of the disclosure. LX-2 cells were cultured in RPMI1640 medium containing 10% (V/V) fetal bovine serum, 100 μg/mL streptomycin, and 100 IU/mL penicillin, and then were incubated in an incubator at 37° C. and 5% $CO_2$, humidified atmosphere.

2. MTT Assay for Assessment of Cytotoxicity

LX-2 cells in logarithmic growth phase were digested with 0.25% (w/v) trypsin, and diluted into $3.5\times10^5$/mL cell suspension with RPMI1640 medium containing 10% (v/v) fetal bovine serum. After each 96-well plate was filled with 200 μL cell suspension per well, the plates were placed in an incubator at 37° C. and 5% $CO_2$ for 24 h. The medium containing different concentrations of the drug was added, and the final concentration of the drug was up to 30.00 μM, and each treatment was repeated in 4 wells. Following 48 h of incubation, each plate was added with 20 μL MTT (5 mg/mL) per well and incubated for 4 h. After the supernatant was discard, 150 μL DMSO was added and shaken for 10 min. Absorbance at 570 nm was measured and reference absorbance was at 450 nm. The cell survival ratio in each well after compound treatment was calculated, and the survival ratio (%)=A value of treatment group/A value of cell control group×100%, and the results were shown in FIGS. 1A and 1B. Data were processed and analyzed using SPSS 17.0 statistical software. Data were expressed as mean±standard deviation ($\bar{X}\pm S$); There were significant differences between groups when P<0.05.

3. Scratch Test Method to Observe the Effect of Drugs on the Migration of LX-2 Cells.

Figure 2A:
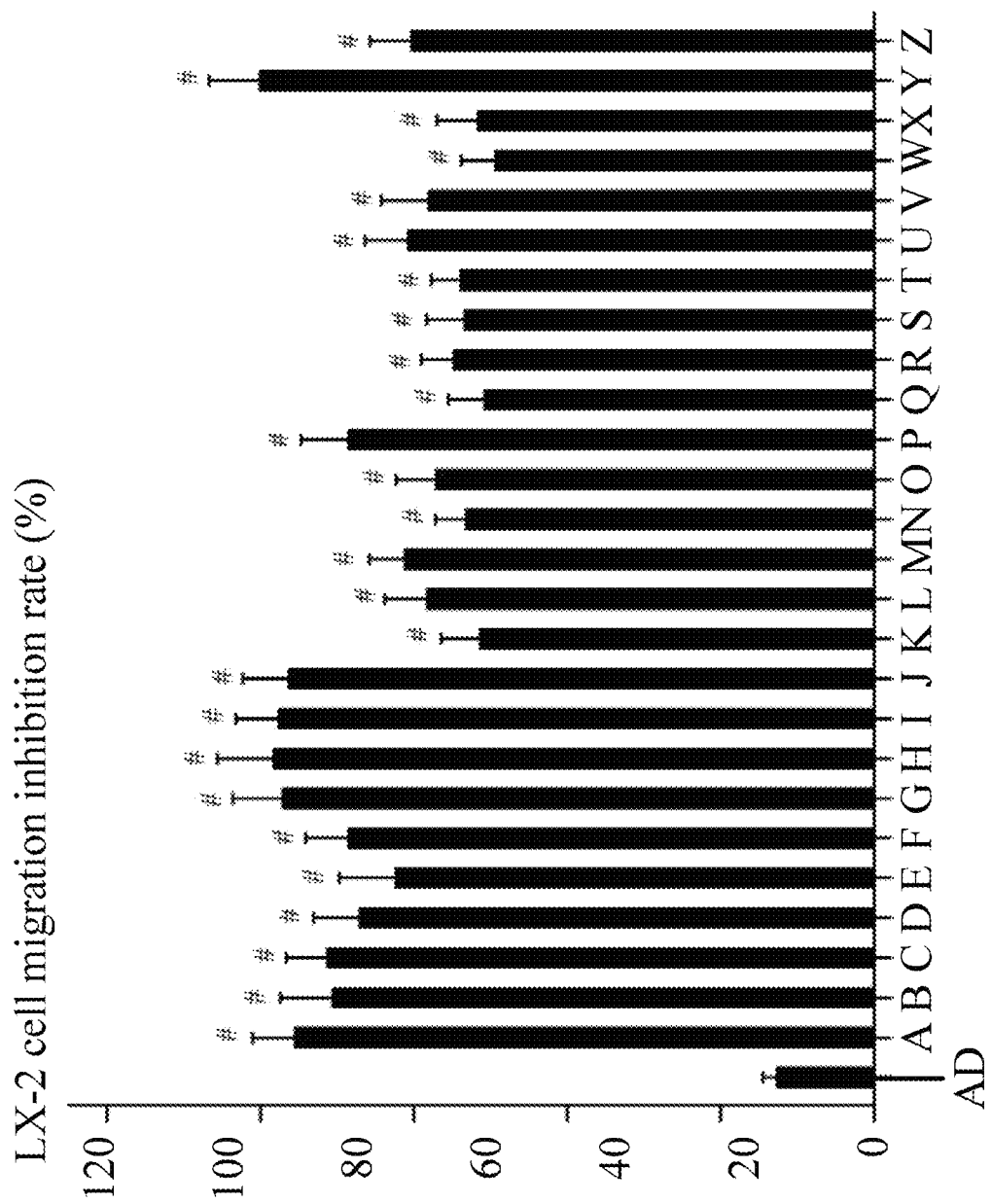
FIG. 2A shows the results (statistical results) of inhibition of human hepatic stellate cells LX-2 migration by using AD and the representative compounds of the disclosure (5.00 μM); compared with the AD group, $^\#$P<0.05.
Figure 2B:
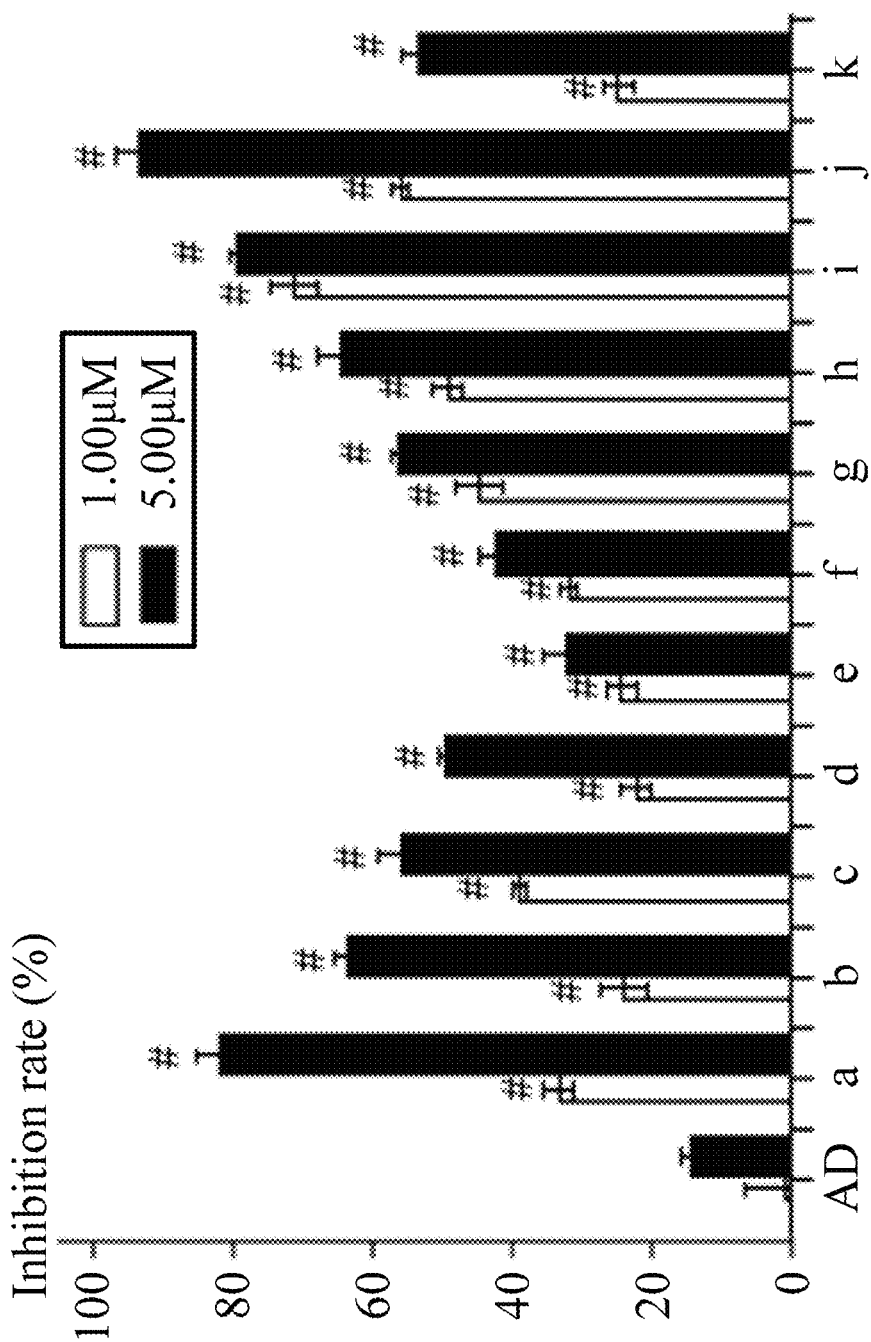
FIG. 2B shows the results (statistical results) of inhibition of human hepatic stellate cells LX-2 migration by using AD and the representative compounds of the disclosure (1.00 μM and 5.00 μM); compared with the AD group, $^\#$P<0.05.
Figure 3:
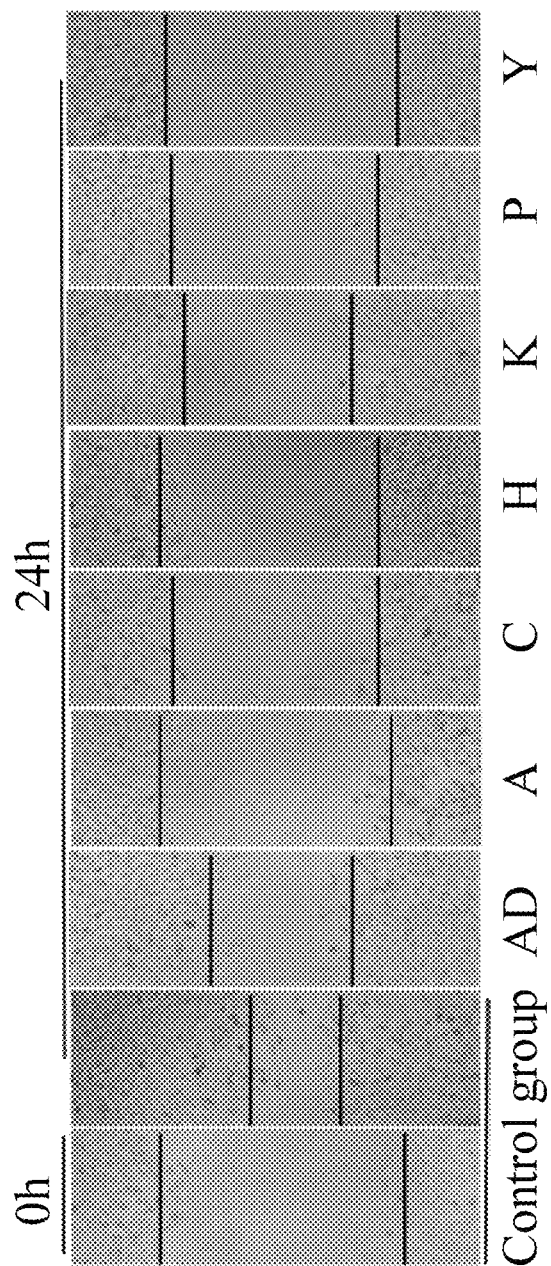
FIG. 3 is a graph showing the inhibition of human hepatic stellate cells LX-2 migration by using AD and the representative compounds of the disclosure (5.00 μM) (partial photomicrograph; ×100 times)
Figure 4:
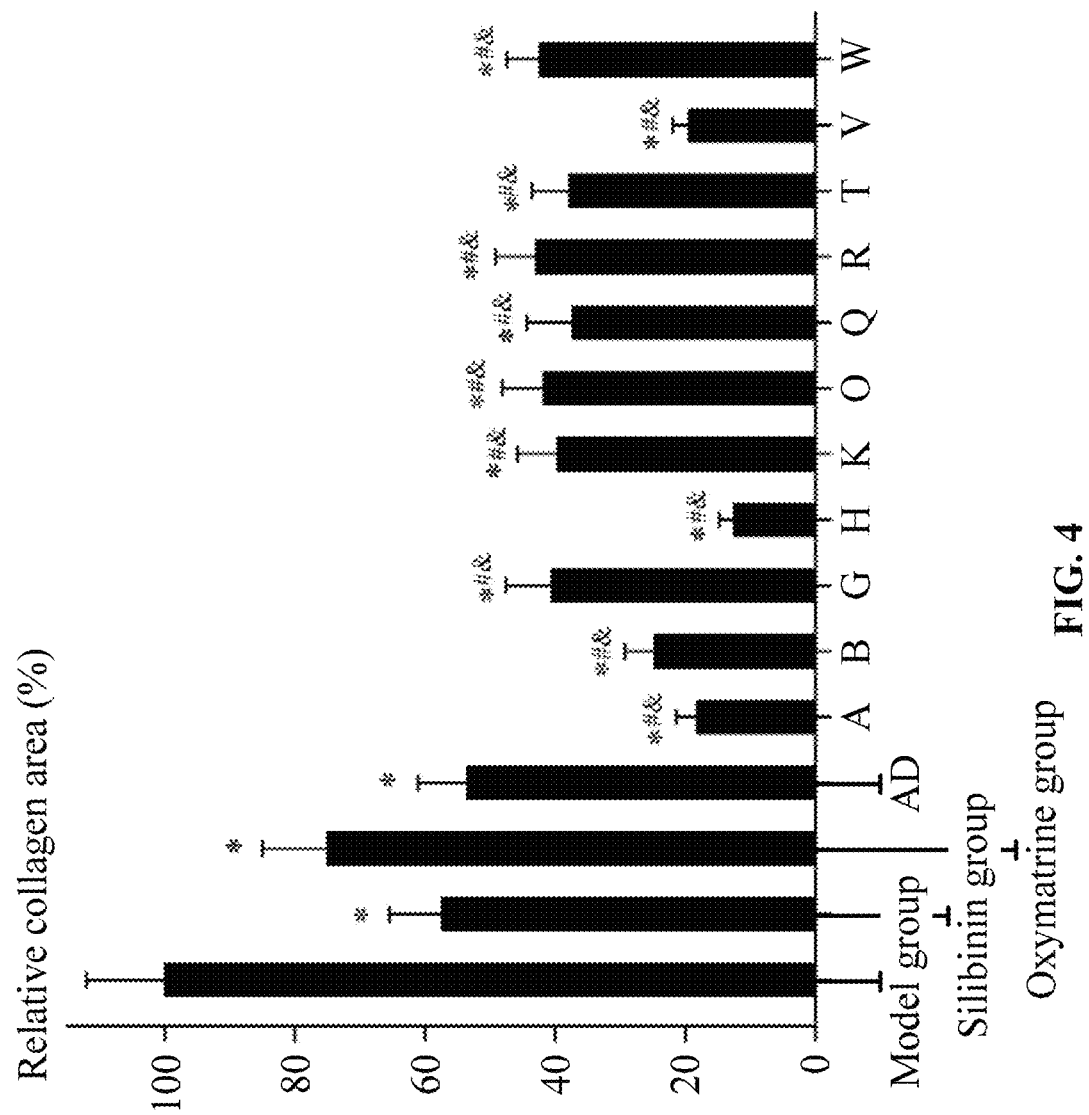
FIG. 4 is a graph showing the effect of partial representative compounds on the degree of $CCl_4$-induced liver fibrosis in SD rats (relative collagen area/%); compared with the model group, *P<0.05; compared with the AD group, $^\#$P<0.05; compared with the silibinin group, $^\&$P<0.05.
Figure 5:
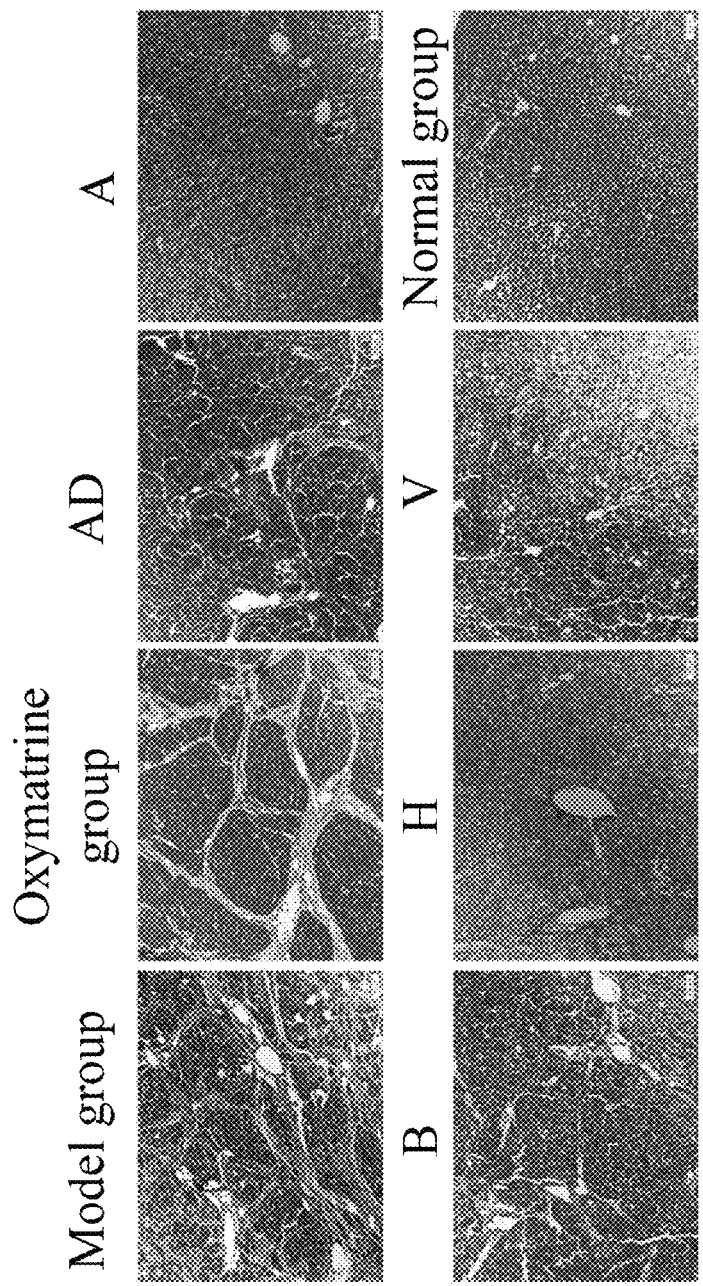
FIG. 5 is a graph showing the effect of partial representative compounds of the disclosure on the degree of $CCl_4$-induced liver fibrosis in SD rats (partial tissue after Masson's trichrome staining; ×100 times)

LX-2 cells in logarithmic growth phase were digested with 0.25% (w/v) trypsin, and diluted into $1.0\times10^6$/mL cell suspension with RPMI1640 medium containing 10% (v/v) fetal bovine serum. After each 96-well plate was filled with 200 μL cell suspension per well, the plates were placed in an incubator for 24 h in order to complete the cell fusion. The original medium was discarded, and the medium with 0.5% serum was added and re-synchronized for 12 h in order to streaking, and the cells were washed twice with PBS. Following the aspiration of 200 μL of RPMI1640 medium containing the test compound (5 μM), photographs were taken under a microscope. Each treatment was repeated in 4 wells and control group was set up. Following 48 h of incubation, the cells were photographed and measured under a microscope. Migration inhibition rate=1−(scratch distance at 0 h in administration group−scratch distance at 24 h)/(scratch distance at 0 h in blank group−scratch distance at 24 h)×100%. The results were shown in FIGS. 2A, 2B and 3. Data were expressed as mean±standard deviation ($\bar{X}\pm S$); There were significant differences between groups when P<0.05.

4. Experimental Results

Figure 1B:
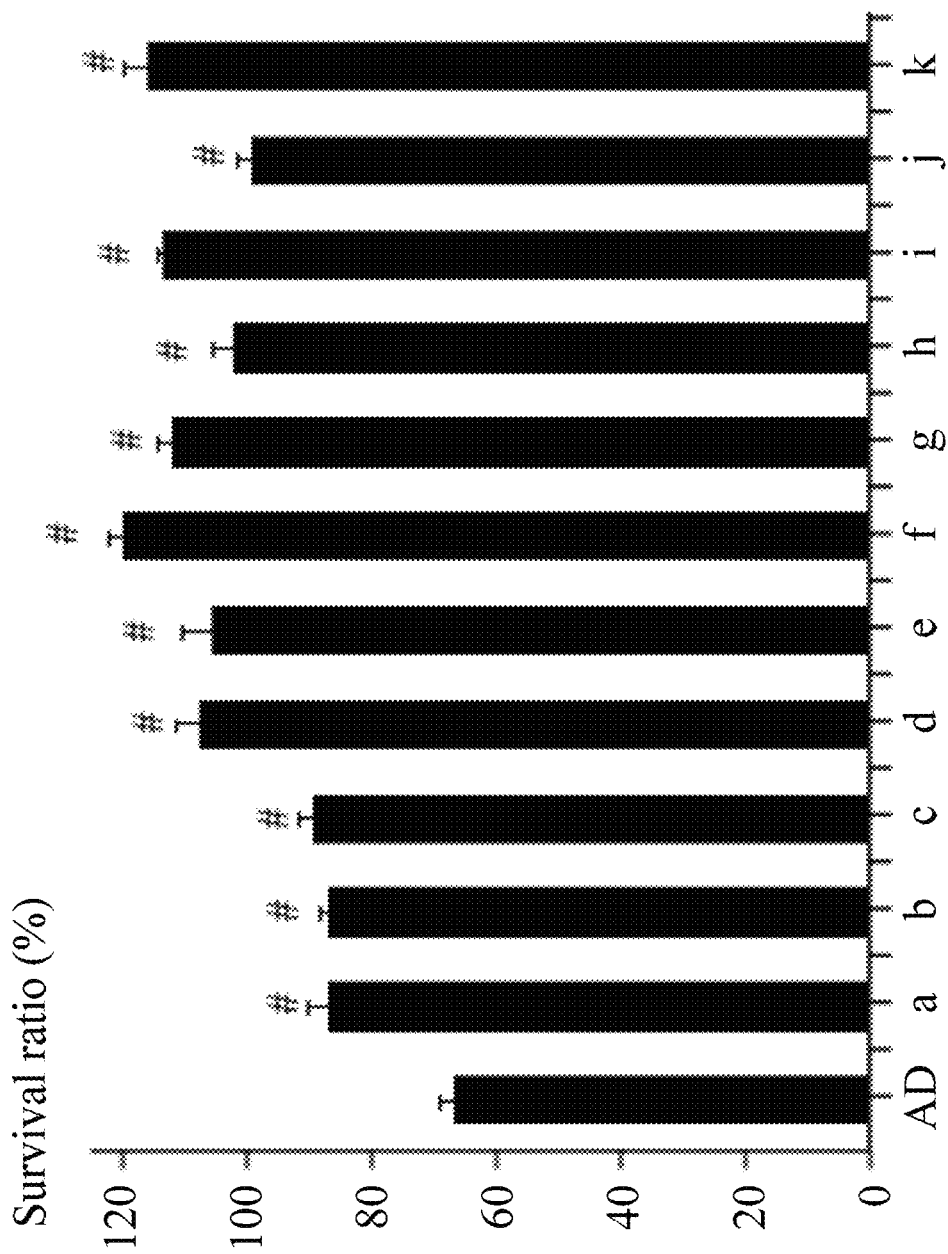
FIG. 1B shows the effect of AD and the representative compounds (30.00 μM) of the disclosure on the activity of human hepatic stellate cells LX-2; compared with the AD group, $^\#$P<0.05.

The results of FIGS. 1A and 1B showed that the compounds of the disclosure showed an absence of significant inhibition on the proliferation of human hepatic stellate cells at a concentration of 15 μM, and the survival rate was significantly higher than that of the parent compound AD. FIGS. 1A, 1B, 2A, 2B and 3, the results show that, the compound of the disclosure show significantly inhibition compared with AD on the migration of LX-2 cells at a non-toxic concentration, and has a stronger inhibitory effect on the migration of human hepatic stellate cells, and has a higher safety index.

Example 2

The Compounds of the Disclosure Reduce the Degree of Liver Fibrosis in SD Rats Induced by Carbon Tetrachloride ($CCl_4$)

The liver fibrosis model of rat induced by $CCl_4$ is one of the most commonly used animal models of liver fibrosis. This model shows great similarities with human liver fibrosis including morphology and pathophysiology. This rat model can thus serve as a good model for well simulating the pathological changes of human liver fibrosis, performing the features of toxic and drug-induced liver fibrosis, as well as the similar pathological features after hepatitis B virus (HBV) infection. After long-term stimulation of a low dose of $CCl_4$, animals showed abnormal liver function similar to human liver cirrhosis, furthermore, the molecular mechanism of fibrosis, serum markers after injury, and pathological changes of liver tissue were also very similar to humans. Therefore, the model of liver fibrosis induced by $CCl_4$ is widely used to study the pathogenesis of liver fibrosis, the screening of anti-fibrosis drugs, and the mechanism of anti-fibrosis drugs.

1. Materials and Methods

1) Experimental Animals

Clean-grade Sprague Dawley (SD) rats, healthy, male, body weight 200±20 g, were purchased from Hunan Silaike Jingda Laboratory Animal Co Ltd. (License No. SCXK (Xiang) 2011-0003).

2) Drugs, Reagents and their Preparation

Andrographolide was produced by Sichuan Shifang Jinxin Biotechnology Co., Ltd. (Batch No.: 120822), purity greater than 99%; the compounds of the disclosure were synthesized in a laboratory, purity greater than 99%; Pharmaceutical grade sodium carboxyl methyl cellulose (CMC-Na) was produced by Anhui Sunhere Pharmaceutical Excipients Co., Ltd. (Batch No.: 131114); Marine Capsules, was produced by Zhengda Tianqing Pharmaceutical Co., Ltd. (Batch No.: SDA License No.: GUOYAOZHUNZI H20010763). Silibinin Capsules, was produced by Tianjin Tianshili Shengte Pharmaceutical Co., Ltd. (Batch No.: SDA License No.: GUOYAOZHUNZI H20040299). Drug mixed with 0.5% CMC-Na. $CCl_4$ was produced by Tianjin Kaiji Chemical Reagent Co., Ltd. Other reagents were commercially available analytical grades.

2. Experimental Methods

Figure 6:
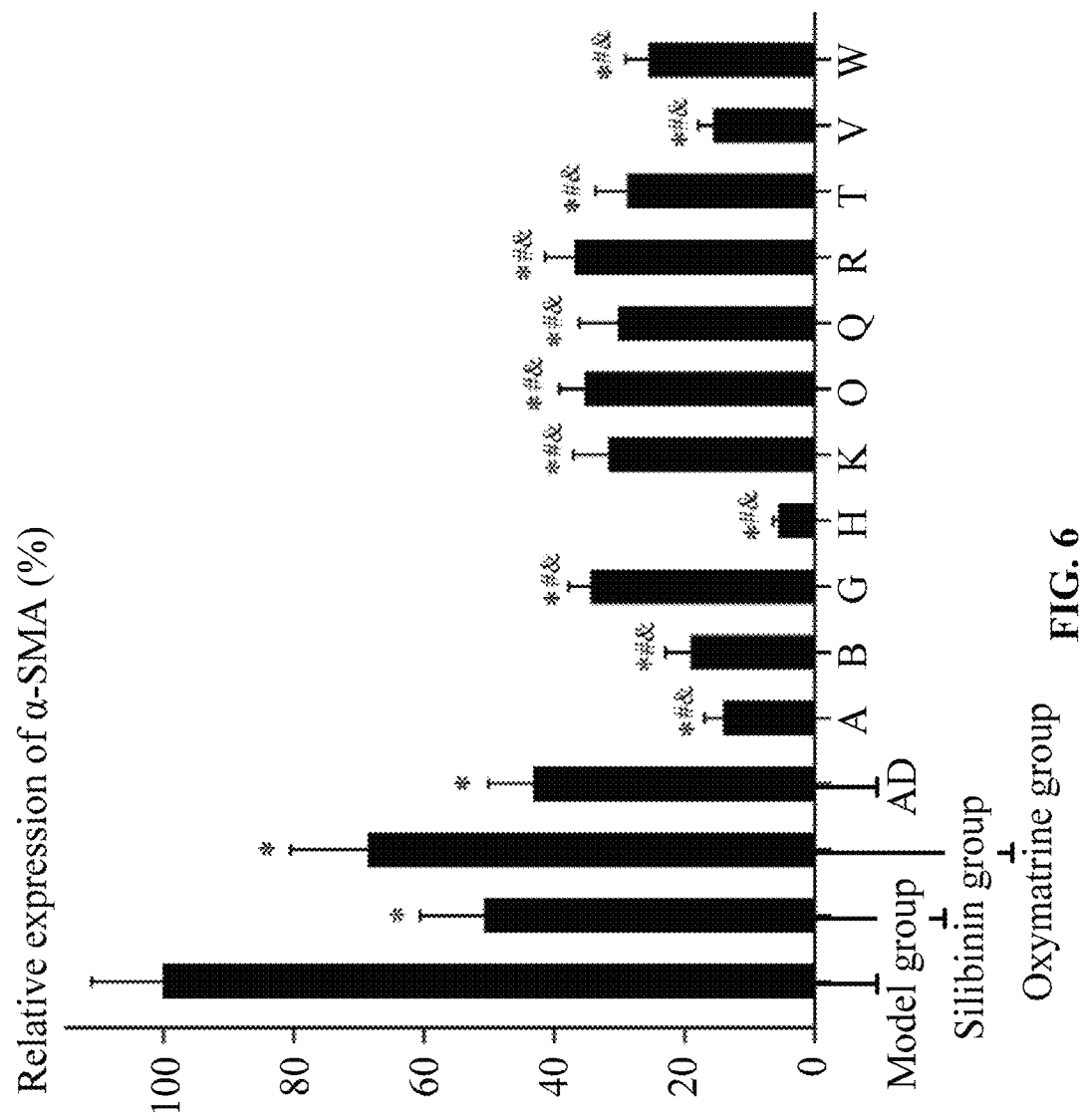
FIG. 6 is a graph showing the effect of some representative compounds on the expression of α-smooth muscle actin (α-SMA) in liver tissue of SD rats with $CCl_4$-induced liver (statistical results); compared with the model group, *P<0.05; compared with the AD group, #P<0.05; compared with the silibinin group, &P<0.05.
Figure 7:
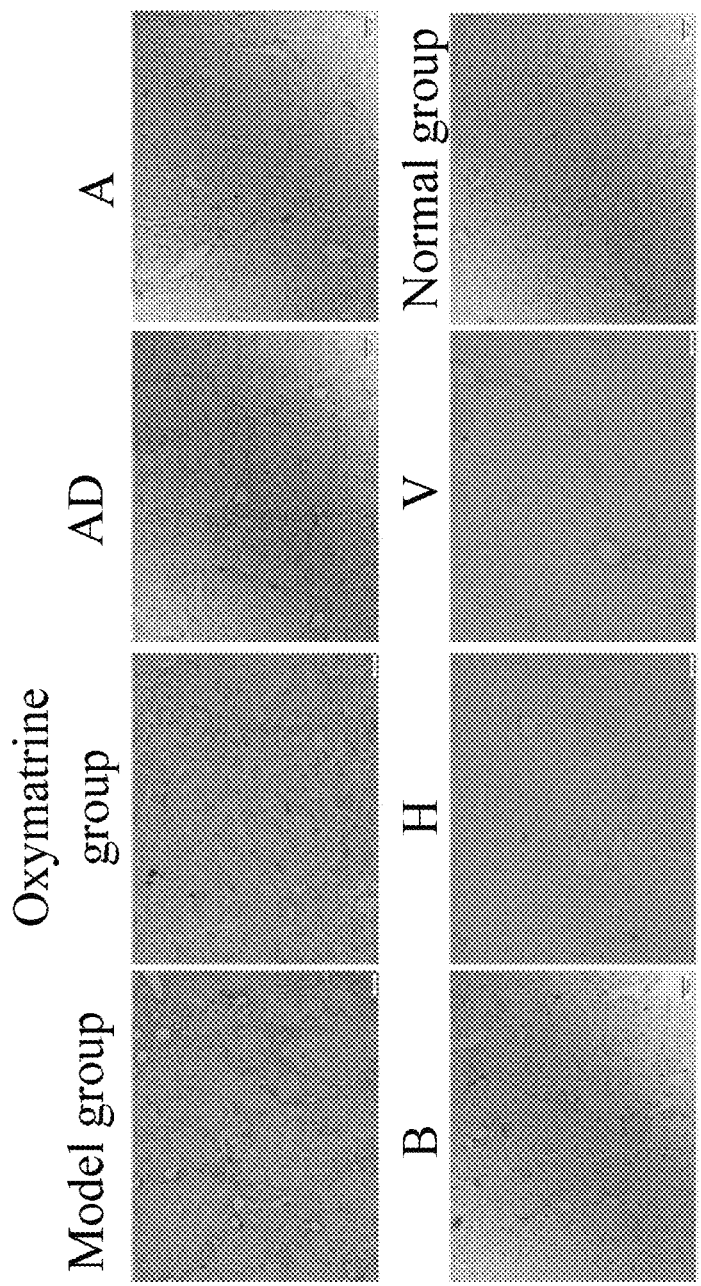
FIG. 7 is a graph showing the effect of partial representative compounds of the disclosure on the expression level of α-SMA in liver tissue of SD rats with CCl$_4$-induced liver fibrosis (partial immunohistochemistry picture; ×100 times)

SD rats were fed ad libitum for 3 days, and then randomly divided into normal group and model group. Subcutaneous injection of 40% $CCl_4$ of soybean oil to the rats of model group for the first time. Following an initial dose of 4 mL/kg, each subsequent dose was 2 mL/kg, 2 times every week. The corresponding volumes of soy oil were injected subcutaneously to the normal group. After 4 weeks of modeling, except for the normal group, other rats were weighed individually and then randomly divided into eight rats per group. The dosages of andrographolide, oxymatrine, silibinin and the compound A of the disclosure were both 20 mg/kg, and the doses of other compounds were the same molar mass as compound A, and the model group and the normal group were given an equal amount of 0.5% CMC-Na. During the 5th and 6th weeks of the experiment, modeling and administration were carried out simultaneously, furthermore, the modeling was stopped at the 7th and 8th weeks, while the administered continued to carry out. Drugs were administered by gavage on an empty stomach in the morning every day, and were given daily for 10 days followed by 1-day break. The bedding of the rats should be replaced at the first 8 hours of the last gavage, strictly fasting with nothing but water. After 1 h of administration, an anesthetic of 3% pentobarbital sodium (2 mL/kg) was intraperitoneally injected. The liver was quickly excised after blood collection. The collected blood was allowed to stand in an incubator at 37° C. for 45 min, and then the upper serum was collected by centrifugation at 3500 rpm for 15 min at 4° C. The liver of the lower left lobe of the rat was fixed in 10 times volume of 4% paraformaldehyde fixative, and the fixative was changed after 24 h. Pathological sections were obtained after fixation, and Masson's trichrome staining was then used to observe the degree of liver fibrosis. Image-Pro Plus software performed semi-quantitative analysis of fibrosis histology on the photographs of Masson stained sections. The relative collagen area=(average area of the administration group−average area of the normal group)/(average area of the model group−average area of the normal group)×100%, and the results were shown in FIGS. 1 and 2. The expression of α-SMA (a marker of the degree of HSC activation) in liver tissue was evaluated by immunohistochemistry, and the positive expression was quantified using Image-Pro Plus, the results were shown in FIGS. 6 and 7. Data were processed and analyzed using SPSS 17.0 statistical software. Data were expressed as mean±standard deviation ($\bar{X}\pm S$); There were significant differences between groups when $P<0.05$.

3. Experimental Results

The results of FIGS. 4, 5, 6 and 7 showed that the compounds of the disclosure significantly reduce the degree of fibrosis in liver tissue of animals. The collagen area of the liver tissue of the model group of the disclosure was significantly reduced compared with AD, with more prominent effect compared with the positive reference silibinin and oxymatrine. Furthermore, it was observed that the compound of the disclosure significantly down-regulated the expression level of α-SMA in liver tissue, and the difference was significant compared with AD, and the effect was even better than that of the drug in the positive control group.

Example 3

Compounds of the Disclosure Significantly Reduce the Degree of Liver Fibrosis Induced by Porcine Serum in Wistar Rats.

1 Materials and Methods

1) Experimental Animals

Clean grade Wistar rats, healthy, male, body weigh 140±20 g, were purchased from Nanjing Junke Bioengineering Co., Ltd. (license No. SCXK (Liao) 2015-0001).

2) Drugs, Reagents and their Preparation

Silibinin Capsules, was produced by Tianjin Tianshili Shengte Pharmaceutical Co., Ltd. (Batch No.: SDA License No.: GUOYAOZHUNZI H20040299). Pig serum, was produced by Guangzhou Ruite Biotechnology Co., Ltd. (Batch No.: 160608). Other test drugs and compounds were the same as in Example 2, and other reagents were commercially available analytical grades. The drugs were formulated as a 0.5% sodium carboxymethylcellulose (CMC-Na) suspension.

3. Experimental Results

Figure 8:
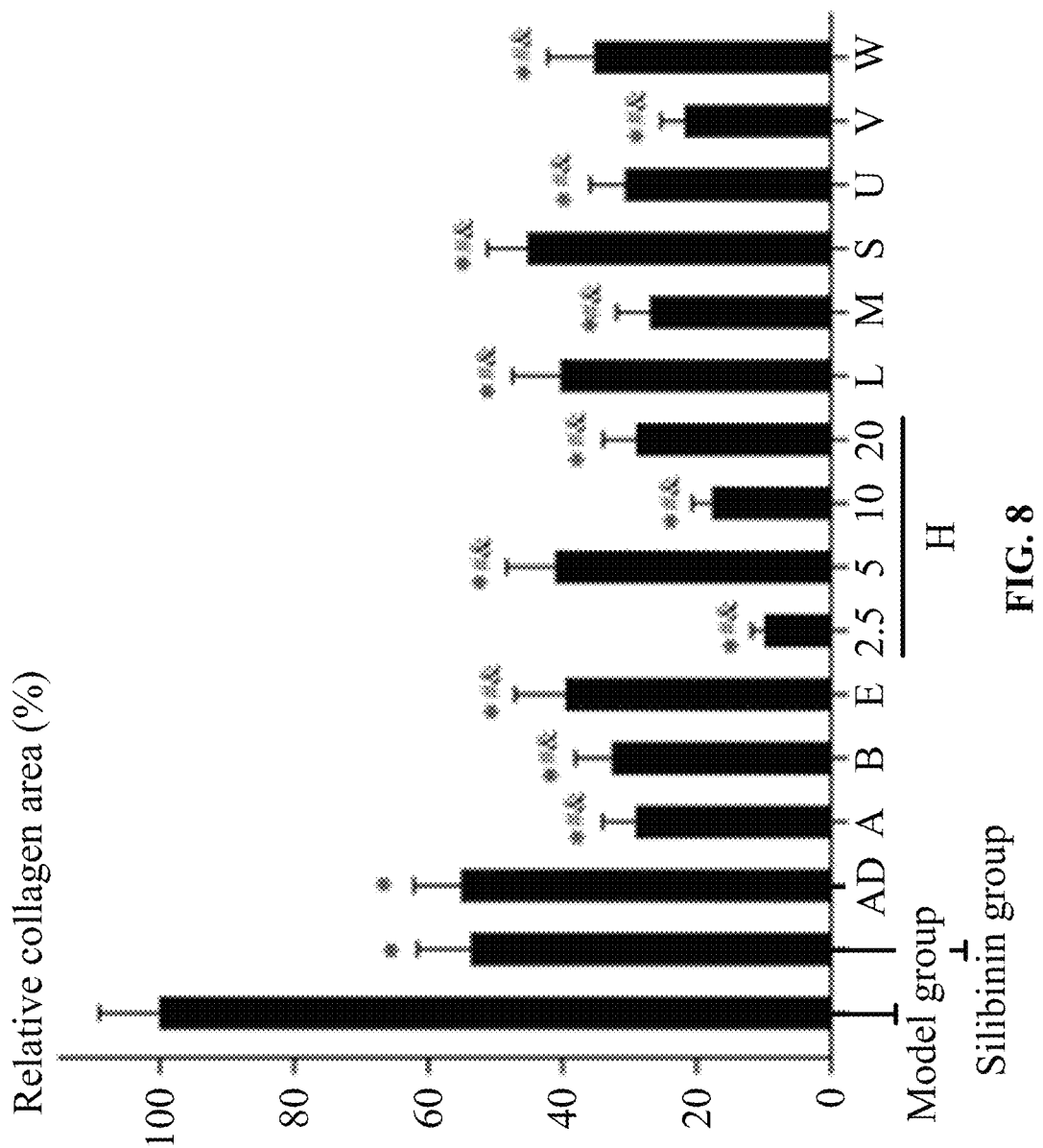
FIG. 8 is a graph showing the effect of partial representative compounds of the disclosure on liver fibrosis induced by porcine serum in Wistar rats (relative collagen area/%); compared with the model group, *P<0.05; compared with the AD group, #P<0.05; compared with the silibinin group, &P<0.05.
Figure 9:
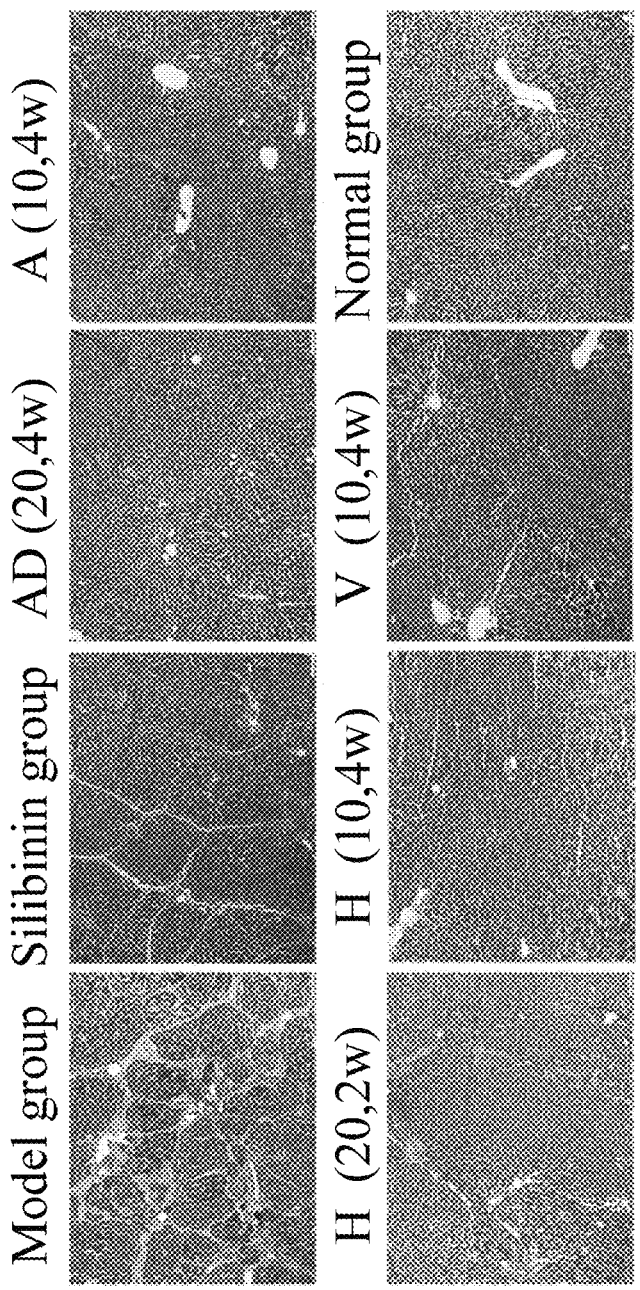
FIG. 9 is a graph showing the effect of partial representative compounds of the disclosure on the degree of liver fibrosis in Wistar rats induced by porcine serum (partial tissue of Masson's trichrome staining; ×100 times)
Figure 10:
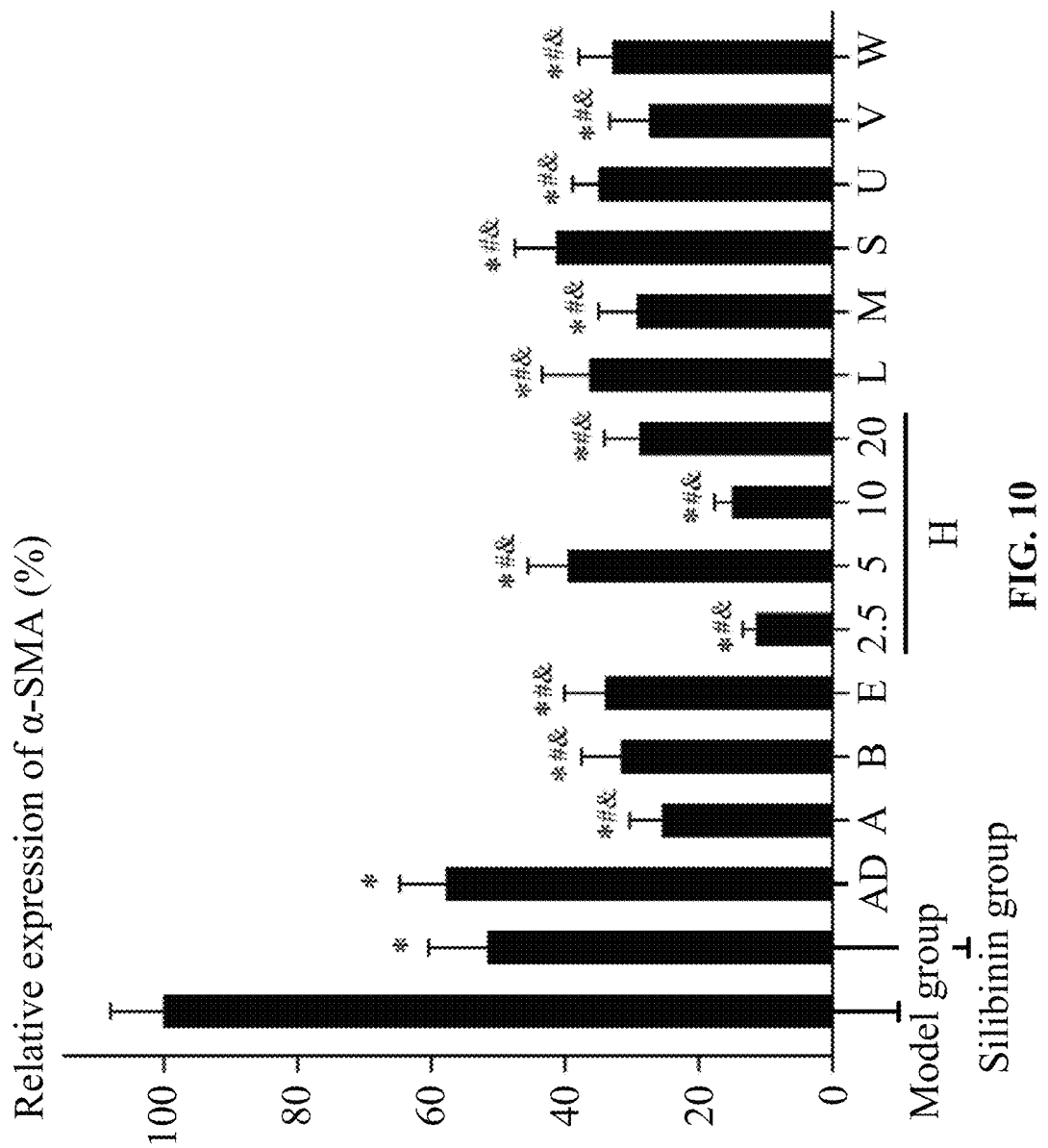
FIG. 10 is a graph showing the effect of partial representative compounds on the expression of α-SMA in liver tissue of Wistar rats induced by porcine serum (statistical results); compared with the model group, *P<0.05; compared with the AD group, #P<0.05; compared with the silibinin group, &P<0.05.
Figure 11:
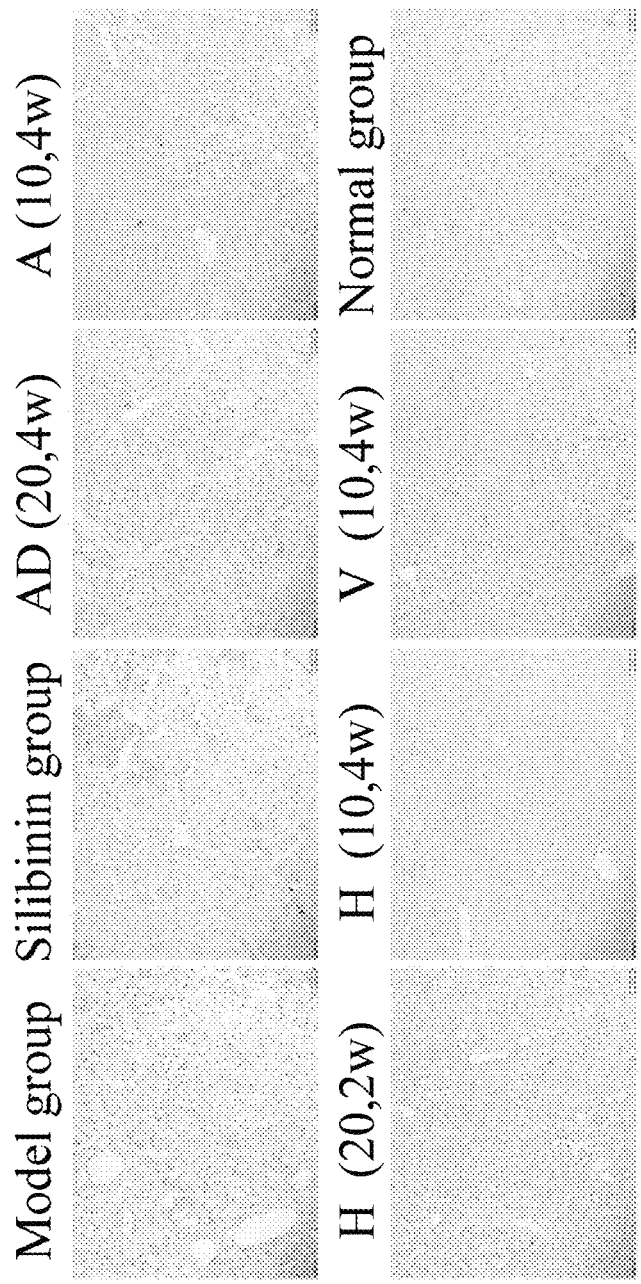
FIG. 11 is a graph showing the effect of partial representative compounds of the disclosure on the expression level of α-SMA in liver tissue of Wistar rats induced by porcine serum (partial immunohistochemistry image; ×100 times)

After Wistar rats were fed ad libitum for 3 days, they were weighed individually and then randomly divided into six rats per group. Except for the normal group, other rats were intraperitoneally injected with porcine serum, 1 mL/time, 2 times every week, lasting for six weeks. The same dose of normal saline was injected to the rats of normal group. The experiment was finished until the end of 8th weeks. Drugs were administrated by gavage on an empty stomach in the morning every day, and were given daily for 10 days followed by 1-day break. The preventive administration group (H: 2.5 mg/kg) was administered from the day of modeling. The rats in 50 mg/kg silibinin group, 20 mg/kg andrographolide group, 5 mg/kg compound H group and 10 mg/kg compound H group were administered beginning the 5th week, while the rats in the 20 mg/kg compound H group was administered from the 7th week. The control group and the model group were administered with 0.5% CMC-Na via gavage. The methods of rat liver collection and fixation, serum preparation, pathological section preparation, and Masson's trichrome stain were the same as in Example 2, and the results were shown in FIGS. 8 and 9. The expression of α-SMA (a marker of the degree of HSC activation) in liver tissue was evaluated by immunohistochemistry, and the positive expression was quantified using Image-Pro Plus, the results were shown in FIGS. 10 and 11. Data were processed and analyzed using SPSS 17.0 statistical software. Data were expressed as mean±standard deviation ($\bar{X}\pm S$); There were significant differences between groups when $P<0.05$.

2. Experimental Results

The results of FIGS. 8, 9, 10, and 11 showed that the compounds of the disclosure produced good anti-fibrosis effects on the pig serum-induced liver fibrosis model. Prophylactic or therapeutic administration both exhibited significantly reduced degree of liver fibrosis in rats, whose effect was better than that of the AD and 50 mg/kg silibinin group. Compound H group also exhibited good therapeutic effect and although the rats in this group were administered from the 6th week of modeling and this lasted for two weeks. Furthermore, it was observed that the compounds of the disclosure significantly down-regulated the expression level of α-SMA in liver tissue, and the difference was significant compared with AD, and the effect was even better than that of the positive drug, indicating that the anti-fibrosis effect was related to the inhibition of hepatic stellate cell activation.

Example 4

The Compound of the Disclosure Significantly Reduces the Degree of Liver Fibrosis in SD Rats Induced by BDL 1. Materials and Methods 1) Experimental Animals Clean grade SD rats, healthy, male, body weigh 200±20 g, were purchased from Hunan Silaike Jingda Laboratory Animal Co Ltd. (License No. SCXK (Xiang) 2016-0002).

2) Drugs, Reagents and their Preparation

Ursodeoxycholic acid, was produced by Shanghai Xinyi Pharmaceutical Co., Ltd. (Batch No.: SDA License No.: GUOYAOZHUNZI H31021875). Other test drugs and compounds were the same as in Example 2, and other reagents were commercially available analytical grades. The drugs were formulated as a 0.5% sodium carboxymethylcellulose (CMC-Na) suspension.

3) Experimental Method

After SD rats were fed ad libitum for 3 days, they were weighed individually and were randomly divided into six groups including a sham-operated control group, a model group, two AD control groups (5 mg/kg and 20 mg/kg), an ursodeoxycholic acid control group (25 mg/kg), and a compound H group, six rats per group. The sham operation group and the model group were administered with 0.5% CMC-Na via gavage, and the other administration groups were administered 0.5% CMC-Na suspension of the corresponding drug, and the administration lasted for 4 weeks. The bedding of the rats should be replaced at the first 8 hours of the last gavage, strictly fasting with nothing but water. The rats were intramuscularly injected with 80,000 U/mu of penicillin 2 h before gavage, and 3% sodium pentobarbital (2 mL/kg) was intraperitoneally injected 1 h after gavage. After limb immobilization in a supine position, the rats were anesthetized. The abdomen of the rats was shaved and then swabbed with iodine to sterilize the skin regions. The abdomen was opened along the abdominal wall in the midline. The duodenum was pulled upwards and separated from the common bile duct. Double-ligated with 4/0 silk thread and disconnected the common bile duct with a distance of 0.5 cm away from the hepatic hilum. The 3/0 silk thread continuous suture method was used to close the abdomen layer by layer. The wound was rinsed with iodine, and the rats were cultured in a 37° C. warm environment until the animals were fully awake. The control group only performed anesthesia, laparotomy and freed common bile duct, but did not ligate and break the common bile duct.

Figure 12:
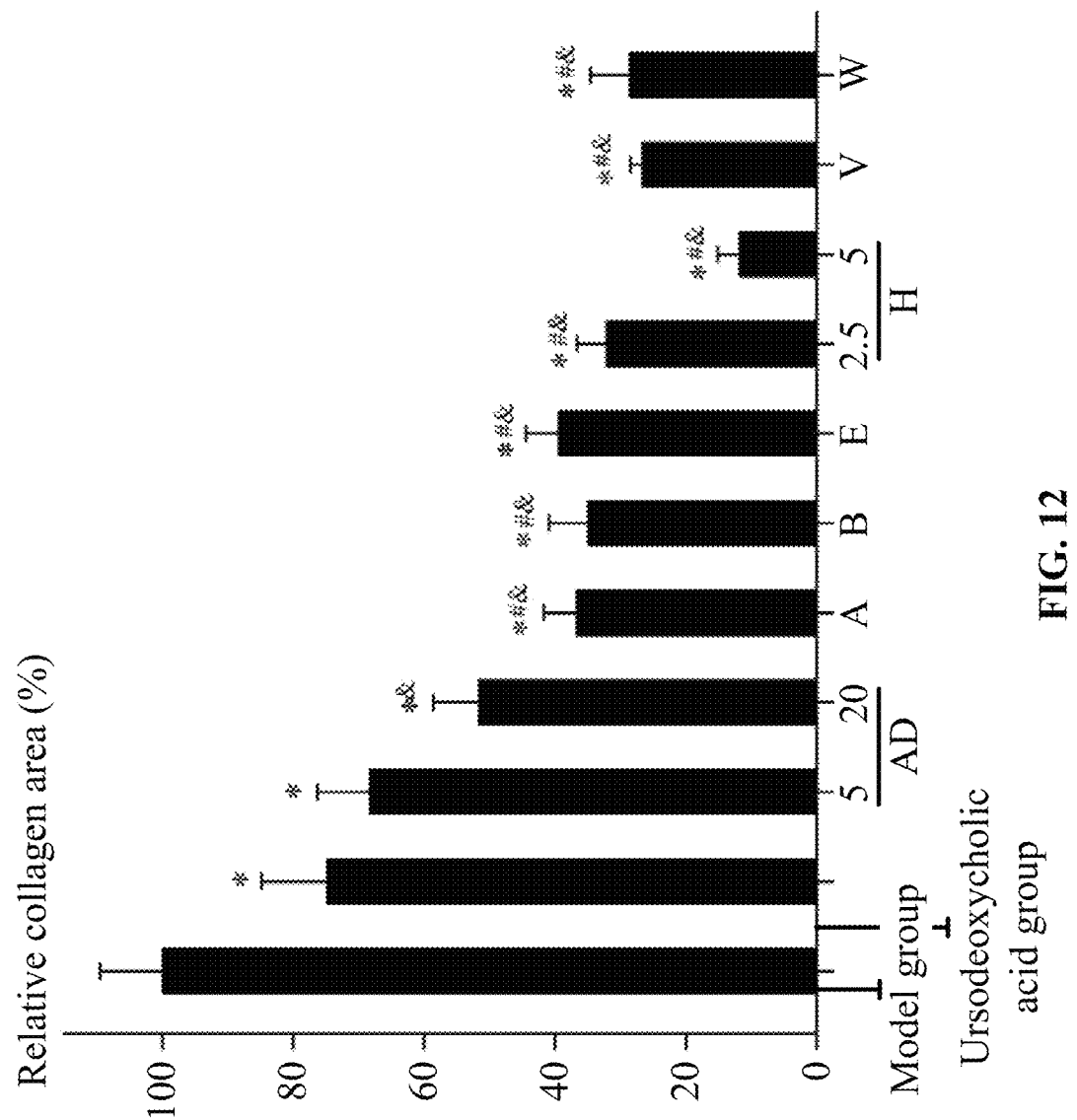
FIG. 12 is a graph showing the effect of partial representative compounds on the degree of BDL-induced liver fibrosis in SD rats (relative collagen area/%); compared with the model group, *P<0.05; compared with the AD group, #P<0.05; compared with the ursodeoxycholic acid group, &P<0.05.
Figure 13:
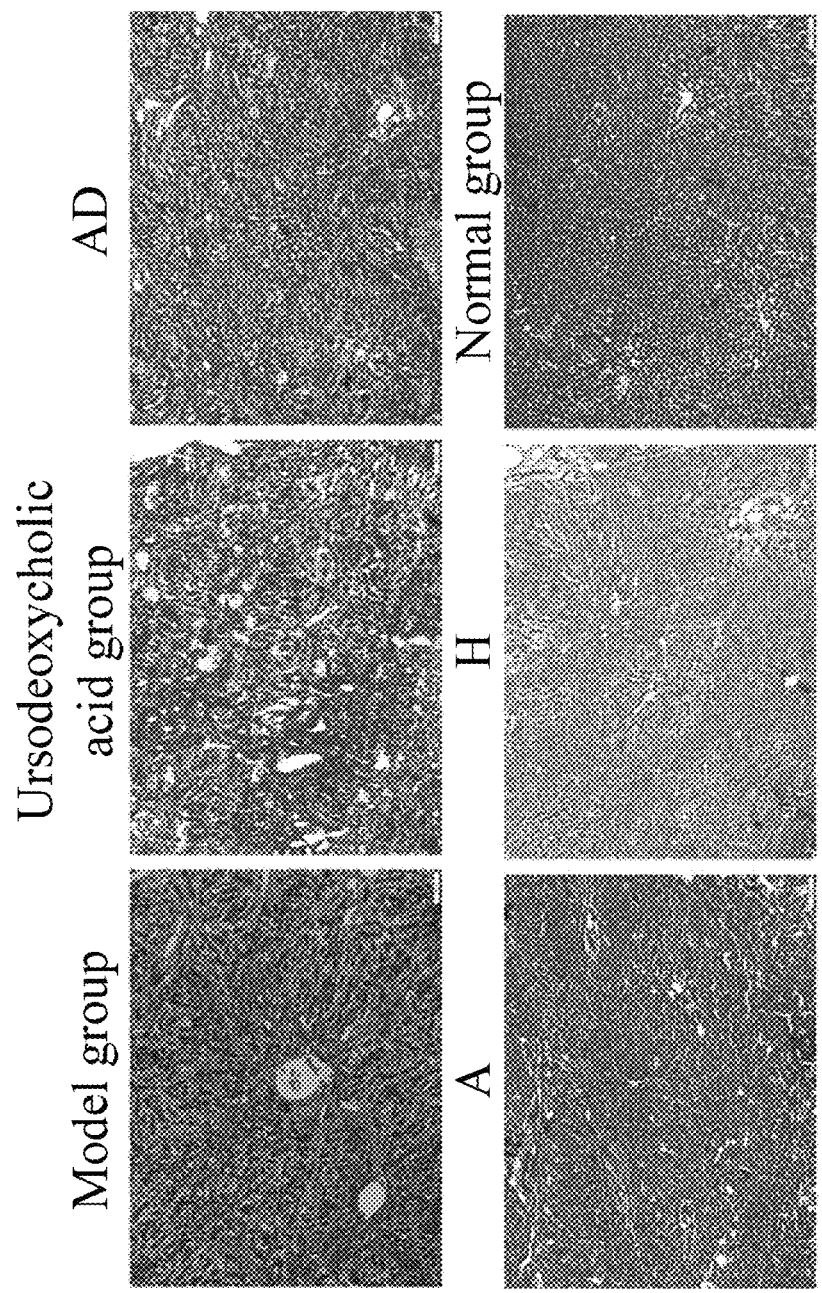
FIG. 13 is a graph showing the effect of partial representative compounds of the disclosure on the degree of BDL-induced liver fibrosis in SD rats (partial tissue of Masson's trichrome staining; ×100 times)
Figure 14:
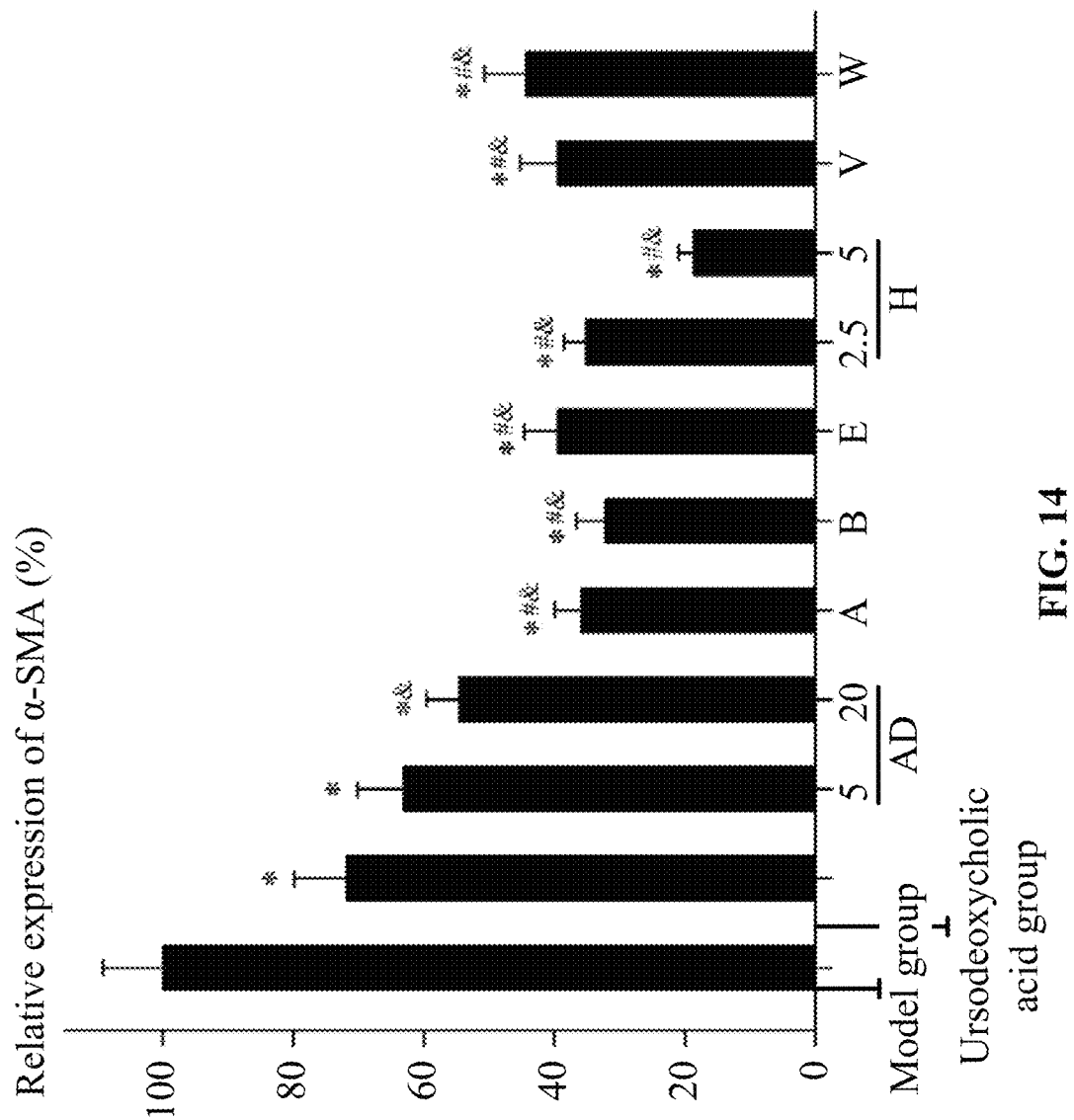
FIG. 14 is a graph showing the effect of partial representative compounds on the expression of α-SMA in liver tissue of SD rats induced by BDL (statistical results); compared with the model group, *P<0.05; compared with the AD group, #P<0.05; compared with the ursodeoxycholic acid group, &P<0.05.
Figure 15:
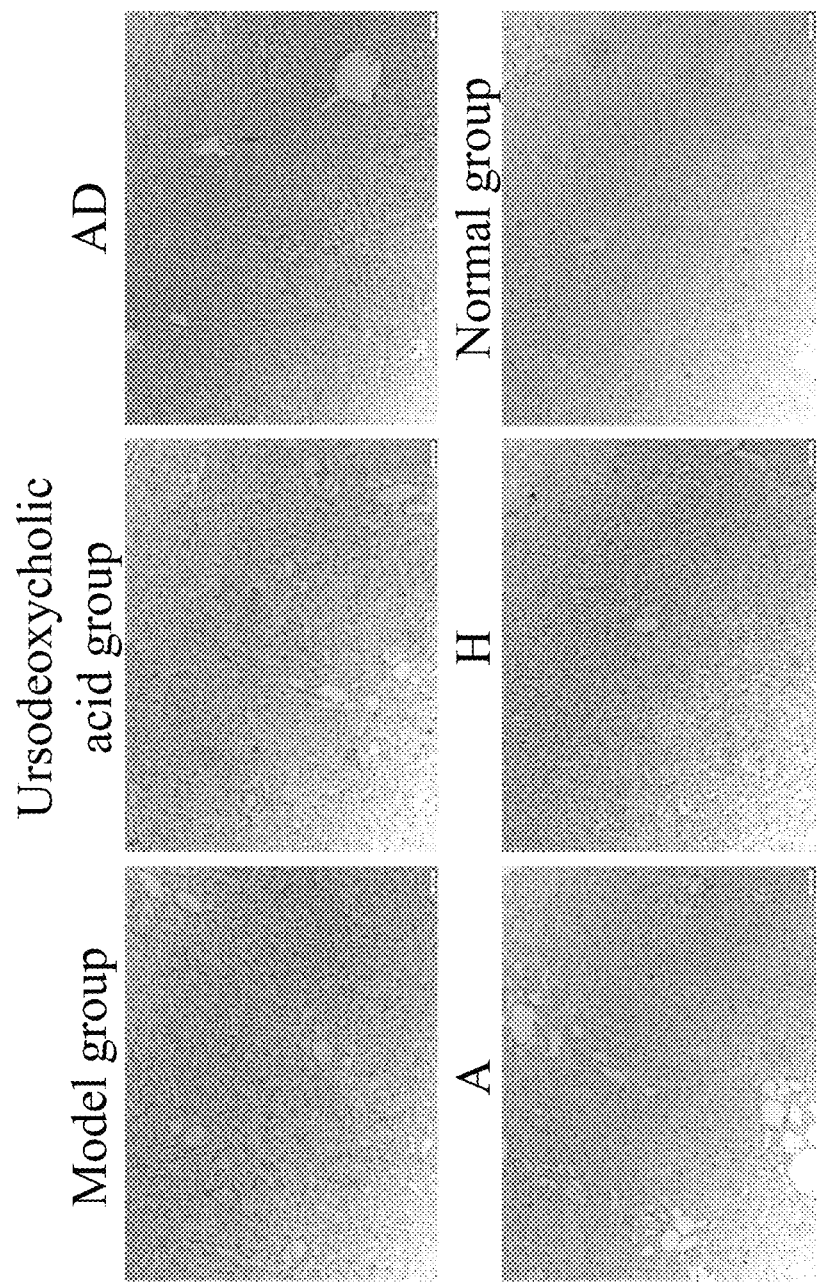
FIG. 15 is a graph showing the effect of partial representative compounds of the disclosure on the expression level of α-SMA of SD rats with liver fibrosis induced by BDL (partial immunohistochemistry image; ×100 times)
Figure 16:
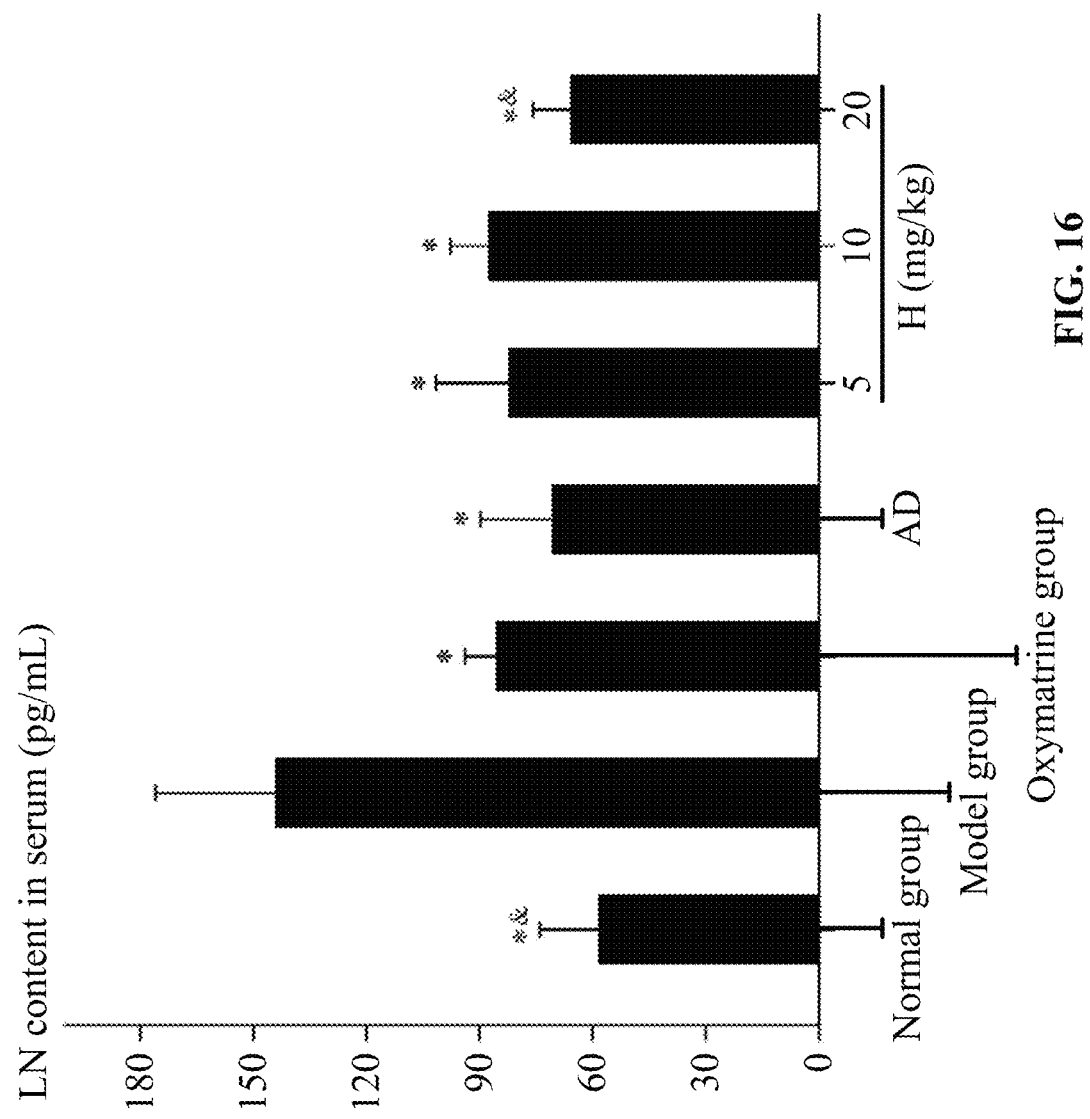
FIG. 16 is a graph showing the effect of representative compound H on the level of laminin (LN) in serum of SD rats with liver fibrosis induced by CCl$_4$; compared with the model group, *P<0.05; compared with the oxymatrine group, &P<0.05.
Figure 17:
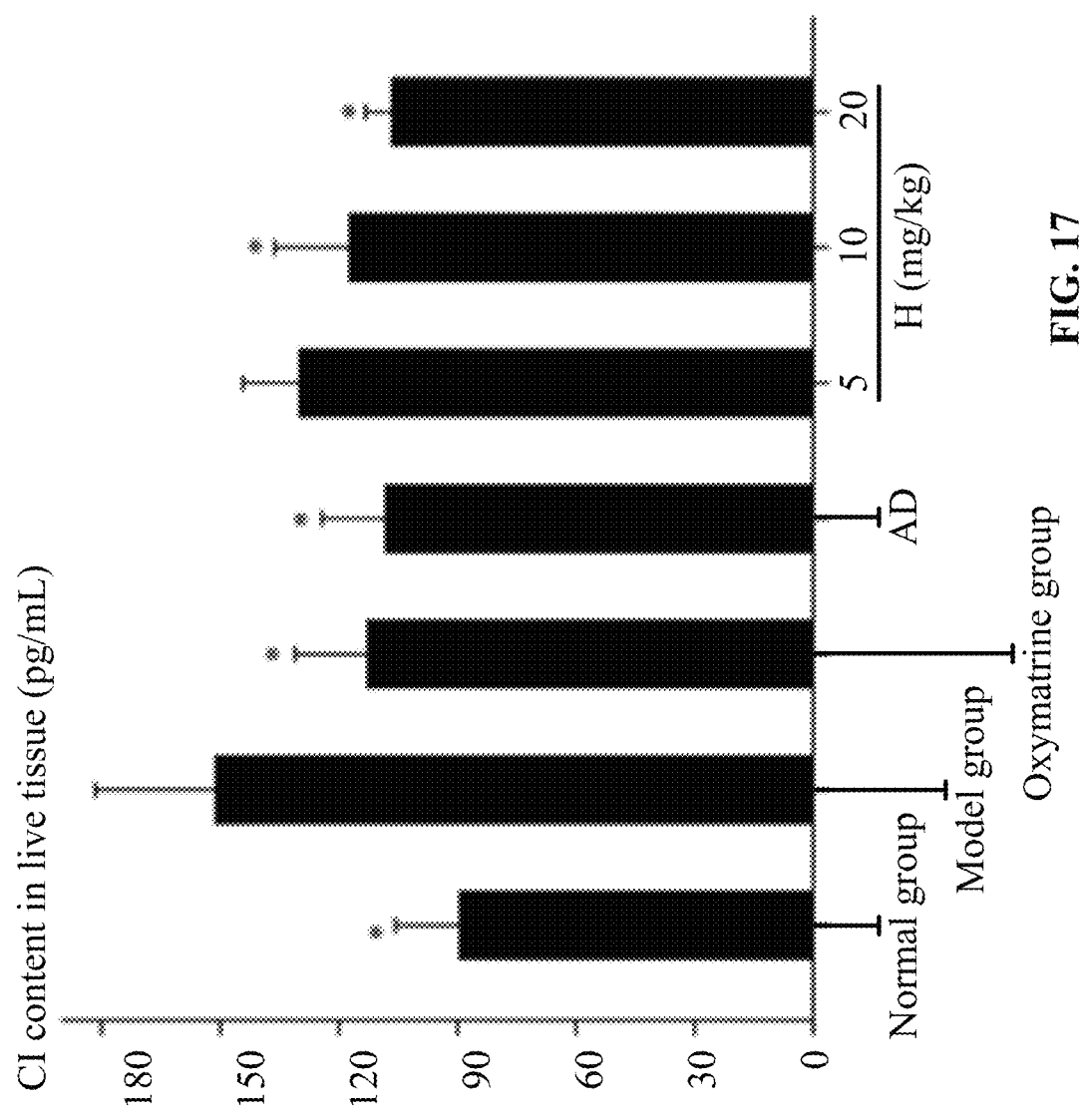
FIG. 17 is a graph showing the effect of representative compound H on the level of type I collagen (C-I) in the liver tissues of SD rats with liver fibrosis induced by CCl$_4$; compared with the model group, *P<0.05.
Figure 18:
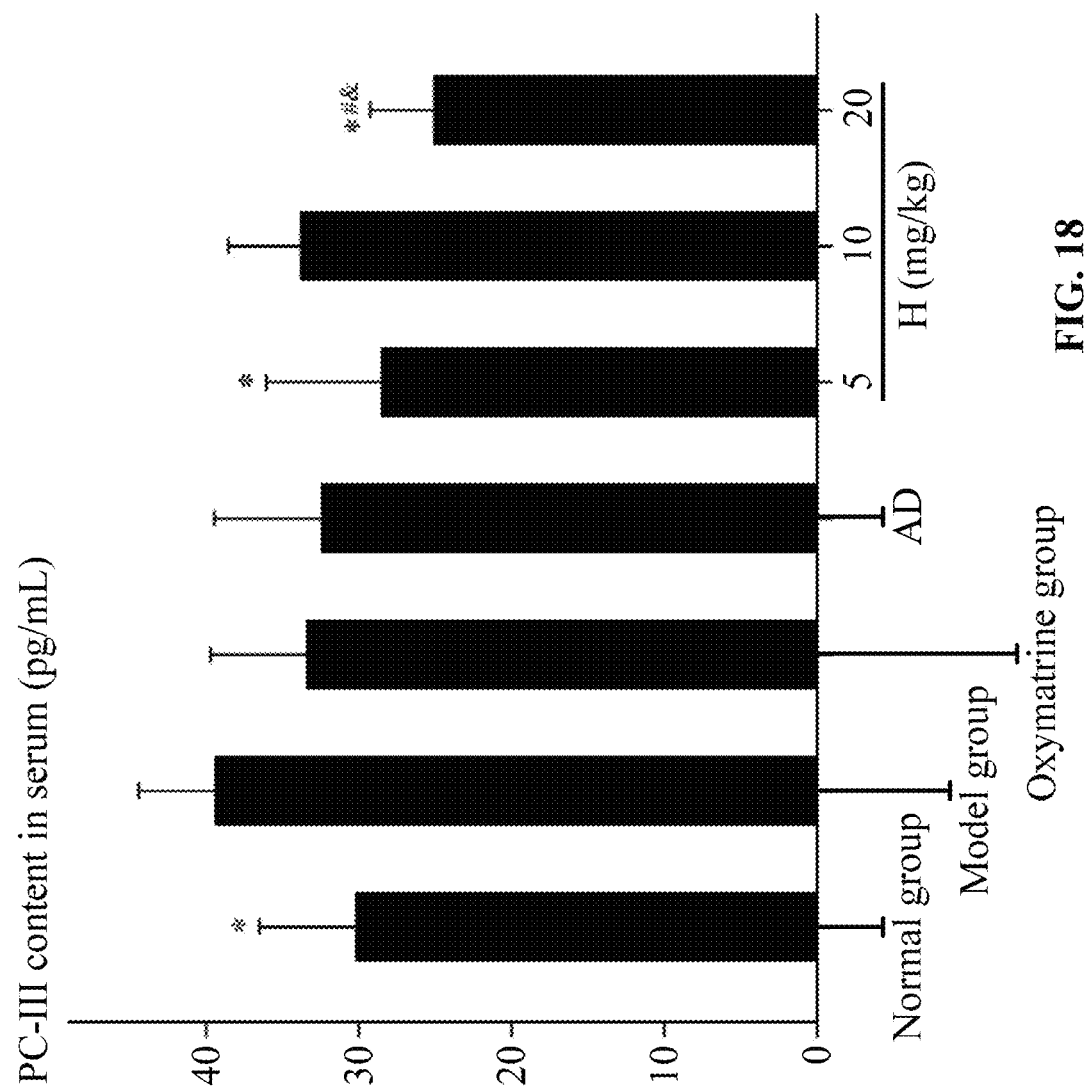
FIG. 18 is a graph showing the effect of representative compound H on the level of type III procollagen (PC-III) in serum of SD rats with liver fibrosis induced by CCl$_4$; compared with the model group, *P<0.05; compared with the AD group, #P<0.05; compared with the oxymatrine group, &P<0.05.
Figure 19:
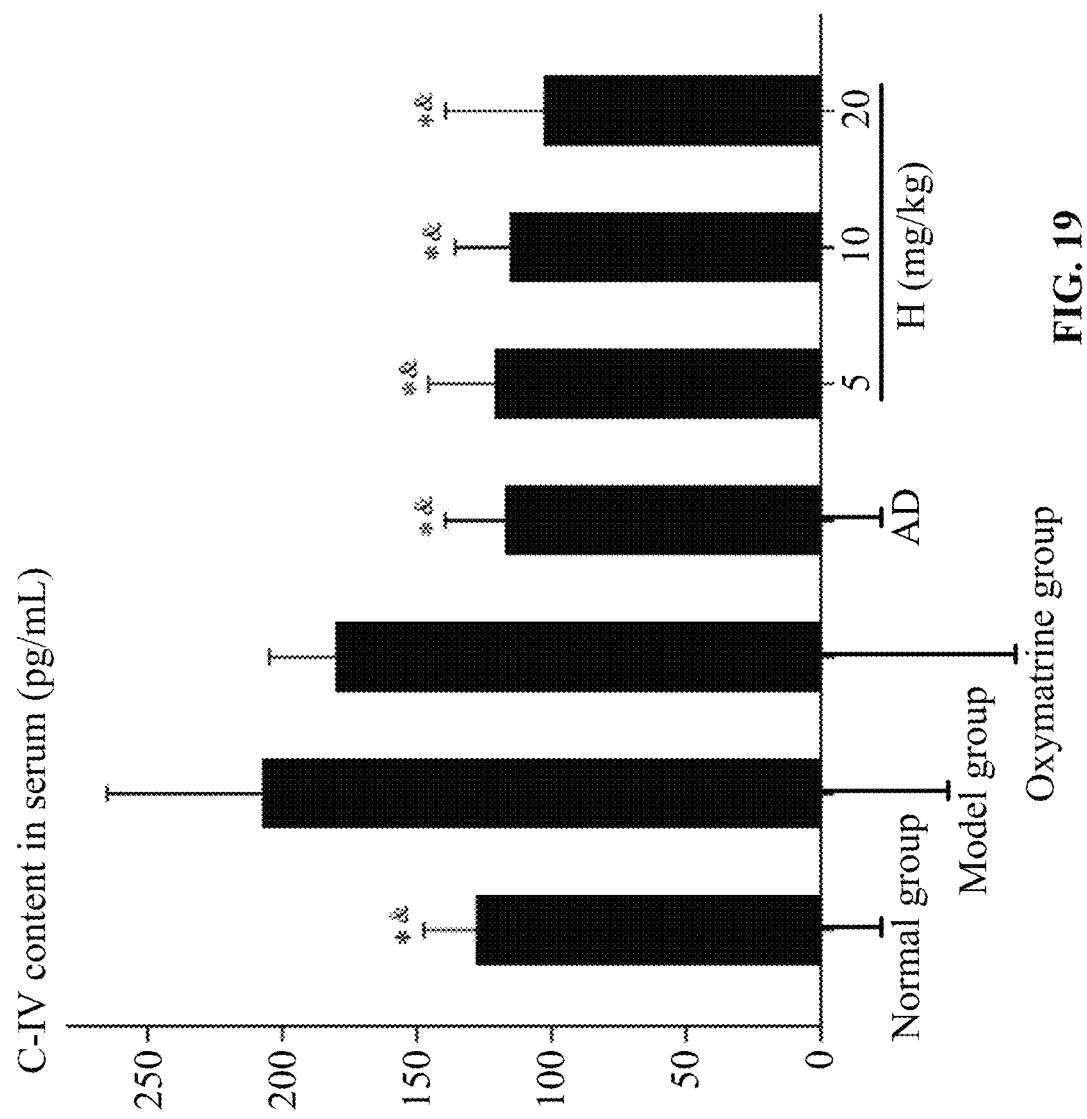
FIG. 19 is a graph showing the effect of representative compound H on the level of type IV collagen (C-IV) in serum of SD rats with liver fibrosis induced by CCl$_4$; compared with the model group, *P<0.05; compared with the oxymatrine group, &P<0.05.

Drugs were administered by gavage on an empty stomach in the morning every day, and were given daily for 10 days followed by 1-day break. The results of rat liver collection and fixation, serum preparation, pathological section preparation, and Masson's trichrome staining were the same as in Example 2, and the results were shown in FIGS. 12 and 13. The expression of α-SMA (a marker of the degree of HSC activation) in liver tissue was evaluated by immunohistochemistry, and the positive expression was quantified using Image-Pro Plus, the results were shown in FIGS. 14 and 15. Data were processed and analyzed using SPSS 17.0 statistical software. Data were expressed as mean±standard deviation ($\overline{X}\pm S$); There were significant differences between groups when $P<0.05$.

2. Experimental Results

The results of FIGS. 12, 13, 14, and 15 showed that the anti-liver fibrosis effect of the compound of the disclosure was significantly stronger than that of AD and positive drug treatment in the model of rat liver fibrosis induced by bile duct ligation. Furthermore, it was observed that the compound of the disclosure significantly down-regulated the expression level of α-SMA in liver tissue, and the difference was significant compared with AD, and the effect was better than that of the positive drug.

Example 5

Effect of the Compound of the Disclosure on Serum Indices of Collagen of Liver Fibrosis Induced by Carbon Tetrachloride ($CCl_4$) in SD Rats In normal liver tissue, collagen is an important component of the sinus interstitial membrane, which is mainly C-I and C-IV. When the liver was damaged, a large amount of collagen and glycoprotein were transcribed, translated and assembled, which is mainly LN, C-I and C-III. Serum LN, C-I, PC-III and C-IV levels were important indicators for the clinical diagnosis of patients with fibrosis.

1. Materials and Methods

The same as Example 2.

The levels of LN, C-I, PC-III and C-IV in the serum of the animals were determined by ELISA using the compound H of the disclosure as a representative. The changes in tissue and serum collagen index were shown in FIGS. 16-19. Data were processed and analyzed using SPSS 17.0 statistical software. Data were expressed as mean±standard deviation ($\overline{X}\pm S$); There were significant differences between groups when $P<0.05$.

2. Experimental Results

The results showed that the LN and the three collagen contents in the model group were significantly increased compared with the normal group. The treatment group significantly reduced the LN content in the liver tissue, and the high dose group of the compound H of the disclosure was significantly different from the positive drug oxymatrine group. Oxymatrine, AD and the compounds of the disclosure all significantly reduced the content of C-I in liver tissue, compound H decreased the C-I level in a dose-dependent manner; low-dose and high-dose compound H group significantly reduced the level of PC-III in the serum. Especially when the concentration was 20 mg/kg, it was significant compared with the oxymatrine group and the AD group; Oxymatrine, AD and compound H significantly reduced the content of C-IV in the serum, and compound H decreased the serum C-IV level in a dose-dependent manner.

The results of FIGS. 16, 17, 18, and 19 showed that the compound of the disclosure significantly enhances the inhibitory activity against PC-III while maintaining the significant decrease in the levels of LN, C-I and C-IV of the parent compound AD. The compound of the disclosure lowered LN, PC-III, C-IV to a normal level at a dose of 20 mg/kg. The degree of down-regulation of PC-III and C-IV by compound H at the dose of 5 mg/kg was comparable to that of AD at the dose of 20 mg/kg.

Example 6

Effect of the Compound of the Disclosure on Serum IL-6 and TNF-α Levels in Liver Fibrosis of SD Rats Induced by Carbon Tetrachloride ($CCl_4$)

Activation of HSC can induce macrophages to produce large amounts of TNF-α, continue to participate in the differentiation of HSC, and also enhance the inflammatory response in the liver. IL-6, which is one of the pro-fibrotic factors, is involved in complex physiological processes such as inflammation, lipid peroxidation, apoptosis and regeneration in liver tissue, and is also an effector molecule downstream of NF-κB.

1 Materials and Methods

The same as Example 2.

Figure 20:
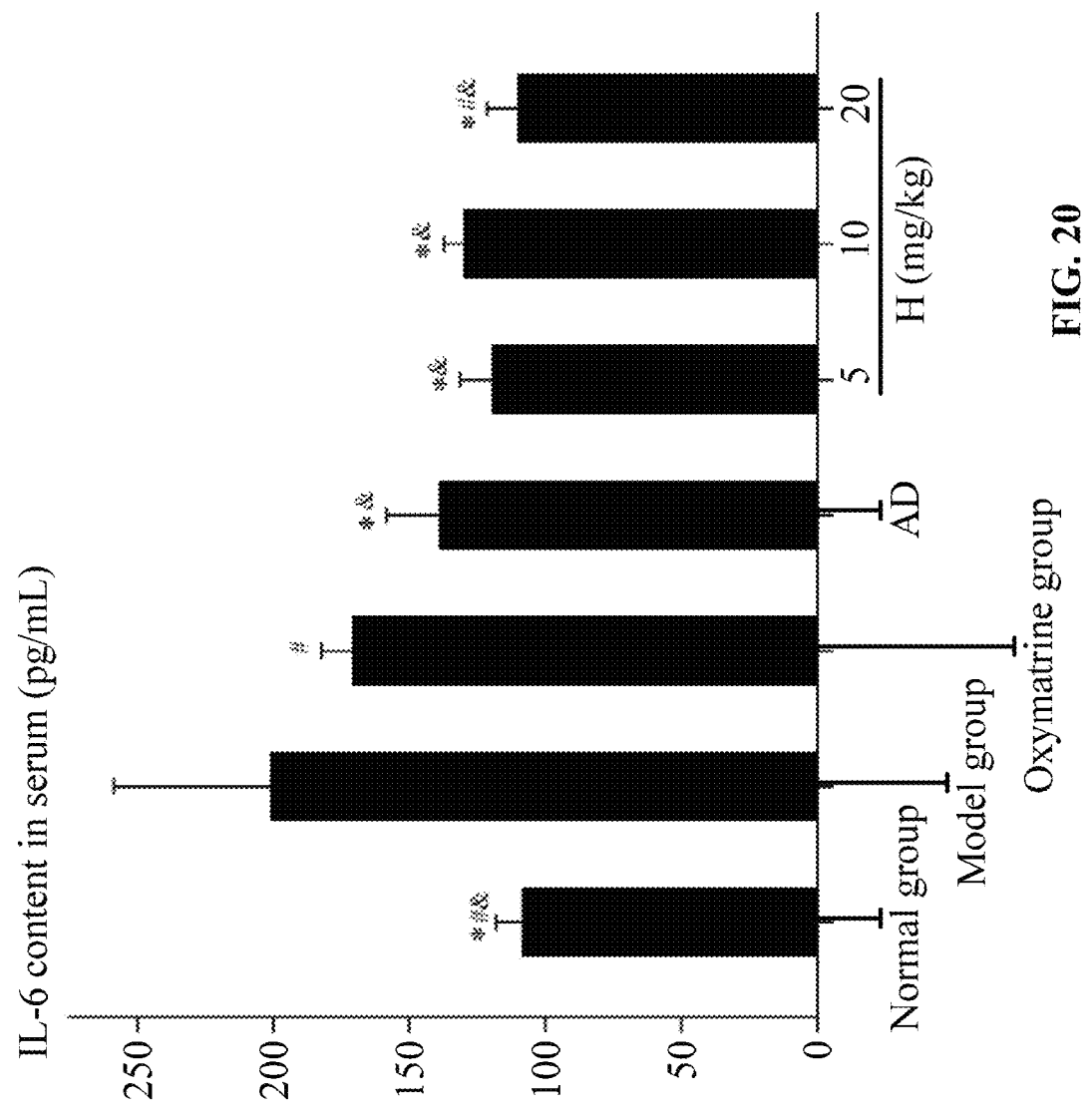
FIG. 20 is a graph showing the effect of representative compound H on the level of interleukin-6 (IL-6) in serum of SD rats with liver fibrosis induced by CCl$_4$; compared with the model group, *P<0.05; compared with the AD group, #P<0.05; compared with the oxymatrine group, &P<0.05.
Figure 21:
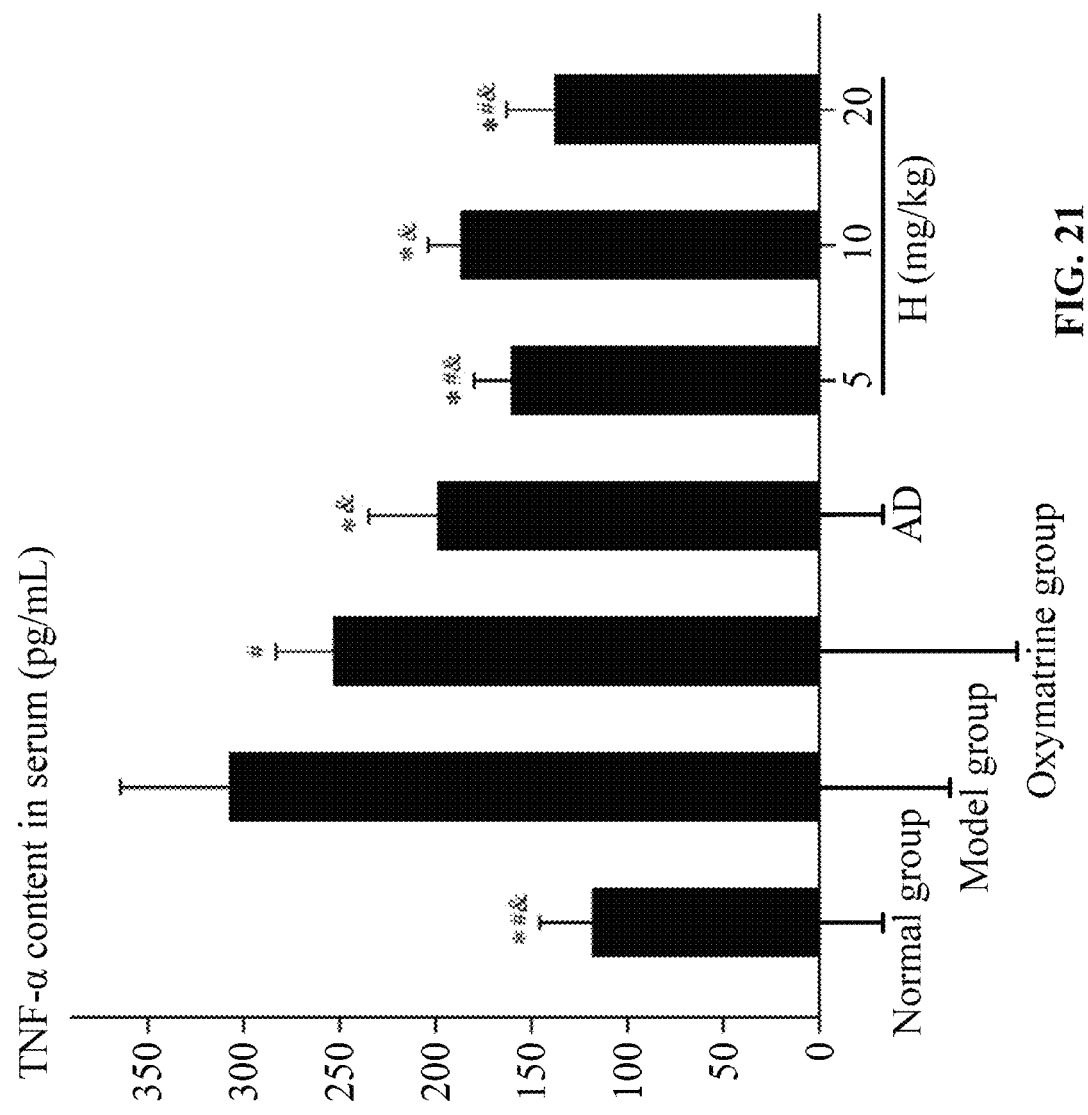
FIG. 21 is a graph showing the effect of representative compound H on the level of tumor necrosis factor-α (TNF-α) in serum of SD rats with liver fibrosis induced by CCl$_4$; compared with the model group, *P<0.05; compared with the AD group, #P<0.05; compared with the oxymatrine group, &P<0.05.

The level of IL-6 and TNF-α in the serum of the animal was determined by ELISA using the compound H of the disclosure as a representative, the results were shown in FIGS. 20 and 21. Data were processed and analyzed using SPSS 17.0 statistical software. Data were expressed as mean±standard deviation ($\overline{X}\pm S$); There were significant differences between groups when $P<0.05$.

2. Experimental Results

The results of FIGS. 20 and 21 showed that three doses of compound H significantly reduced the levels of TNF-α and IL-6 in the serum of rats with hepatic fibrosis, while the effect of the high dose group was the most significant. The levels of IL-6 and TNF-α in the serum at the dose of 20 mg/kg were comparable to those in the normal group. The results suggest that the anti-liver fibrosis effect of the compound of the disclosure was closely related to the inhibition of the expression of TNF-α and IL-6, and the inflammatory reaction was inhibited by decreasing the contents of TNF-α and IL-6.

Example 7

Effects of the Compounds of the Disclosure on the Levels of SOD and MDA in Liver Tissues of SD Rats Induced by Carbon Tetrachloride ($CCl_4$)

SOD and MDA are important indicators for evaluating lipid peroxidation. SOD is an antioxidant that inhibits lipid peroxidation caused by free radical initiation, and also scavenges free radicals to protect the integrity of biofilms, and is a sensitive indicator of antioxidant capacity in the body. Lipid peroxidation produces a large amount of MDA, which is proportional to the degree of peroxidative damage to tissues.

1 Materials and Methods

The same as Example 2.

Figure 22:
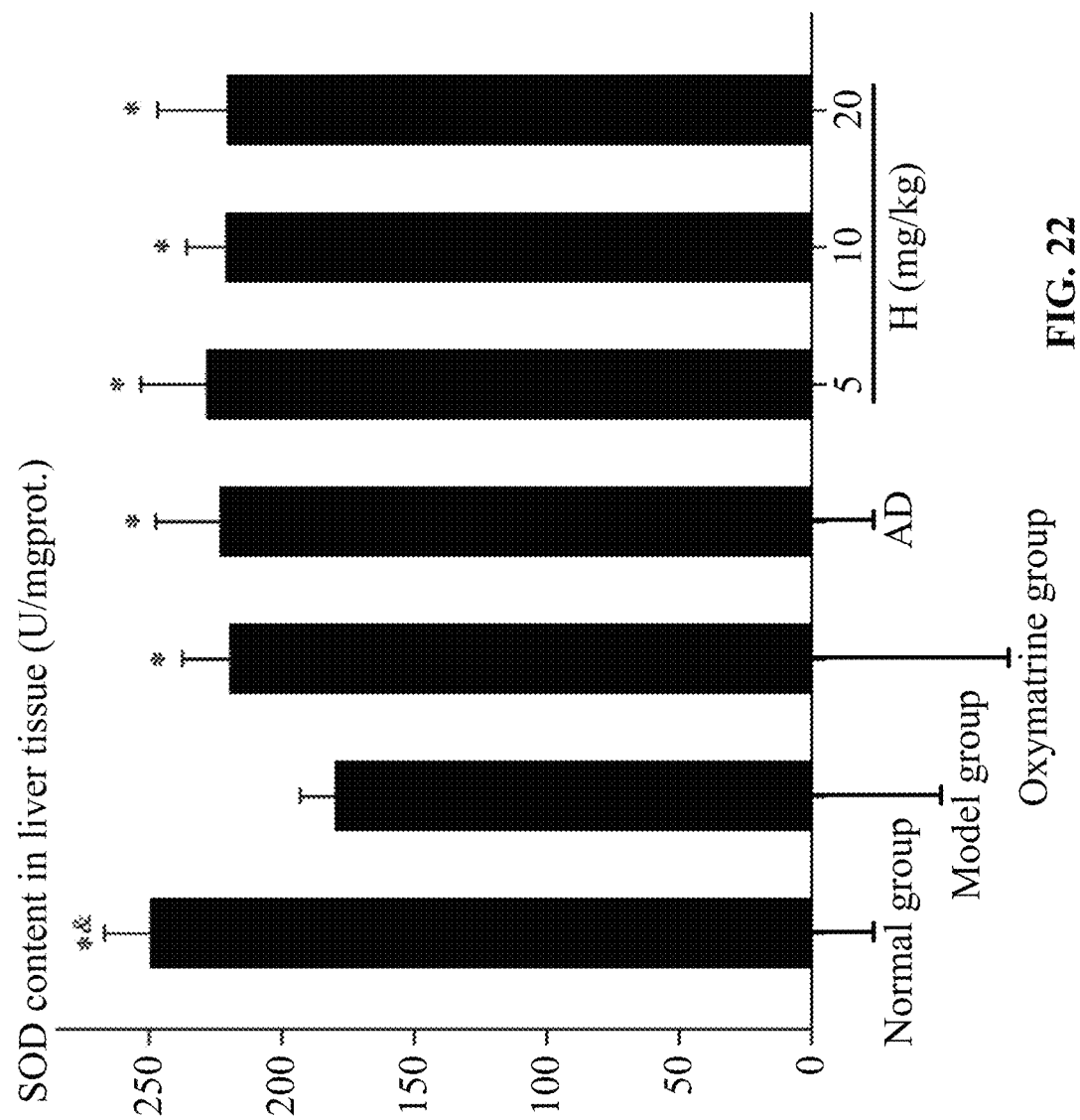
FIG. 22 is a graph showing the effect of representative compound H on the level of superoxide dismutase (SOD) in liver tissue of SD rats with liver fibrosis induced by CCl$_4$; compared with the model group, *P<0.05.
Figure 23:
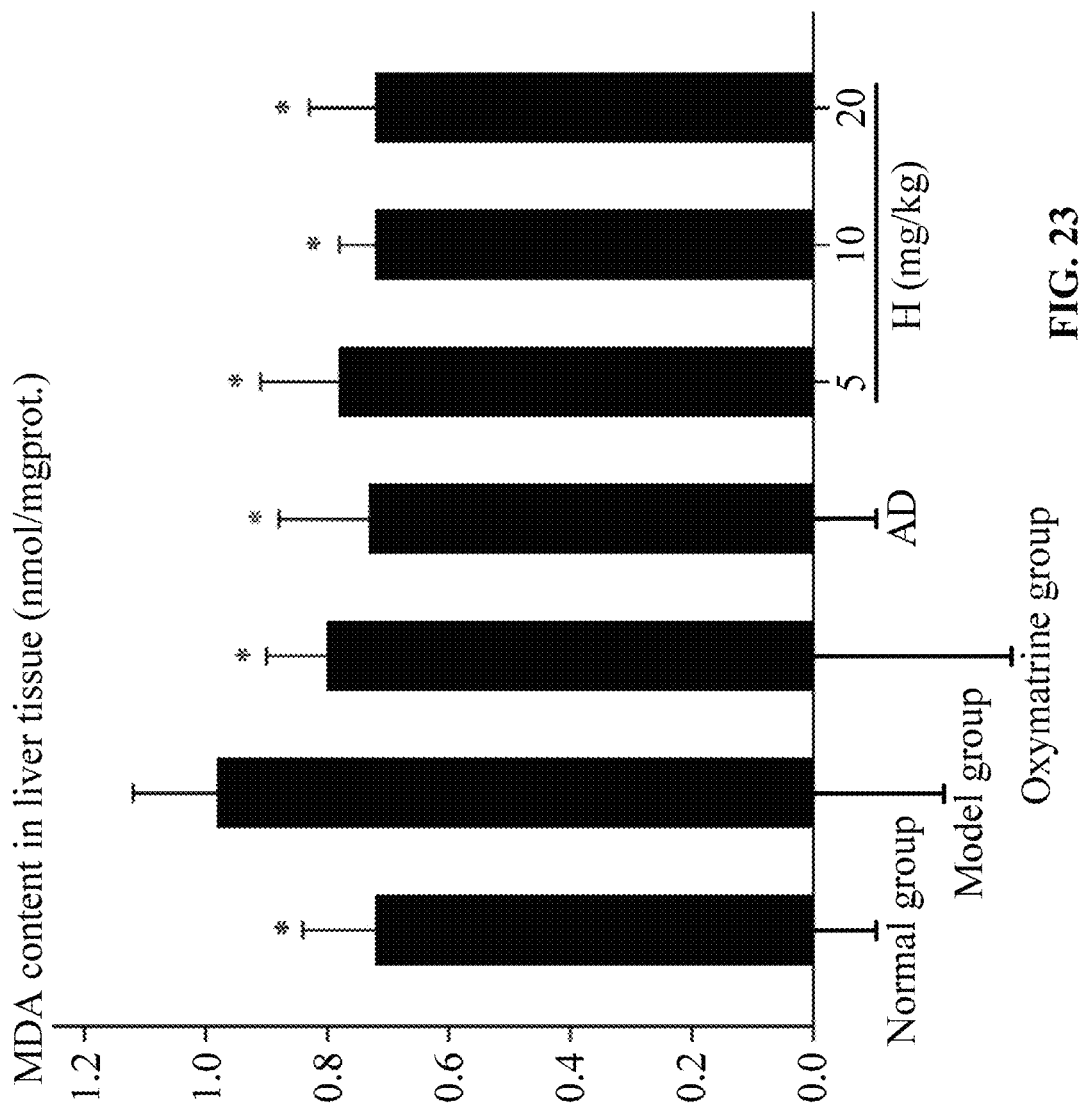
FIG. 23 is a graph showing the effect of representative compound H on the level of malondialdehyde (MDA) in liver tissue of SD rats with liver fibrosis induced by CCl$_4$; compared with the model group, *P<0.05.

The level of SOD and MDA in the liver tissue of the animal was determined by the compound H of the disclosure, the results were shown in FIGS. 22 and 23. Data were processed and analyzed using SPSS 17.0 statistical software. Data were expressed as mean±standard deviation ($\overline{X}\pm S$); There were significant differences between groups when $P<0.05$.

2. Experimental Results

The results of FIGS. 22, and 23 showed that the SOD levels of the 5, 10, and 20 mg/kg doses groups of the disclosure significantly increased and were close to normal levels. The MDA levels of the 10 and 20 mg/kg doses groups were significantly reduced and close to normal values, indicating that the compound of the disclosure retain the strong anti-lipid peroxidation activity of AD.

Example 8

Compound of the Disclosure Significantly Improved the Inflammatory State of Liver Tissue in SD Rats with Liver Fibrosis Induced by Carbon Tetrachloride ($CCl_4$)

1 Materials and Methods

The same as Example 2.

Figure 24:
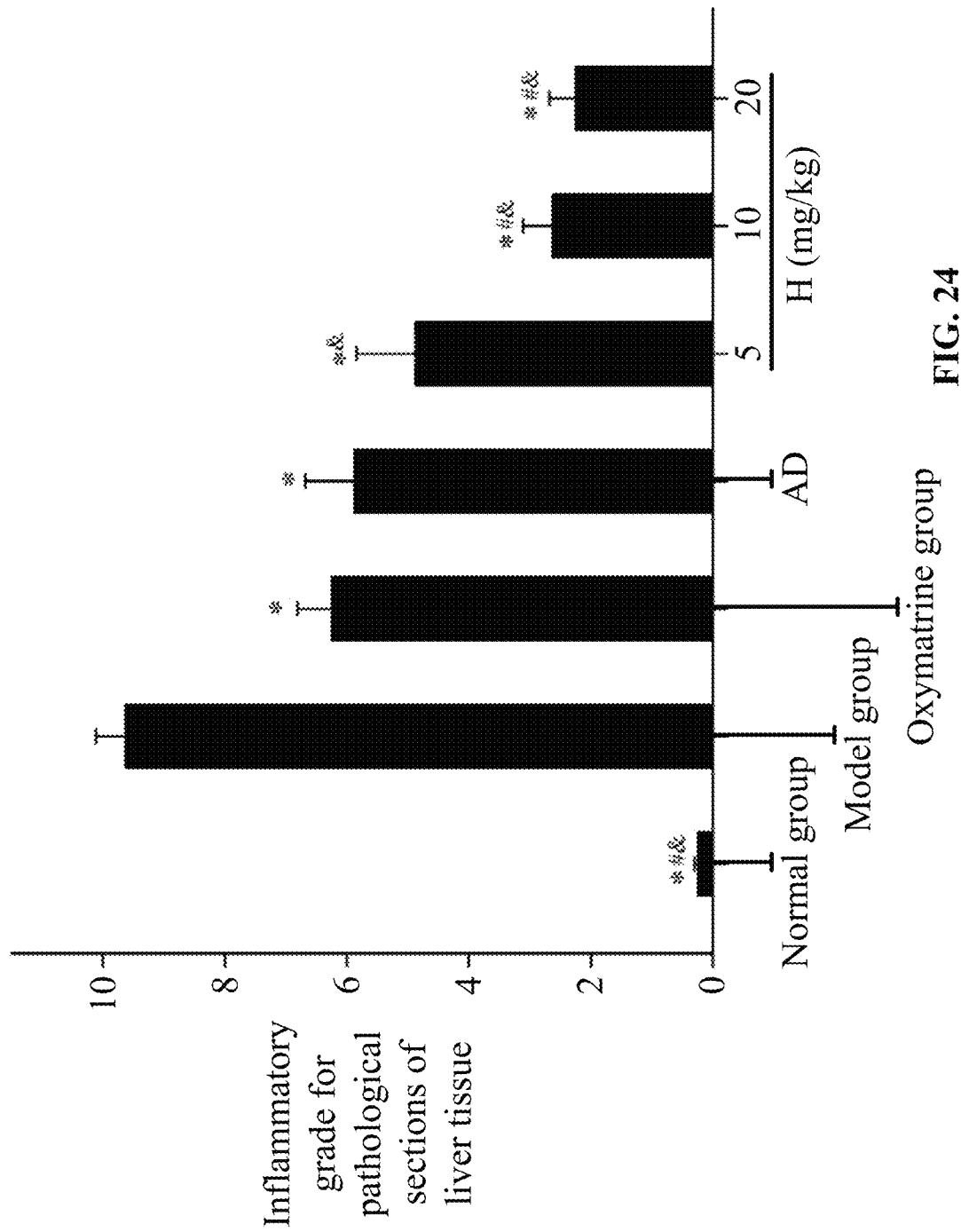
FIG. 24 is a graph showing the effect of representative compound H on the inflammatory grade for pathological sections of liver tissue in SD rats with liver fibrosis induced by CCl$_4$ (statistical results), compared with the model group, *P<0.05; compared with the AD group, #P<0.05; compared with the oxymatrine group, &P<0.05.
Figure 25:
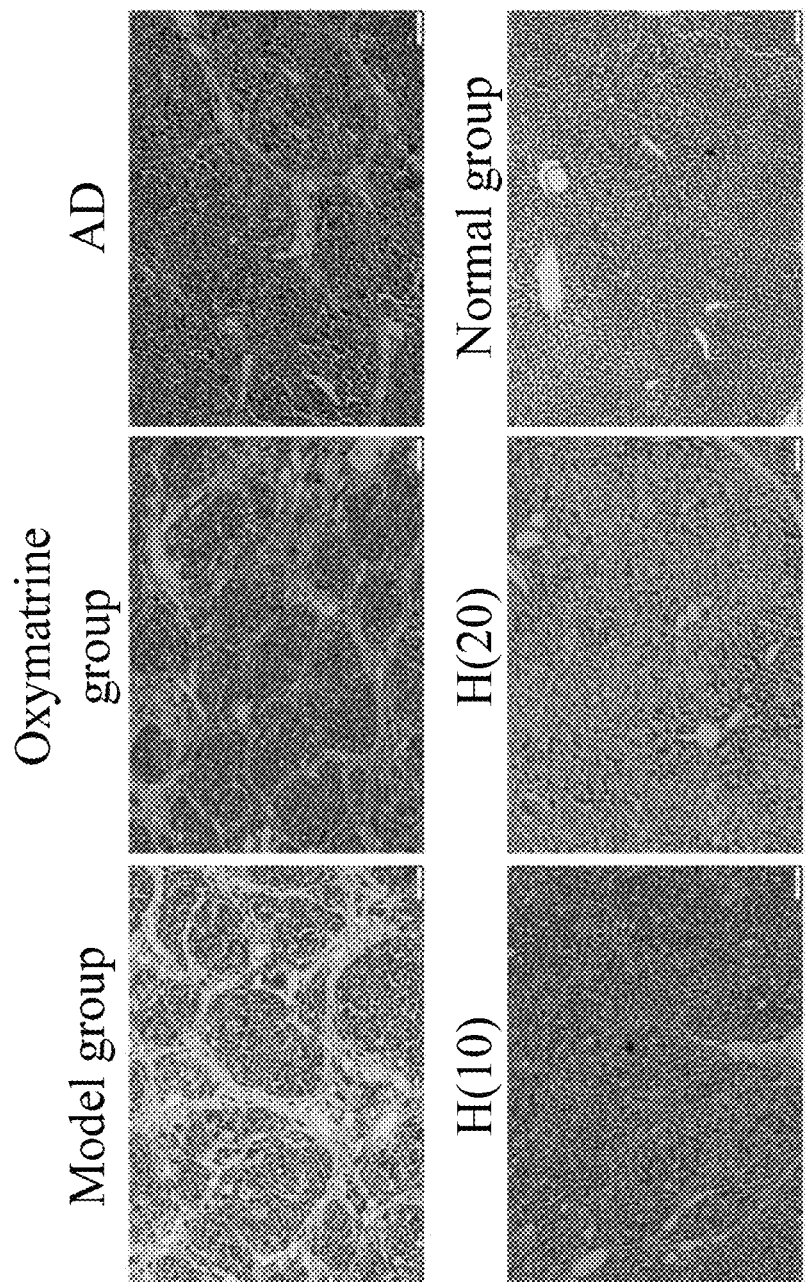
FIG. 25 is a graph showing the effect of representative compound H on the inflammatory grade for pathological sections of liver tissue in SD rats with liver fibrosis induced by CCl$_4$ (H&E staining; ×100 times)

The compound H of the disclosure was selected as a representative, and H&E staining was used to observe the improvement of the immune inflammatory state of the liver tissue by the compound H, and the results were shown in FIGS. 24 and 25. Data were processed and analyzed using SPSS 17.0 statistical software. Data were expressed as mean±standard deviation ($\bar{X}\pm S$); There were significant differences between groups when $P<0.05$.

2. Experimental Results

The results of FIGS. 24, and 25 showed that the structure of liver lobule of the normal group was intact, the hepatic cords were arranged in neat order, no abnormal changes occurred, and the vascular area was normal. Hepatocytes showed no deformation, necrosis, or formation of fibrous connective tissue. Rats in the model group showed chaotically arranged hepatic cell cords, a significantly increased nuclear-to-plasma ratio, accompanied by some visible, flaky and focal necrotic areas, severe lymphocytic infiltration, and severe damage to the structure of hepatic lobule. The liver injury of the animals in the drug-administered groups was improved to some extent compared with the model group. In particular, the compound H of the disclosure was most prominent in the middle and high-dose groups, the hepatocytes were only slightly enlarged, and the structure of the hepatic cell cord was normal, which was significantly better than the positive drug oxymatrine treatment group and the AD treatment group.

Example 9

Compounds of the Disclosure Inhibits TGF-β1-Induced Conversion of Human Alveolar Type II A549 Cells to Mesenchymal Cells Type II alveolar epithelial cells present in the alveoli are stimulated by cytokines such as inflammatory mediators and growth factors. The cell morphology changes from cobblestone to fusiform, completing epithelial mesenchymal transition (EMT) and functioning as an interstitial cell. Collagen fibers are further synthesized, but a large amount of collagen fiber deposition can aggravate the course and severity of interstitial pulmonary fibrosis.

1. Cell Culture and Drug Treatment

The human hepatic stellate A549 cell (provided by Beijing Beina Chuanglian Biotechnology Institute) was compared with andrographolide (AD) to determine the antifibrosis effect of the compound of the disclosure in vitro. A549 cells were cultured in RPMI1640 medium containing 10% (V/V) fetal bovine serum, 100 μg/mL streptomycin, and 100 IU/mL penicillin respectively, and then were incubated in an incubator at 37° C. and 5% $CO_2$, humidified atmosphere.

2. MTT Assay for Assessment of Cytotoxicity

A549 cells in logarithmic growth phase were digested with 0.25% (w/v) trypsin, and diluted into $2.5\times10^4$/mL cell suspension with RPMI1640 medium containing 10% (v/v) fetal bovine serum. After each 96-well plate was filled with 200 μL cell suspension, the plates were placed in an incubator at 37° C. and 5% $CO_2$ for 24 h. The medium containing different concentrations of the drug was added, and the maximum final concentrations of the drugs were 30.00 μM, and each treatment was repeated in 4 wells. Following 48 h of incubation, other steps were the same as in the Example 1. The results were averaged, as shown in FIGS. 26A and 26B.

3. Morphological Observation Method to Detect the Effect of Drugs on EMT of A549 Cells A549 cells in logarithmic growth phase were digested with 0.25% (w/v) trypsin, and diluted into $2.5\times10^4$/mL cell suspension with RPMI1640 medium containing 10% (v/v) fetal bovine serum. After each 96-well plate was filled with 200 μL cell suspension, the plates were placed in an incubator for 24 h in order to complete the cell fusion. The original medium was discarded, and the medium without serum was added and re-synchronized for 24 h in order to streaking, and the cells were washed twice with PBS. Following the aspiration of 200 μL of medium containing the TGF-β1 (5 ng/mL), photographs were taken under a microscope. 3 wells were repeated for each treatment and control group was set up. Following 48 h of incubation, the cells were photographed and measured under a microscope. A total of 5 fields were selected from the three wells treated at the same concentration for each compound, and more than 100 cells were measured. The photos were processed using photoshop CS6 software and the circularity was calculated (Formula e=4π×S/C2, where e represents circularity, S represents area, and C represents perimeter). The results were averaged, as shown in FIGS. 27A and 27B.

4. Experimental Results

Figure 26A:
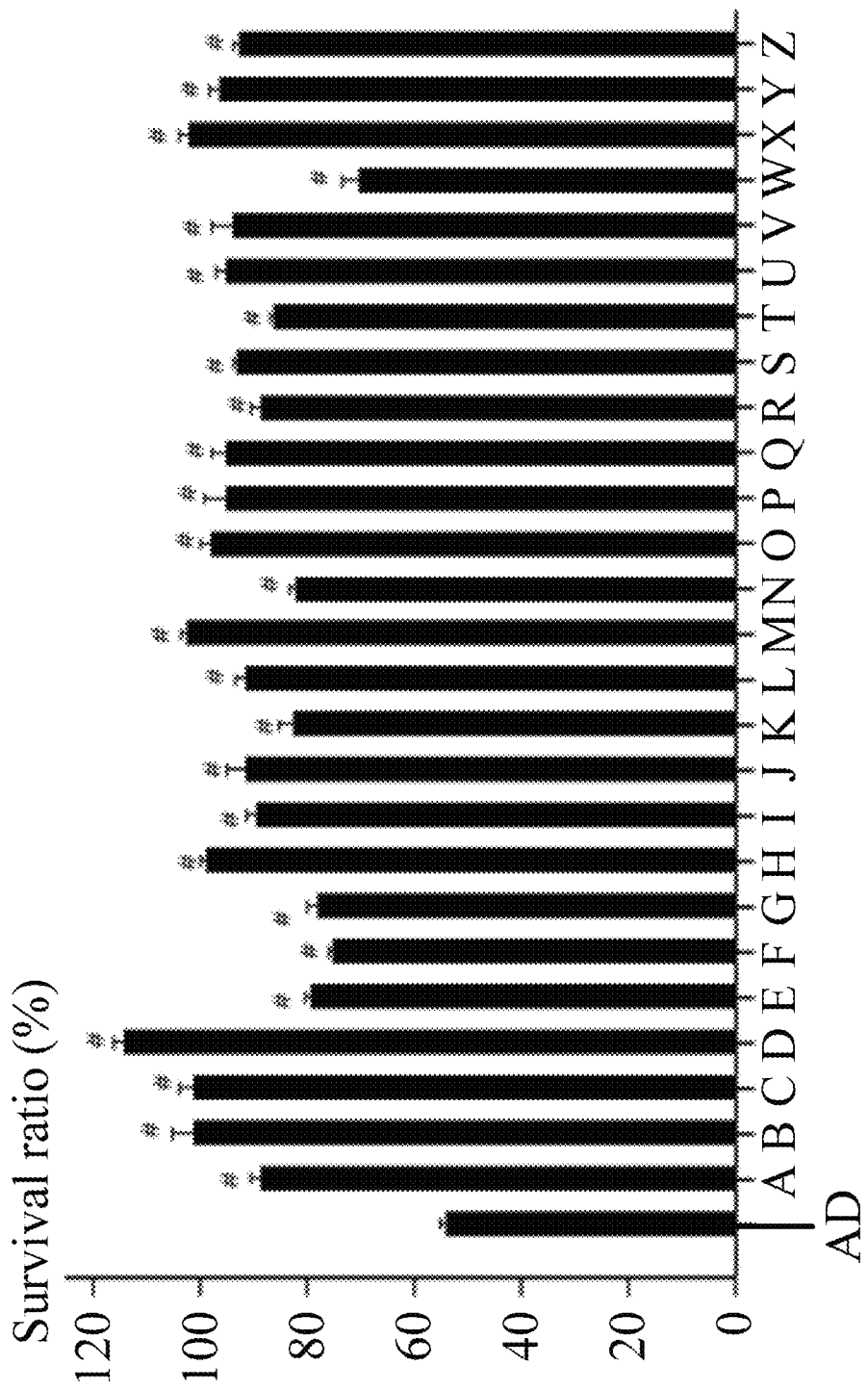
FIG. 26A shows the effect of AD and the compounds (30.00 μM) of the disclosure on the activity of human alveolar type II epithelial A549 cells; compared with the AD group, #P<0.05.
Figure 26B:
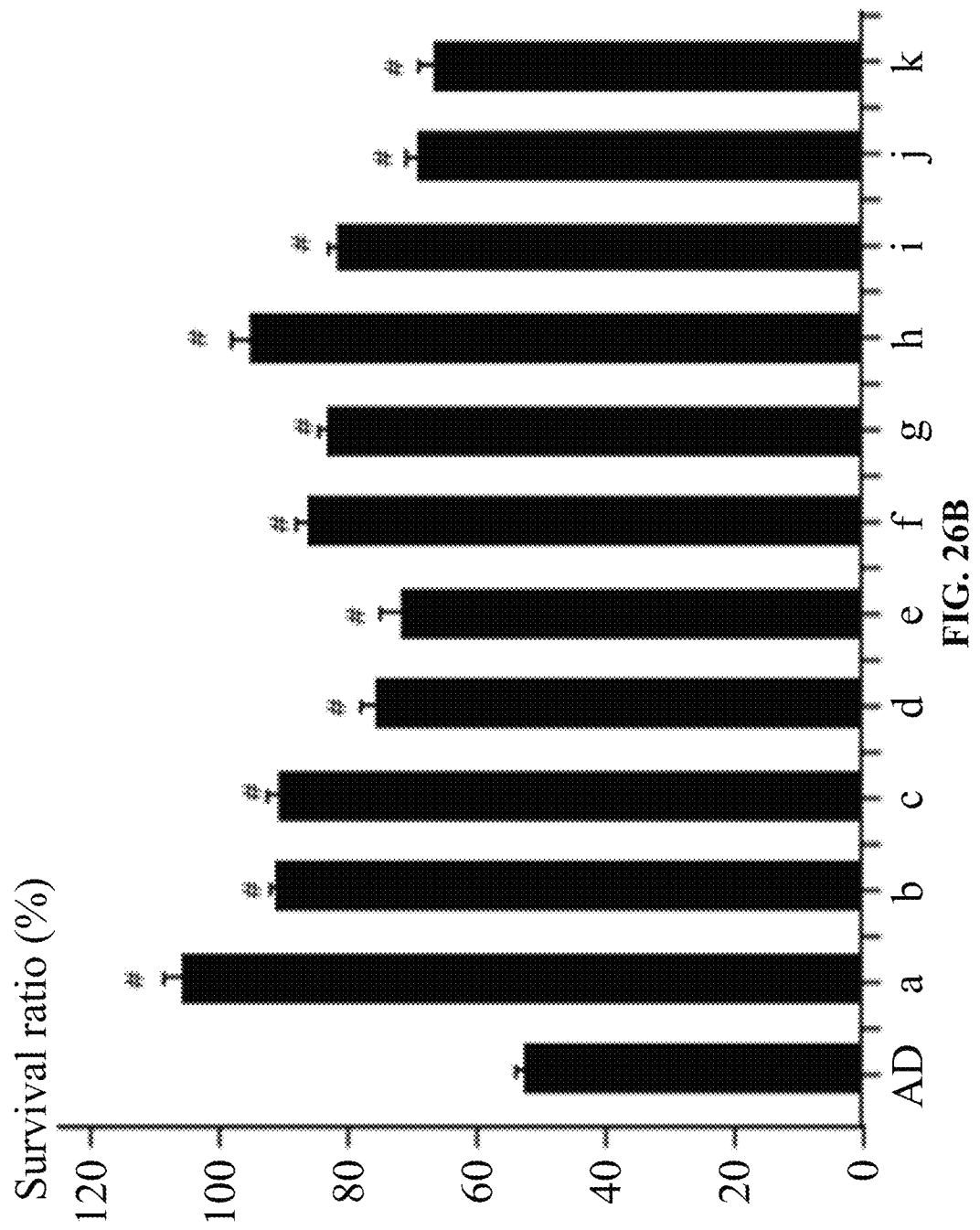
FIG. 26B shows the effect of AD and the compounds of the disclosure on the activity of human alveolar type II epithelial A549 cells. In the figure, the test concentrations of f, g, h, and k are 3.00 μM, and the rest are 30.00 μM, compared with the AD group, #P<0.05.

The results of FIGS. 26A and 26B showed that the cytotoxic activity of the compounds of the disclosure against A549 cells was not enhanced at a concentration of 30.00 μM (except for f, g, h, k of 3.00 μM) compared to AD.

Figure 27A:
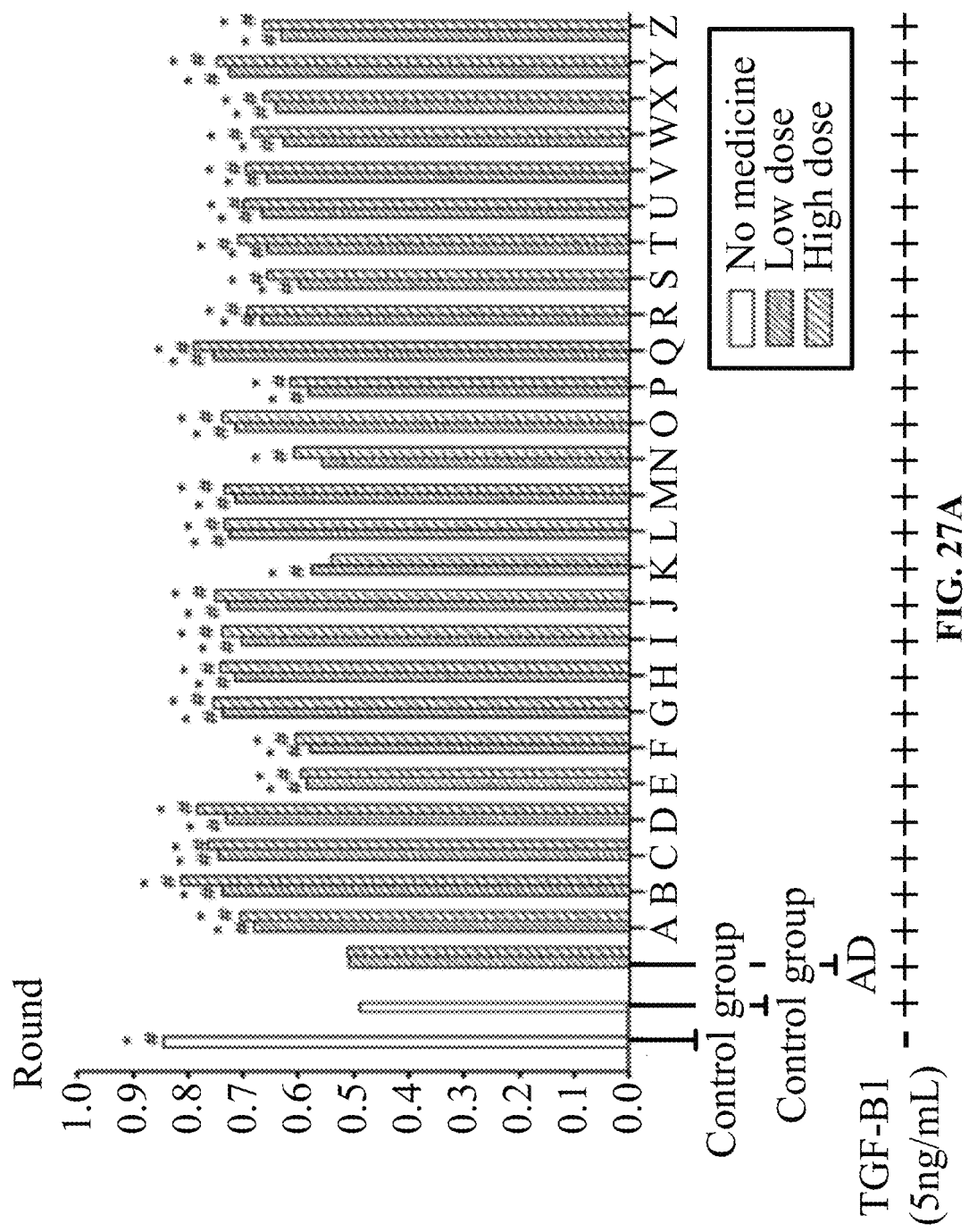
FIG. 27A shows the inhibition of TGF-β1-induced conversion of human alveolar type II A549 cells to mesenchymal cells (statistical results). The low and high concentrations of the compounds AD, N, P, Q, S—W and Z were 0.63 μM and 1.25 μM respectively; the low and high concentrations of compounds C, E-G, I-L, O, R, X and Y are 0.31 μM and 0.63 μM respectively; the low and high concentrations of compounds A, B, D, H and M are 0.16 μM and 0.31 μM respectively; compared with the TGF-β1 control group, #P<0.05; compared with the AD control group, *P<0.05.
Figure 27B:
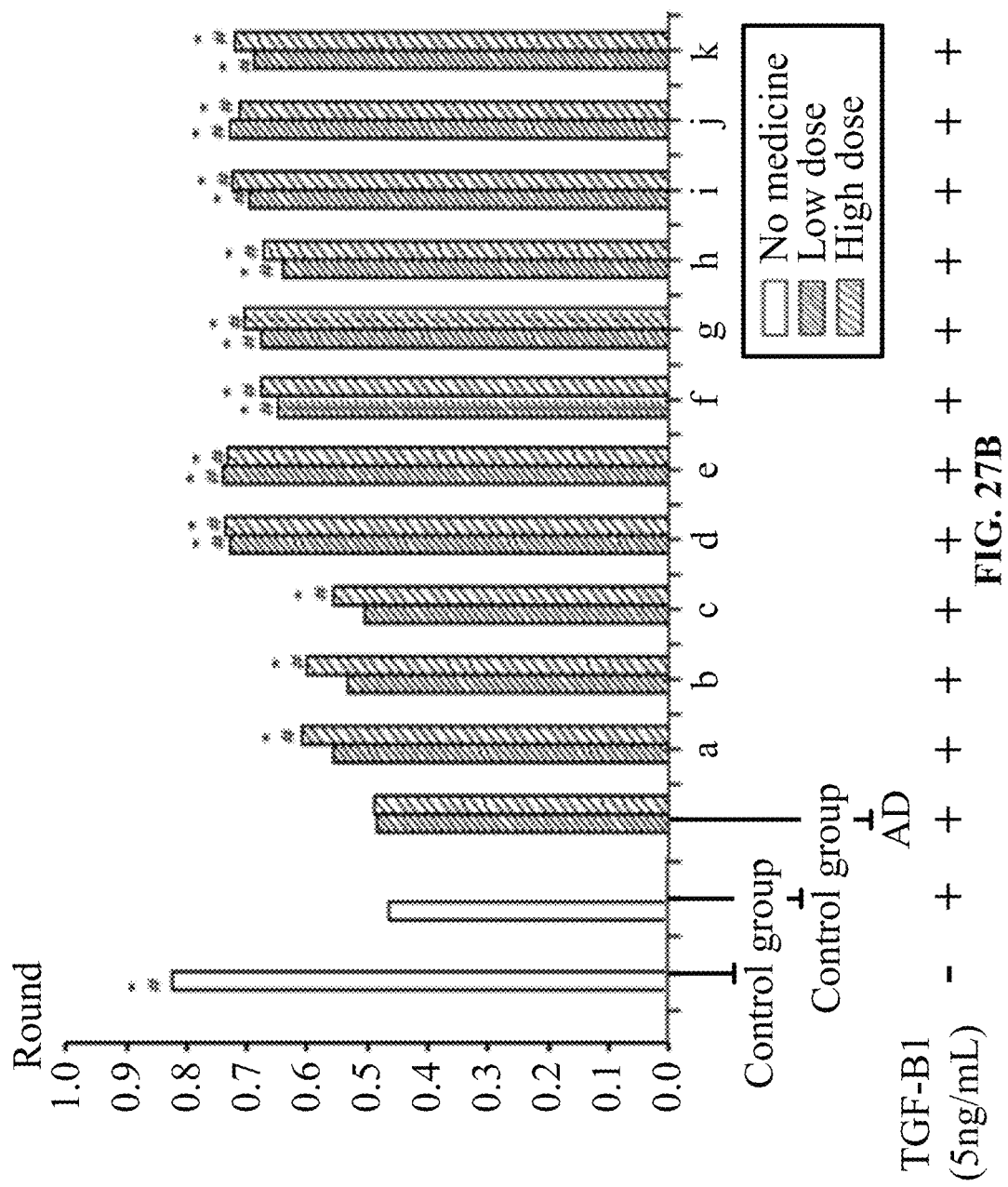
FIG. 27B shows that AD and compounds represented by the disclosure inhibit TGF-β1-induced conversion of human alveolar type II A549 cells to mesenchymal cells (statistical results). The low and high concentrations of the compounds AD-d, f, g are 0.63 μM and 1.25 μM respectively; the low and high concentrations of e, h-k are 0.31 μM and 0.63 μM respectively; compared with the TGF-β1 control group, #P<0.05; compared with the AD control group, *P<0.05.

FIGS. 27A and 27B showed that the compound of the disclosure could significantly inhibit the epithelial-mesenchymal transition of A549 cells at a non-toxic concentration, and has a stronger inhibitory effect on the mesenchymal transition of human type II alveolar epithelial cells compared to AD, and the safety index was higher.

Example 10

The Compounds of the Disclosure Reduce the Degree of Pulmonary Fibrosis Induced by Bleomycin in KM Mice Pulmonary fibrosis is a lung injury caused by a variety of reasons, illustrating that the pathogenesis of pulmonary fibrosis is very complicated. Different pathogenic factors stimulate inflammation and immune response, involving a variety of cells including vascular endothelial cells, alveolar epithelial cells, fibroblasts and macrophages, and the interaction of various cytokines and inflammatory mediators.

1 Materials and Methods

1) Experimental Animals

SPF grade KM mice, healthy, male, body weigh 20±2 g, were purchased from Experimental Animal Center of Henan Province. (License No. SCXK (Yu) 2015-0004).

2) Drugs, Reagents and their Preparation

Bleomycin hydrochloride injection was produced by Hisun-Pfizer Pharmaceuticals Co., Ltd. (Batch No.: YBH15562005, SDA License No.: GUOYAOZHUNZI 20055883). Prednisone acetate tablets was produced by Zhejiang Xianyi Pharmaceutical Co., Ltd. (Batch No.:

170410, SDA License No.: GUOYAOZHUNZI 33021207). Other test drugs and compounds were the same as in Example 2, and the drugs were formulated as a 0.5% sodium carboxymethylcellulose (CMC-Na) suspension.

3) Experimental Method

After KM mice were fed ad libitum for 3 days, they were weighed individually and were randomly divided into six groups including a sham-operated control group, a model group, a prednisone control group (5 mg/kg), an AD group (250 mg/kg) and two compound H groups (62.5 mg/kg and 250. mg/kg), fifteen mice per group. The mice were anesthetized with intraperitoneal injection of 4% sodium pentobarbital (2 ml/kg). After the immobilization in a supine position, the anesthetized mice were prepared. The necks of the mice were shaved and then swabbed with iodine to sterilize the skin regions. An incision with a length of about 1 cm was made along the neck for separating bronchus. After the injection of bleomycin (2 mg/mL) of 50 μL, 150 μL of air was immediately injected. The mice were quickly rotated to evenly distribute the drug solution. The incision was sutured with 4/0 silk thread. The wound was subsequently swabbed with iodine, and the mice rest in a 37° C. warming environment until the animals were fully awake. The sham operation group was injected with the same volume of physiological saline. After 24 h of modeling, the mice were administered by gavage at the same time. The administration method was the same as in Example 2, and the experiment was over after 28 days of administration. The bedding of the mice should be replaced at the first 12 hours of the last gavage, strictly fasting with nothing but water. After administration for 1.5 h, the whole blood from the eyeball was collected. Use of cervical dislocation to euthanize the mice. The lungs of the mice were fixed in 4% paraformaldehyde fixative after photographing. Serum preparation, Masson's trichrome staining and statistical methods of results were the same as in Example 2, Masson's trichrome staining and relative collagen area results were shown in FIGS. 28 and 29.

2. Experimental Results

Figure 28:
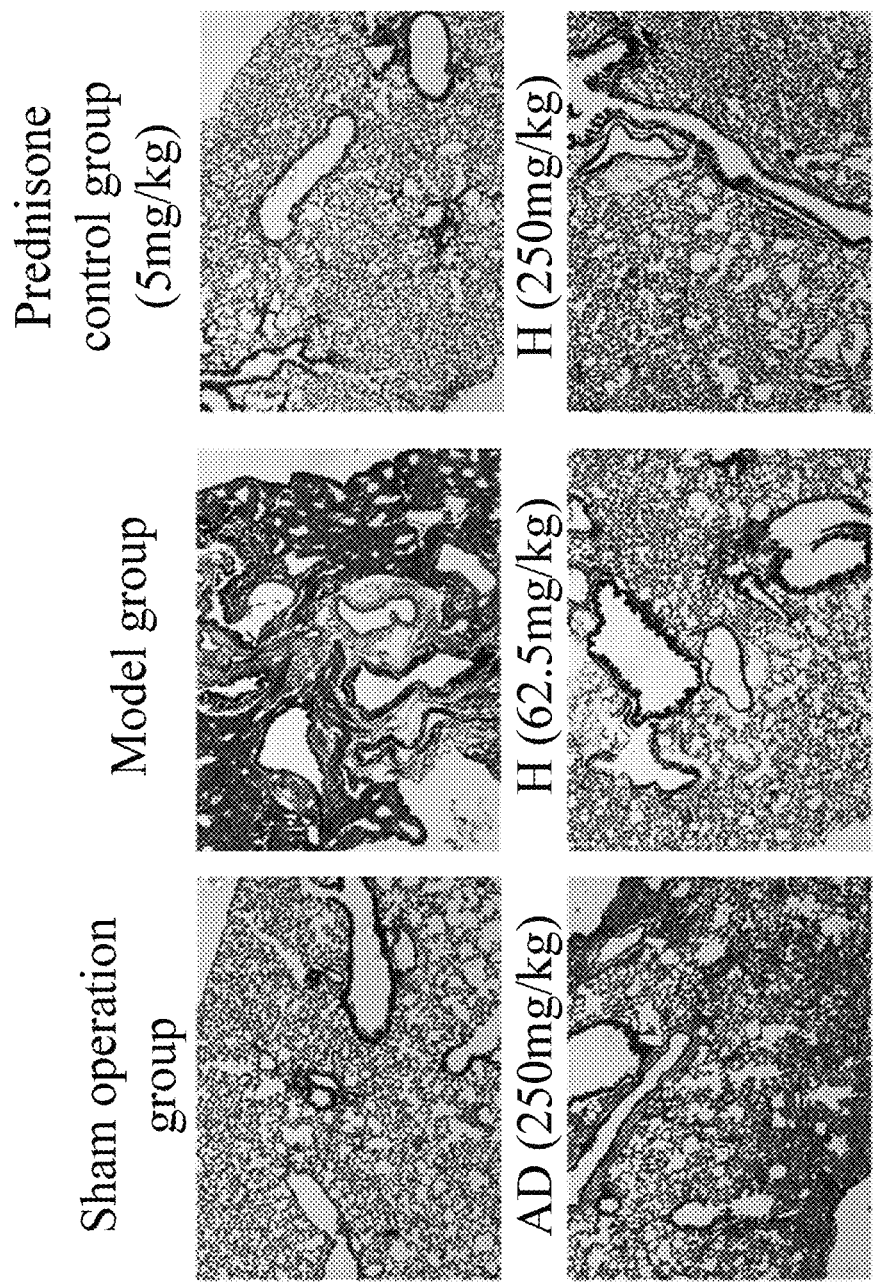
FIG. 28 is a graph showing the effect of representative compound H of the disclosure on the degree of bleomycin-induced pulmonary fibrosis in KM mice (partial tissue of Masson's trichrome staining; ×100 times)
Figure 29:
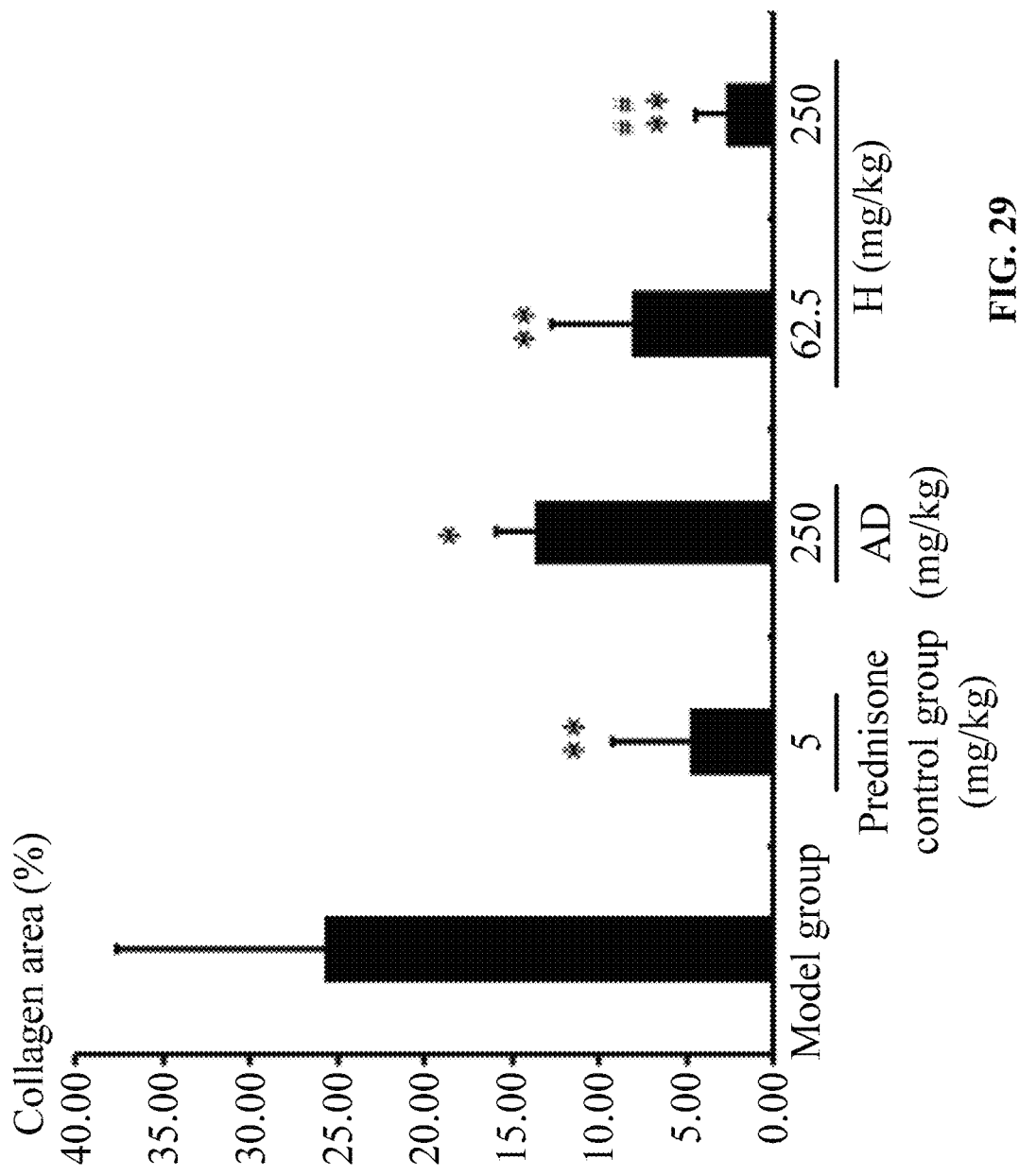
FIG. 29 is a graph showing the effect of representative compound H on the degree of bleomycin-induced pulmonary fibrosis in KM mice (collagen area/%); compared with the model group, *P<0.05, **P<0.01; compared with the AD group, ##P<0.01.

The results of FIGS. 28 and 29 showed that for the bleomycin-induced mice pulmonary fibrosis model, the compound H of the disclosure significantly reduced the fibrotic area of lung tissue of the KM mice, and the effect was significantly stronger than AD.

Example 11

The Compound of the Disclosure Significantly Improves the Inflammatory State of Lung Tissue in Bleomycin-Induced Pulmonary Fibrosis in KM Mice 1 Materials and Methods The same as Example 10.

Figure 30:
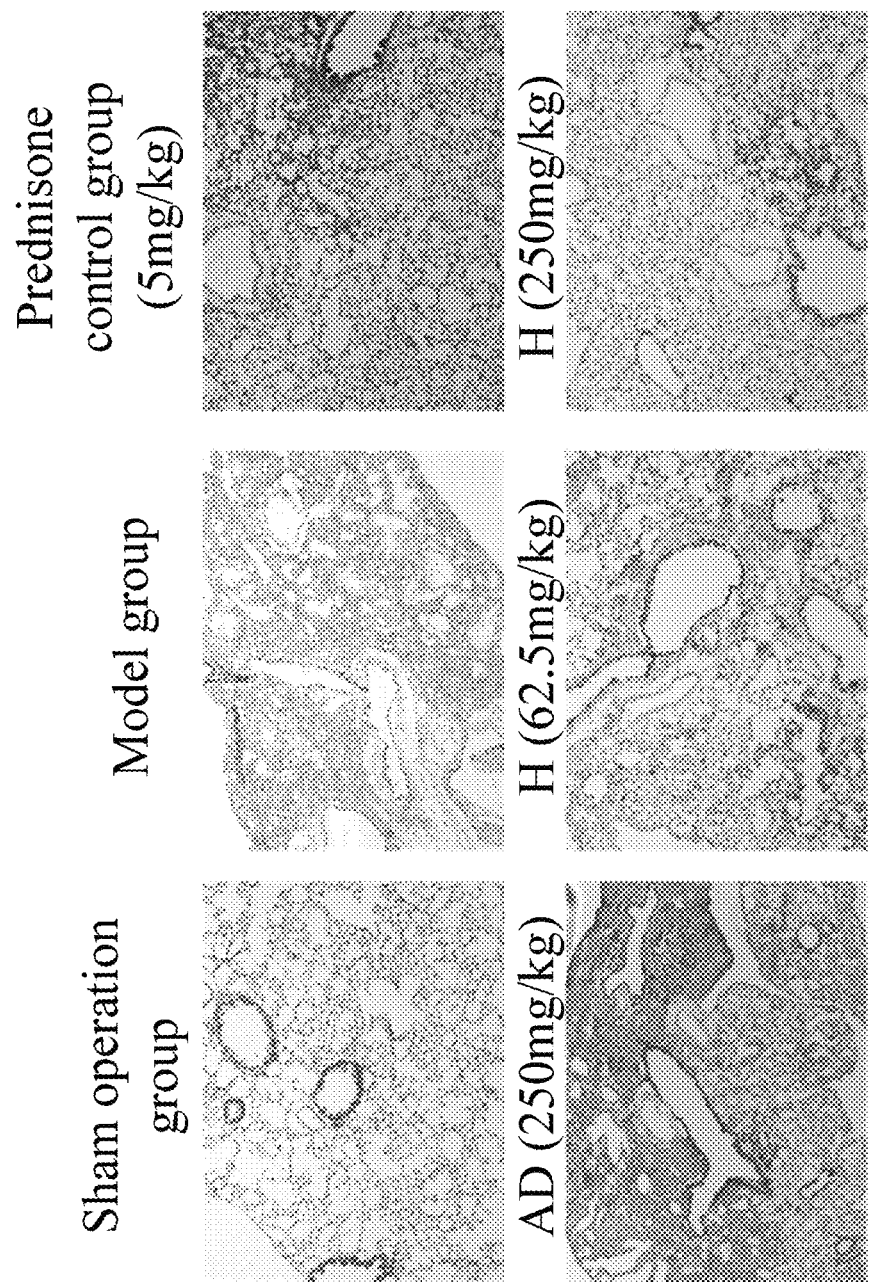
FIG. 30 is a graph showing the effect of compound H on the inflammatory grade for pathological sections of lung tissue in KM mice induced by bleomycin (H&E staining; ×100 times)
Figure 31:
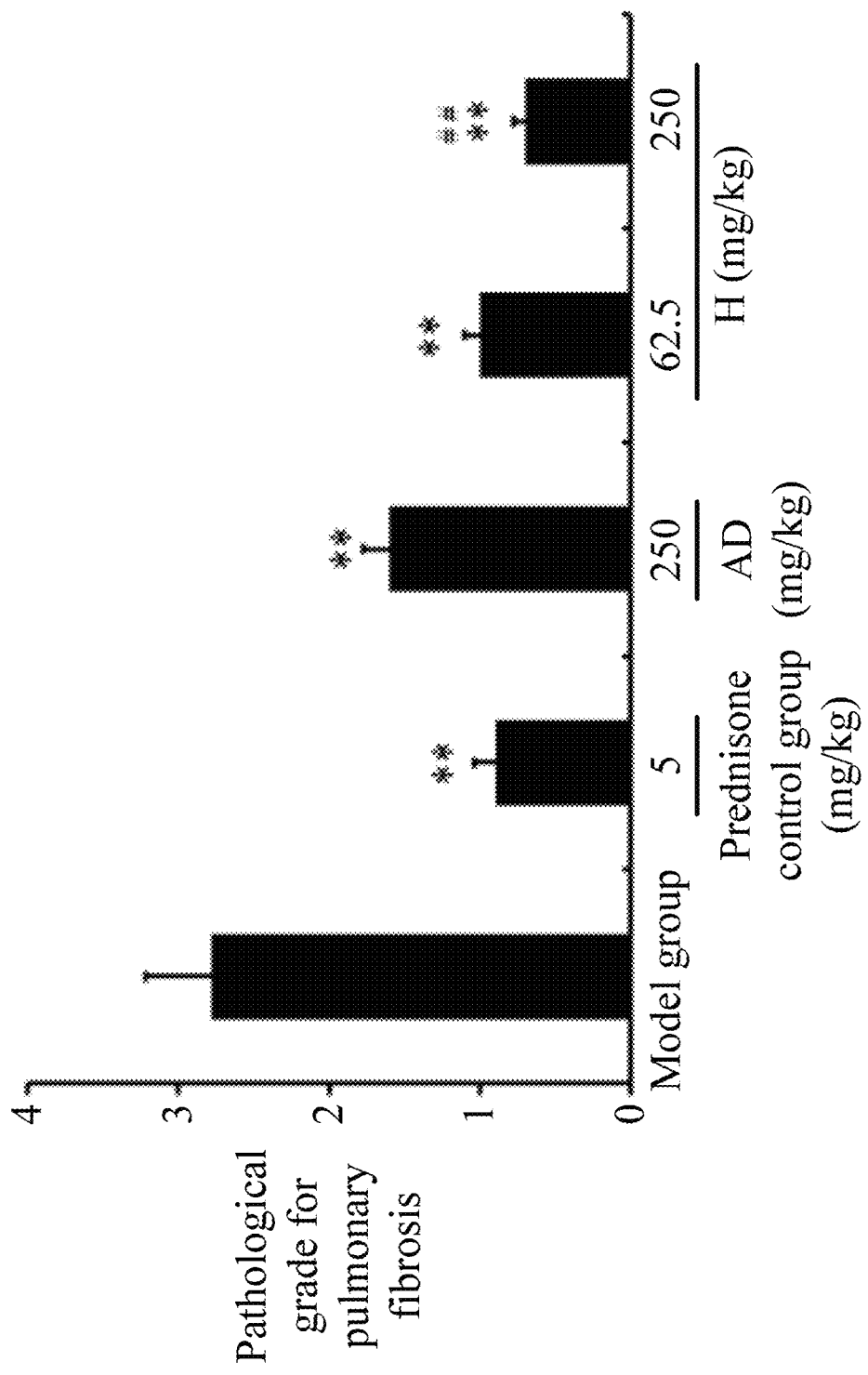
FIG. 31 is a graph showing the effect of compound H on the inflammatory grade for pathological sections of lung tissue in KM mice induced by bleomycin (statistical results), compared with the model group, **P<0.01; compared with the AD group, ##P<0.01. Note: Pathological grading criteria used for pulmonary fibrosis: 0=without alveolitis; 1=areas of alveolitis is less than 1/5; 2=areas of alveolitis is above 1/5, 1/2 or more; 3=areas of alveolitis is 1/2 or more.

The compound H of the disclosure was selected as a representative, and H&E staining was used to observe the improvement of the inflammatory state of the lung tissue by the compound H, and the staining results and pathological scores were shown in FIGS. 30 and 31. Data were processed and analyzed using SPSS 17.0 statistical software. Data were expressed as mean±standard deviation ($\bar{X}$±S); There were significant differences between groups when $P<0.05$.

2. Experimental Results

The results of FIGS. 30 and 31 showed that in the sham operated group, the structure of lung tissue was intact, the lung interval was uniform, no abnormal changes occurred, and no inflammatory cell infiltration that was visible to the naked eye. But the alveolar structure of mice in the model group was disordered, the lung interval became thicker, and the pulmonary interstitial fibrosis material segmented the alveoli to form reconstructed alveoli, and a large number of inflammatory cells infiltrated. Compared with the model group, the lung tissue damage of the animals in the drug-administered group was improved to some extent, especially in the high-dose treatment group of the compound H of the disclosure, the alveolar structure of the lung tissue was basically intact and normal, and inflammatory cell infiltration was difficult to identify with the naked eye, illustrating that efficacy of drug-administered group was significantly better than the AD treatment group.

Example 12

Compounds of the Disclosure Inhibits TGF-β1-Induced Conversion of Human Proximal Tubular Epithelial Cells HK-2 to Mesenchymal Cells Early studies have found that tubular epithelial cells can transdifferentiate to fibroblasts and express their fibroblast-specific protein (FSP1). Epithelial-mesenchymal transition of tubular epithelial cells is one of the important pathogenesis of renal interstitial fibrosis. Therefore, after TGF-β1 stimulation, the anti-renal fibrosis effect of the compounds of the disclosure was evaluated by morphological observation.

1. Cell Culture and Drug Treatment

Human proximal tubular epithelial cells HK-2 (provided by the China Center for Type Culture Collection) were used to study the in vitro anti-renal fibrosis effect of the compounds of the disclosure in comparison with andrographolide (AD). HK-2 cells were cultured in DMEM-F12 medium containing 10% (V/V) fetal bovine serum, 100 μg/mL streptomycin, and 100 IU/mL penicillin respectively, and then incubated in an incubator at 5% $CO_2$ and 37° C., humidified atmosphere.

2. MTT Assay for Assessment of Cytotoxicity

Figure 32A:
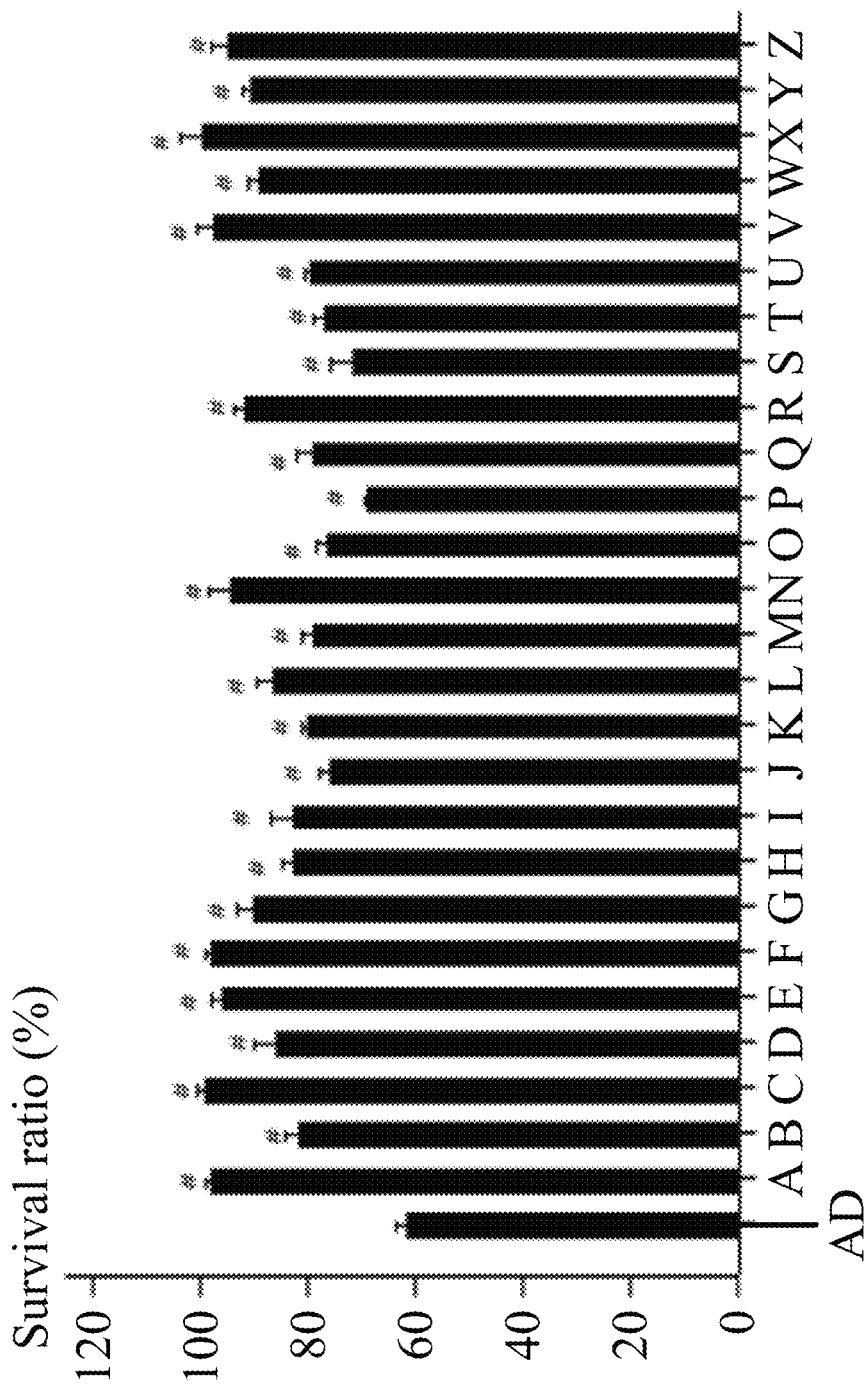
FIG. 32A shows the effect of AD and the compounds of the disclosure on the activity of human proximal tubular epithelial HK-2 cells; the compound concentration is 30.00 μM, compared with the AD group, #P<0.05.
Figure 32B:
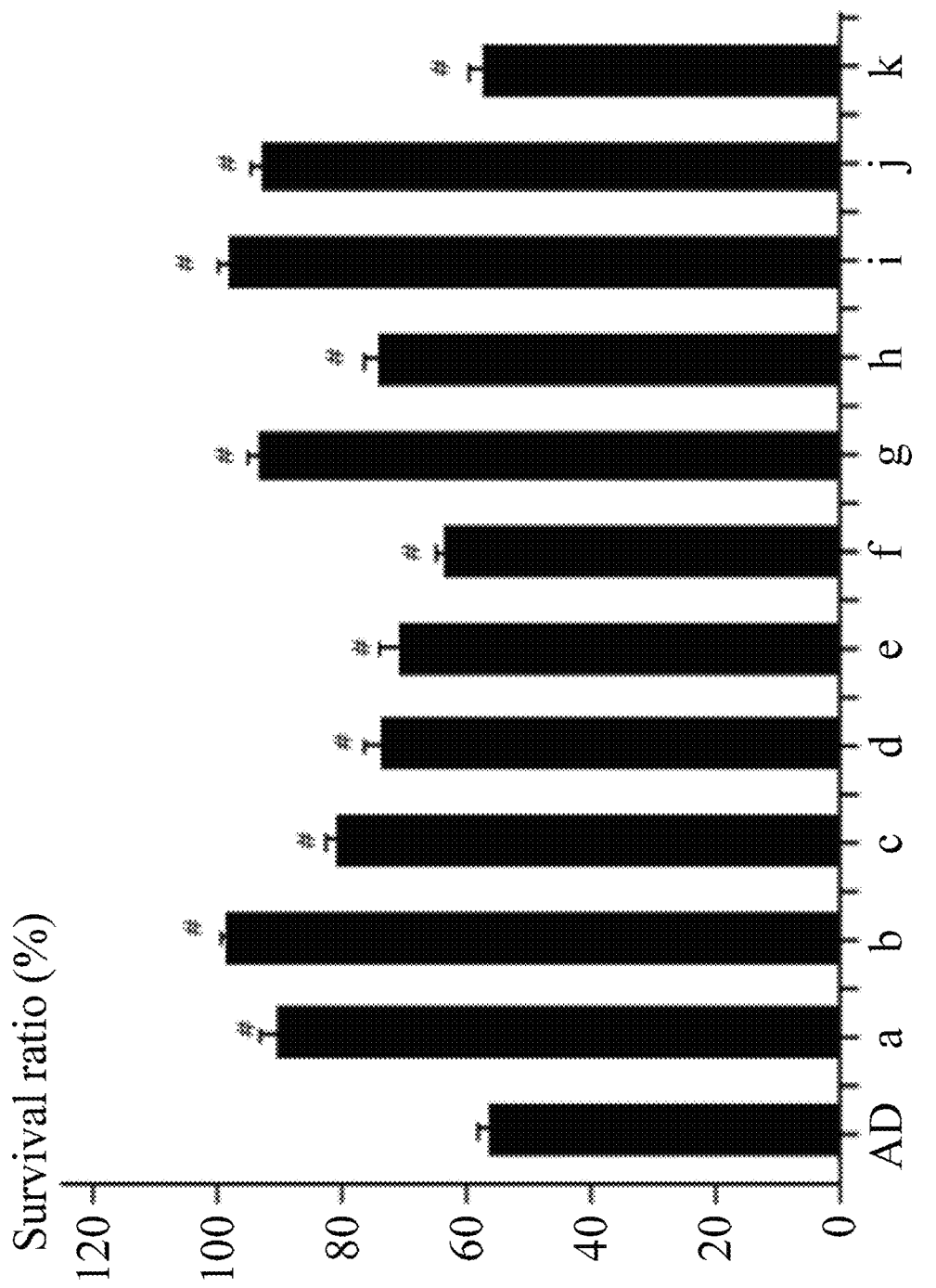
FIG. 32B is a graph showing the effect of AD and the compound of the disclosure on the activity of human proximal tubular epithelial HK-2 cells; the compound concentration is 30.00 μM; compared with the AD group, #P<0.05.

HK-2 cells in logarithmic growth phase were digested with 0.25% (w/v) trypsin and 0.02% EDTA (W/V), and diluted into $7.0×10^4$/mL cell suspension with DMEM-F12 medium containing 10% (v/v) fetal bovine serum. After each 96-well plate was filled with 200 μL cell suspension, the plates were placed in an incubator at 37° C. and 5% $CO_2$ for 24 h. The medium containing different concentrations of the drugs were added respectively, and the maximum final concentration of the drugs was 30.00 μM, and each treatment was repeated in 4 wells. Following 48 h of incubation, other steps were the same as in Example 1. The results were averaged, as shown in FIGS. 32A and 32B.

3. Effect of Drugs on the Morphology of HK-2 Cells after TGF-β1 Stimulation

HK-2 cells in logarithmic growth phase were digested with 0.25% (w/v) trypsin and 0.02% EDTA (W/V), and diluted into $5.0×10^6$/mL cell suspension with DMEM-F12 medium containing 10% (v/v) fetal bovine serum. After each 96-well plate was filled with 200 μL cell suspension, the plates were placed in an incubator for 24 h in order to generate a single layer of cells. The original medium was discarded, and the cells were washed twice with PBS, and the medium without serum was added. After 24 h of re-synchronized, 200 μL of DMEM-F12 medium containing different concentrations of the test compound and the stimulating factor TGF-β1 (5 ng/mL) was added. Each treatment was repeated in 4 wells and control group was set up. After 48 h of incubation, the cells were photographed under a microscope. The morphological changes of partial compounds of the disclosure after administration to cells were shown in FIGS. 33A and 33B.

4. Experimental Results

The results of FIGS. 32A and 32B showed that the inhibition of HK-2 cell proliferation by the compounds of the disclosure was significantly reduced at a concentration of 30.00 μM compared to AD.

Figure 33A:
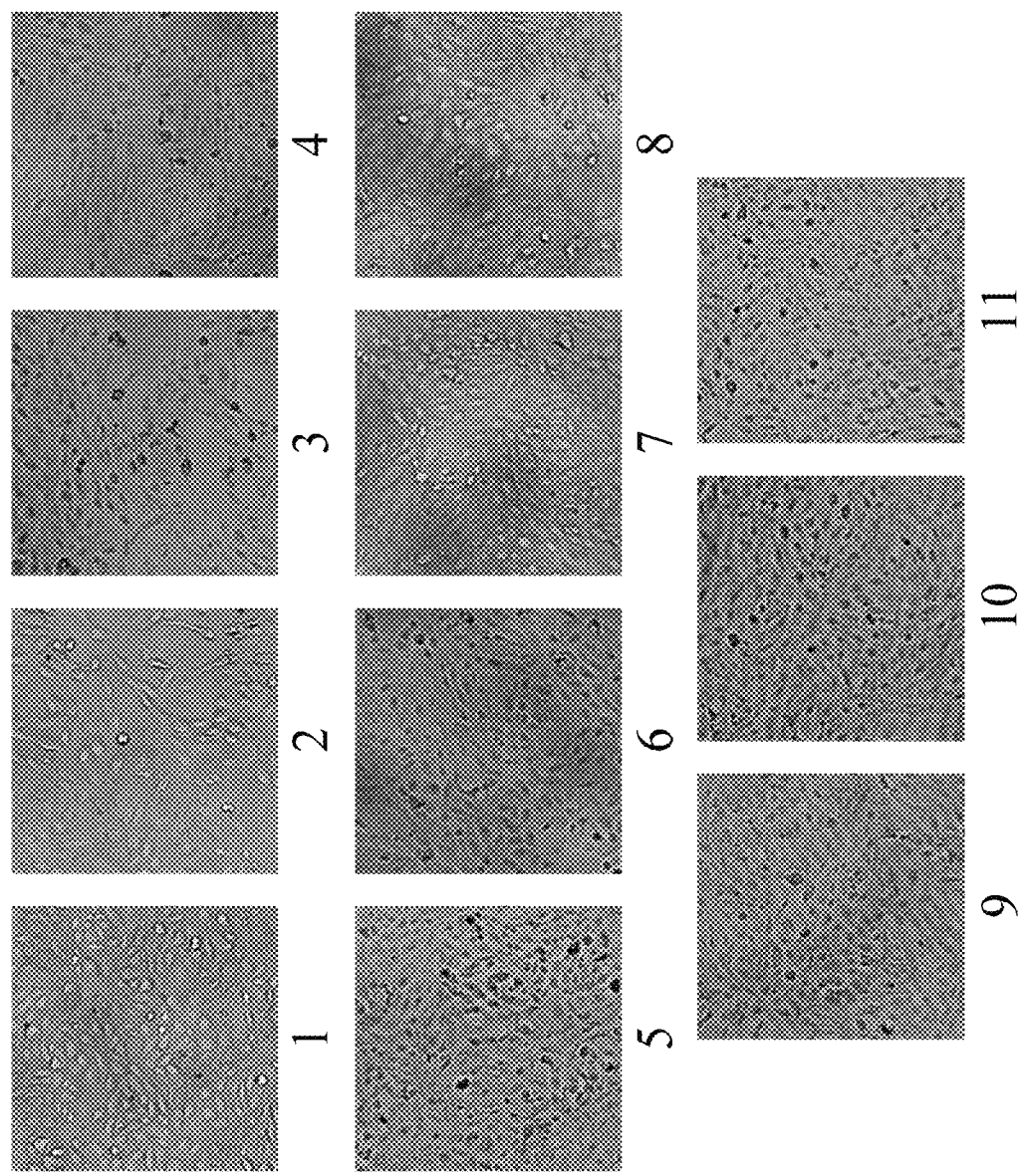
FIG. 33A is a diagram showing that AD and the compound of the disclosure inhibit the TGF-β1-induced conversion of human proximal tubular epithelial cells HK-2 cells to mesenchymal cells (partial photomicrograph; ×100 times), where 1. Control; 2. TGF-β1; 3. TGF-β1+AD (0.63 μM); 4. TGF-β1+T (0.63 μM); 5. TGF-β1+A (0.63 μM); 6.TGF-β1+H (0.08 μM); 7.TGF-β1+F (0.63 μM); 8.TGF-β1+J (0.63 μM); 9. TGF-β1+K (0.63 μM); 10. TGF-β1+z (0.63 μM); 11. TGF-β1+Y (0.16 μM)
Figure 33B:
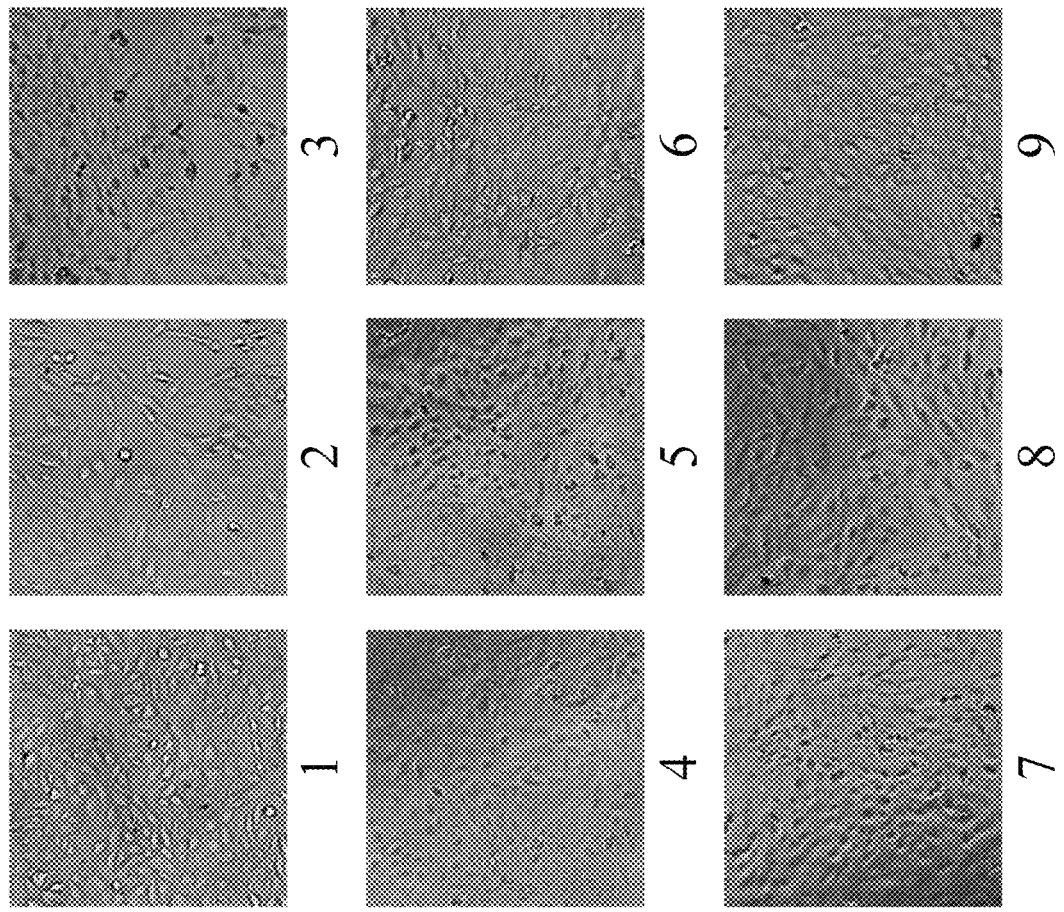
FIG. 33B is a diagram showing that AD and the compound of the disclosure inhibit the TGF-β1-induced conversion of human proximal tubular epithelial cells HK-2 cells to mesenchymal cells (partial photomicrograph; ×100 times), where 1. Control; 2. TGF-β1; 3. TGF-β1+AD (0.63 μM); 4. TGF-β1+d (0.31 μM); 5. TGF-β1+e (0.08 μM); 6. TGF-β1+j (0.31 μM); 7. TGF-β1+h (0.08 μM); 8. TGF-β1+i (0.08 μM); 9. TGF-β1+b (0.31 μM)

The results of Tables 1A and 1B and FIGS. 33A and 33B showed that the compounds of the disclosure can significantly inhibit TGF-β1-induced conversion of human proximal tubular epithelial cells HK-2 to mesenchymal cells at a non-toxic concentration. The inhibition of HK-2 cells to mesenchymal transition was stronger and the safety index was higher compared with AD.

TABLE 1A

Compounds of the disclosure inhibit TGF-β1-induced conversion of human proximal tubular epithelial cells HK-2 to mesenchymal cells

| Compounds | Optimal effective dose range (μM) | Inhibitory effect |
|---|---|---|
| AD | 0.31-1.25 | Medium |
| A | 0.16-1.25 | Strong |
| B | 0.16-1.25 | Strong |
| C | 0.16-1.25 | Strong |
| D | 0.16-1.25 | Strong |
| E | 0.16-1.25 | Strong |
| F | 0.16-1.25 | Strong |
| G | 0.08-0.31 | Extremely strong |
| H | 0.08-0.31 | Extremely strong |
| I | 0.08-0.31 | Extremely strong |
| J | 0.16-1.25 | Strong |
| K | 0.16-1.25 | Strong |
| L | 0.08-0.31 | Extremely strong |
| M | 0.16-1.25 | Strong |
| N | 0.16-1.25 | Strong |
| O | 0.16-1.25 | Strong |
| P | 0.16-1.25 | Strong |
| Q | 0.16-1.25 | Medium |
| R | 0.16-1.25 | Strong |
| S | 0.16-1.25 | Strong |
| T | 0.16-1.25 | Strong |
| U | 0.16-1.25 | Strong |
| V | 0.16-1.25 | Strong |
| W | 0.16-1.25 | Medium |
| X | 0.16-1.25 | Medium |
| Y | 0.08-0.31 | Extremely strong |
| Z | 0.16-1.25 | Strong |

Note:
The test concentrations were 0.08-1.25 μM.

Control: There was an interaction between epithelial cells, and the intercellular linkage was tight, and the cells were arranged in an interlocking fashion like paving stones. Extremely strong (inhibition): the cells are almost the same as the control. No spindle cells are found in the visual field, the intercellular recovery interaction, and the morphology restores its typical paving stone shape. Strong (inhibition): the invasiveness of the cells was inhibited, and the cells were tight, and the cell state was almost completely recovered, and the spindle fibroblasts were rare. Medium (inhibition): the cell density becomes larger and most of the cells were still in a cubic state.

TABLE 1B

Compounds of the disclosure inhibit TGF-β-induced conversion of human proximal tubular epithelial cells HK-2 to mesenchymal cells

| Compounds | Optimal effective dose range (μM) | Inhibitory effect |
|---|---|---|
| AD | 0.31-1.25 | Medium |
| a | 0.16-0.63 | Strong |
| b | 0.16-0.63 | Strong |
| c | 0.31-1.25 | Medium |
| d | 0.16-0.63 | Strong |
| e | 0.08-0.31 | Extremely strong |
| f | 0.16-0.63 | Strong |
| j | 0.31-1.25 | Medium |
| h | 0.08-0.31 | Extremely strong |
| i | 0.16-0.63 | Strong |
| j | 0.16-0.63 | Strong |
| k | 0.31-0.63 | Strong |

Note:
The test concentrations were 0.08-1.25 μM.

Control: There was an interaction between epithelial cells, and the intercellular linkage was tight, and the cells were arranged in an interlocking fashion like paving stones. Extremely strong (inhibition): the cells were almost the same as the control. No spindle cells were found in the visual field, the intercellular recovery interaction, and the morphology restores its typical paving stone shape. Strong (inhibition): the spread of the cells was inhibited, and the cells were tightly arranged; the cell state was completely recovered; the spindle fibroblasts were rare. Medium (inhibition): the cell density becomes larger and most of the cells were still in a cubic state.

Example 13

Compounds of the Disclosure Significantly Reduce the Degree of Renal Fibrosis Induced by Unilateral Ureteral Ligation in SD Rats Unilateral Ureteral Obstruction (UUO) rat model is one of the classic models of renal fibrosis. The model is characterized by accumulation of cellular components in the tubulointerstitial, differentiation/proliferation of fibroblast, an increase of ECM deposition, and tubular atrophy. The modeling method is simple, the modeling success rate is 100%, the lesions are uniform, and the reproducibility is good, which can cause fibrosis in a short period of time. In terms of studying the pathogenesis and mechanism of renal interstitial fibrosis, it is a relatively fast and reliable animal model. Therefore, the UUO model is widely used in the study of the mechanism of renal interstitial fibrosis and the evaluation of the therapeutic effect of improving renal interstitial fibrosis.

1. Materials and Methods

1) Experimental Animals

SPF grade SD rats, healthy, male, body weigh 200±20 g, were purchased from Experimental Animal Center of Henan Province. (License No. SCXK (Yu) 2015-0004).

2) Drugs, Reagents and their Preparation

The source and formulation of andrographolide, sodium carboxymethylcellulose and the test compound were the same as in Example 2.

3) Experimental Method

After SD rats were fed ad libitum for 3 days, they were weighed individually and were randomly divided into six groups including a sham-operated control group, a model group, an AD group (5 mg/kg) and two compound H groups (0.10 mg/kg and 0.15 mg/kg), four rats per group. The preoperative preparation and anesthesia method were the same as in Example 4. After the immobilization in a supine position, the anesthetized rats were prepared. The hair from the lower edge of the sternum to the hind limbs were shaved, and then the surgery cloth was spread out and swabbed with iodine to sterilize the skin regions. An incision with a length of about 2 cm was made about 0.2 cm along the lower edge of the sternum. It was easy to extrude the kidney and then pull ureter upwards to separate from donor abdomen. Double-ligated with 4/0 silk thread and disconnected the ureter with a distance of about ⅓ of the ureter from the bladder. After the kidney was sent back to the abdomen, the 4/0 silk thread continuous suture method was used to close the abdomen layer by layer. The wound was swabbed with iodine and wrapped with sterile gauze. Then the rats rest in a 37° C. warm environment until the animals were fully awake. The sham-operated group only freed the ureter but did not ligature or segment. After 24 h of modeling, the rats were administered by gavage at the same time. The administration method was the same as in Example 2, and the experiment was over after 14 days of administration. The bedding of the rats should be replaced at the first 12 hours of the last gavage, strictly fasting with nothing but water. After administration for 1.5 h, 3% barbital sodium (2 mL/kg) anesthetic were intraperitoneally injected to rats. Following the collection of blood, the left kidney was quickly and completely dissected. The kidney weigh and kidney size were subsequently measured. The kidney of rats was fixed in 4% paraformaldehyde fixative after photographing. Masson's trichrome staining and statistical methods of results were the same as in Example 2, Masson's trichrome staining and relative collagen area results were shown in FIGS. 34 and 35.

2. Experimental Results

Figure 34:
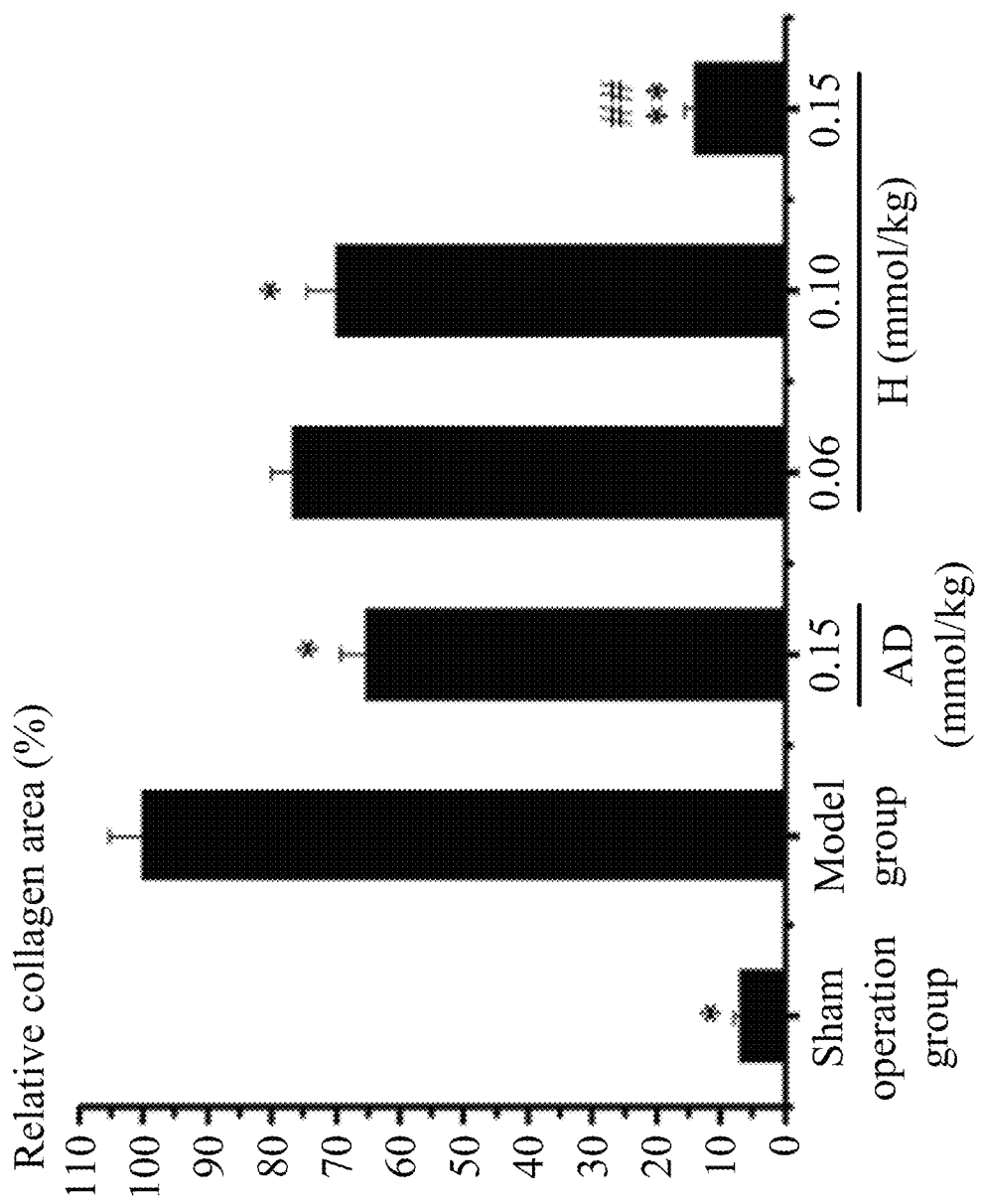
FIG. 34 is a graph showing the effect of representative compound H on the degree of renal fibrosis induced by unilateral ureteral ligation in SD rats (relative collagen area/%); compared with the model group, *P<0.05, **P<0.01; compared with the AD group, ##P<0.01.
Figure 35:
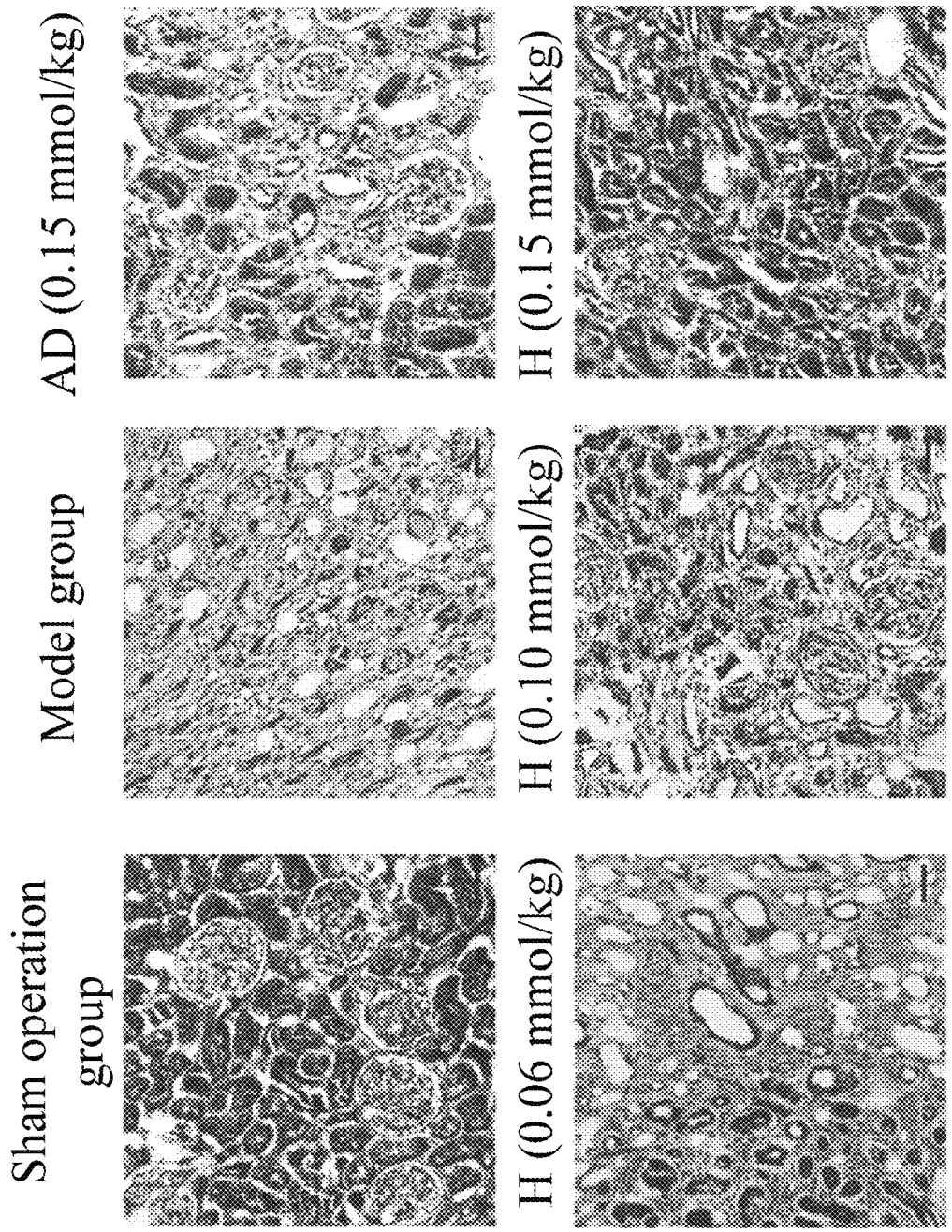
FIG. 35 is a graph showing the effect of representative compound H of the disclosure on the degree of renal fibrosis induced by unilateral ureteral ligation in SD rats (partial tissue of Masson's trichrome staining; ×100 times)
Figure 36:
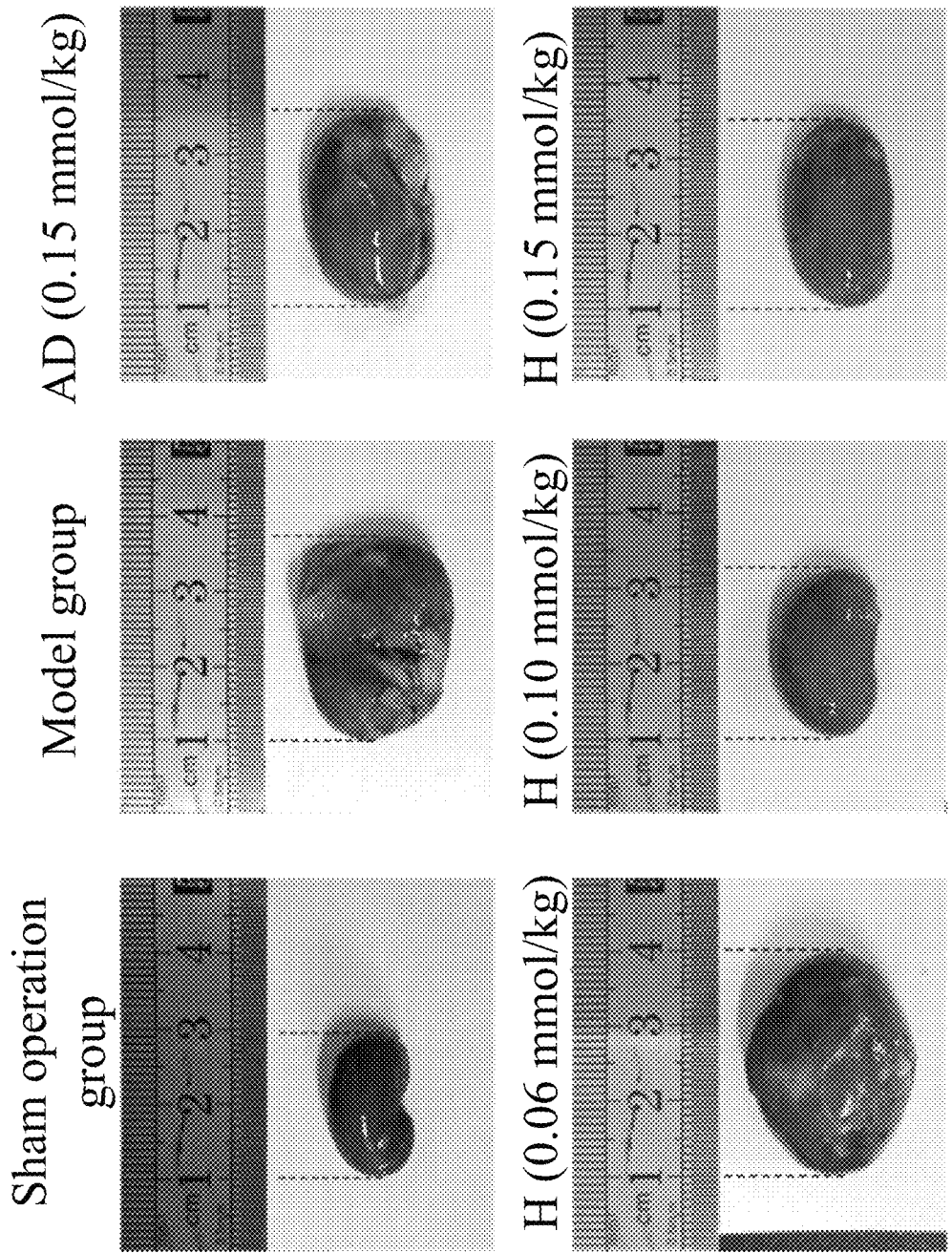
FIG. 36 is a graph showing the effect of compound H of the disclosure on the size of kidney tissue induced by unilateral ureteral ligation in SD rats (partial picture of tissue anatomy of the ligated kidney after administration)
Figure 37:
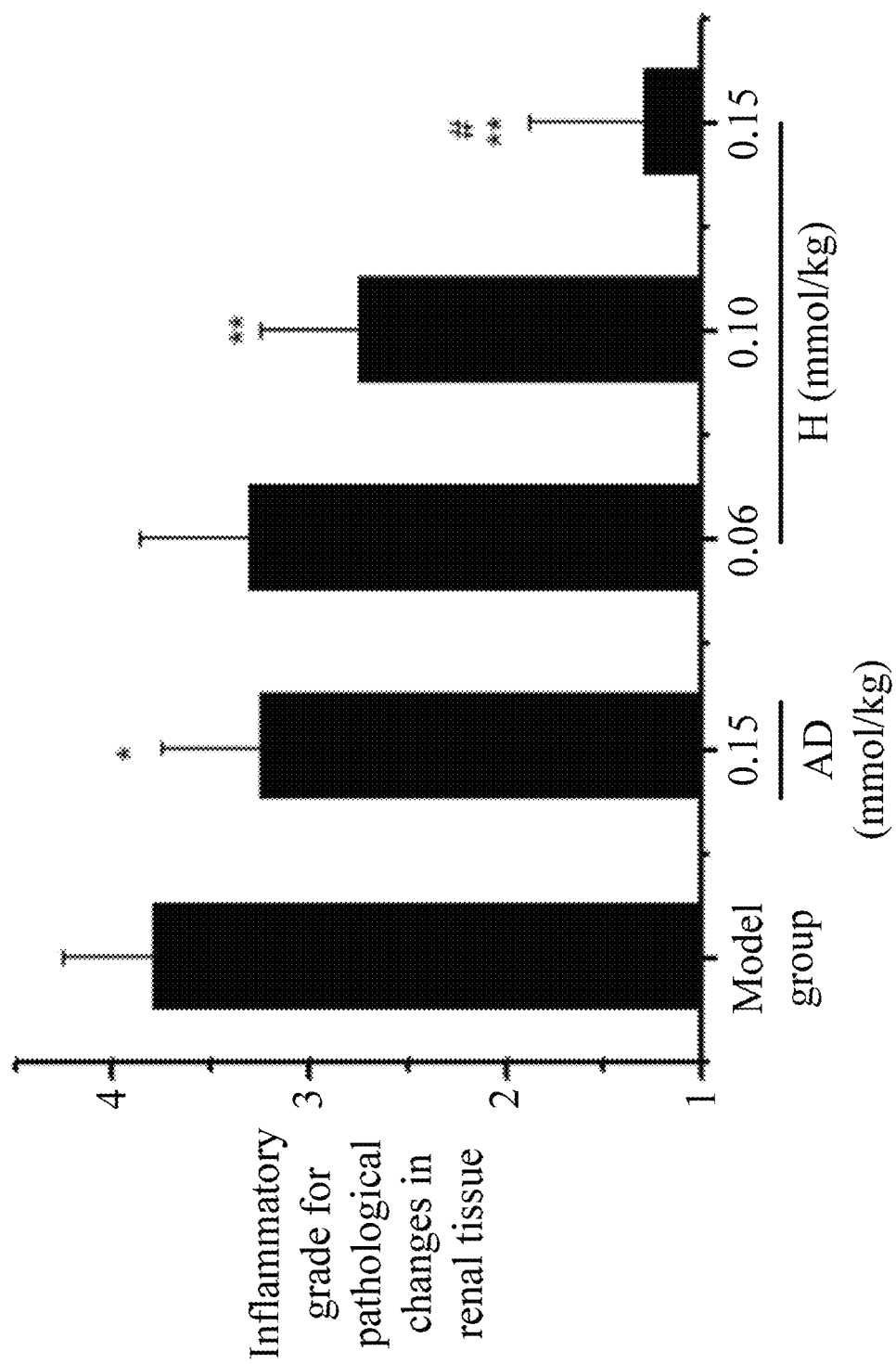
FIG. 37 is a graph showing the effect of representative compound H of the disclosure on the inflammatory grade for pathological changes in renal tissue induced by unilateral ureteral ligation in SD rats (statistical results); compared with the model group, *P<0.05, **P<0.01; compared with the AD group, #P<0.05. Note: The pathological grading criteria for renal interstitial fibrosis: 1=basically normal interstitial, mild tubular degeneration; 2=interstitial fibrosis, tubular atrophy <20%, scattered inflammatory cell infiltration; 3=interstitial fibrosis, tubular atrophy accounted for 30%, scattered and/or diffuse inflammatory cell infiltration; 4=interstitial fibrosis, tubular atrophy >50%, scattered and/or diffuse inflammatory cell infiltration.
Figure 38:
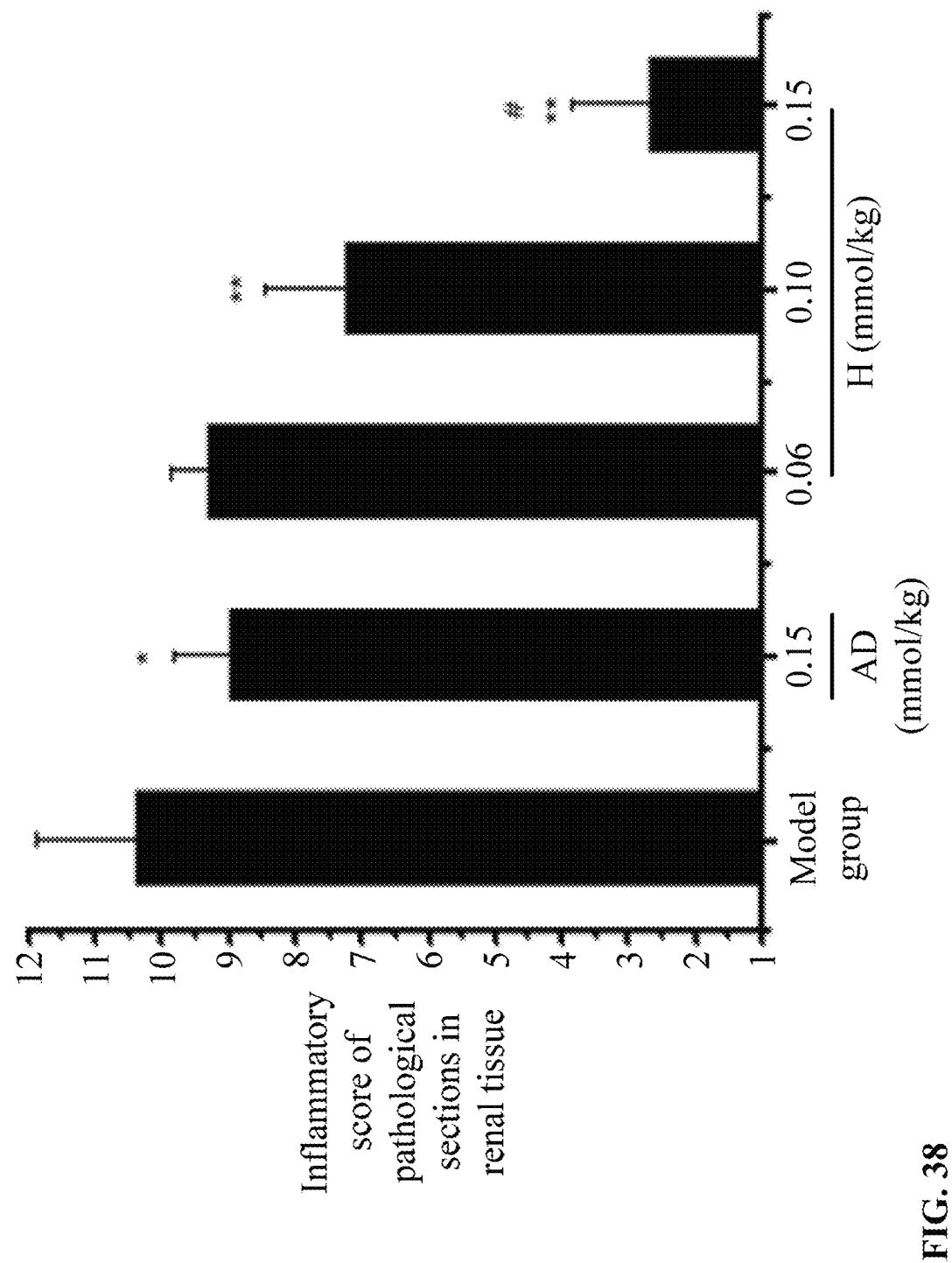
FIG. 38 is a graph showing the effect of compound H on the inflammatory score of pathological sections in renal tissue induced by unilateral ureteral ligation in SD rats (statistical results); compared with the model group, *P<0.05, **P<0.01; compared with the AD group, #P<0.05. Note: Denatured and necrotic tubules are scored as follows: 0=no denaturation or necrosis, 1=mild, 2=moderate, and 3=severe. The overall scores are divided into three grades: 0 (Grade 0); 1-4 (Grade 1); 5-8 (Grade 2); 9-12 (Grade 3)
Figure 39:
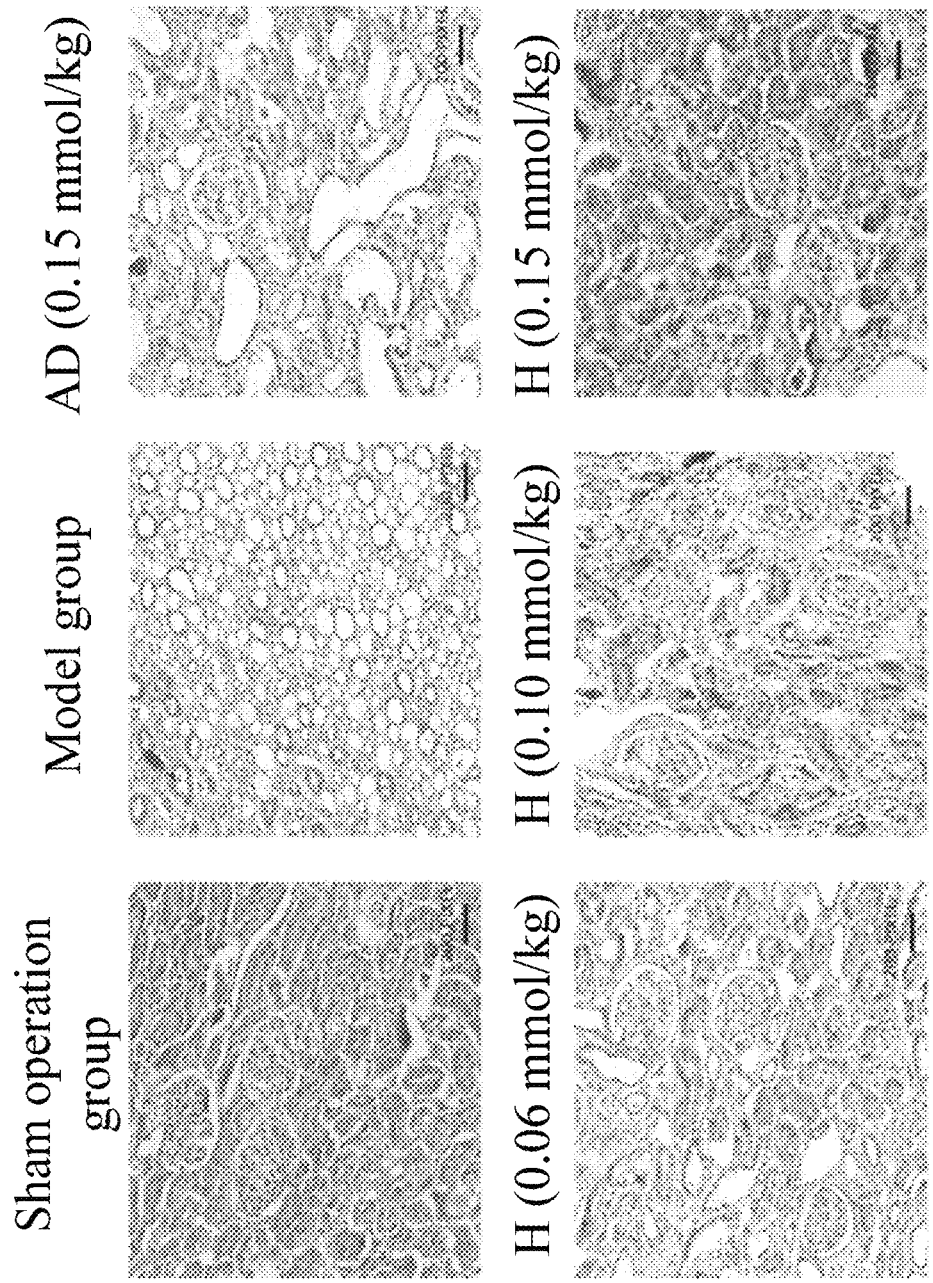
FIG. 39 is a graph showing the effect of compound H on the inflammatory grade for pathological sections in renal tissue induced by unilateral ureteral ligation in SD rats (H&E staining; ×100 times)

The results of FIGS. 34 and 35 showed that on the UUO model, the representative compound H of the disclosure significantly reduced the degree of renal fibrosis, improves the structure of the diseased kidney, and had a significantly stronger effect than AD.

Example 14

The Compounds of the Disclosure Significantly Improve the Inflammatory State of Renal Tissue in Renal Fibrosis of SD Rats Induced by Unilateral Ureteral Ligation 1. Materials and Methods The same as Example 13.

The compound H of the disclosure was selected as a representative, and the improvement of kidney tissue inflammatory state by the compound H of the disclosure was observed by observing anatomical kidney and H&E-stained pathological section. The staining results and pathological scores were shown in FIGS. 36-40. Data were processed and analyzed using SPSS 17.0 statistical software. Data were expressed as mean±standard deviation ($\bar{X}\pm S$); There were significant differences between groups when $P<0.05$.

2. Experimental Results

The results of FIGS. 36, 37, 38, and 39 showed that the sham operation group, the surface of the kidney tissue was moist and shiny, the structure of the glomerulus was intact, the renal tubules were tight and compact, and there was no visible lesion. In the model group, the kidney tissue became swollen, with a large amount of effusion in the middle and adhesion to the surrounding tissues. There was fibroproliferative tissue in the glomerulus and part of the necrosis. The renal interstitial fibrosis material was used to compress the renal tubules. The tubules were severely atrophied and a large number of inflammatory cells infiltrate in the renal interstitium. Compared with the model group, the renal tissue damage of the animals in the drug-administered group was improved to some extent, especially in the high-dose treatment group of the compound H of the disclosure, the surface of the kidney tissue was smooth and moist, non-adhesive, and the kidney was slightly inflated. There was no effusion in the middle, the structure of the glomerulus was basically intact, and the atrophy of the renal tubule was not obvious, and its efficacy was significantly better than that of the AD treatment group.

Example 15

The Compounds of the Disclosure Inhibit Angiotensin II (AngII)-Induced Proliferation of Human Primary Myocardial Fibrosis Cells HCFB Studies have shown that cardiac fibroblasts are the main effector cells of myocardial fibrosis, and they proliferate when stimulated by active substances such as AngII, and their phenotypes are transformed into myofibroblasts that secrete extracellular matrix. Therefore, the cell inhibition of AngII after stimulation of primary cardiac fibroblast HCFB was examined by MTT assay to evaluate the anti-myocardial fibrosis effect of Compound H of the disclosure.

1. Cell Culture and Drug Treatment

Human primary cardiac fibroblast HCFB (provided by Shangcheng Beina Chuanglian Biotech Co., Ltd.) was compared with andrographolide to study the in vitro anti-myocardial fibrosis effect of the compound H of the disclosure. HCFB cells were cultured in H-DMEM medium containing 10% (V/V) fetal bovine serum (GIBCO, USA: Cat. No. 302220F), 100 μg/mL streptomycin, and 100 IU/mL penicillin respectively, and then incubated in an incubator (Binder, Germany) at 5% $CO_2$ and 37° C., humidified atmosphere.

2. MTT Assay for Assessment of Cytotoxicity

HCFB cells in logarithmic growth phase were digested with 0.25% (w/v) trypsin and 0.02% EDTA, and diluted into $5.0\times10^4$/mL cell suspension with H-DMEM medium containing 10% (v/v) fetal bovine serum. After each 96-well plate (Costar, USA) was filled with 200 μL cell suspension, the plates were placed in an incubator at 37° C. and 5% $CO_2$ for 24 h. The medium containing different concentrations of the compound AD or H was added. Following 48 h of incubation, each 96-well plate was added with 20 μL MTT (5 mg/mL) and continued to incubate for 4 h. After the supernatant was discard, 150 μL DMSO was added and shaken for 10 min. The mixture was transferred to each well of an Enzyme-Labeled Instrument. Absorbance at 570 nm was measured and reference absorbance was at 450 nm. The cell survival ratio in each well after compound treatment was calculated, and the survival ratio (%)=A value of treatment group/A value of cell control group×100%, and the results were shown in FIG. 40. Data were processed and analyzed using SPSS 17.0 statistical software.

3. MTT Assay for the Inhibitory Effect of Drugs on the Proliferation of HCFB Stimulated by AngII-Induced Cardiac Fibroblasts HCFB cells in logarithmic growth phase were digested with 0.25% (w/v) trypsin and 0.02% EDTA, and diluted into $5.0\times10^4$/mL cell suspension with H-DMEM medium containing 10% (v/v) fetal bovine serum. After each 96-well plate was filled with 200 μL cell suspension, the plates were placed in an incubator for 24 h in order to generate a single layer of cells. The original medium was discarded, and the cells were washed twice with PBS, and the medium without serum was added. After 24 h of re-synchronized, 200 μL of DMEM-F12 medium containing different concentrations of the test compound and the stimulating factor AngII ($10^{-7}$ mol/L) was added. Each treatment was repeated in 3 wells, furthermore, H-DMEM medium containing 0.5% DMSO was used as a negative control, and H-DMEM medium containing stimulating factor AngII ($10^{-7}$ mol/L) and 0.5% DMSO was used as a positive control. Following 48 h of incubation, the cell survival ratio in each well was calculated, the results were shown in FIG. 41. Data were processed and analyzed using SPSS 17.0 statistical software. Data were expressed as mean±standard deviation ($\overline{X}$±S); There were significant differences between groups when P<0.05.

4. Experimental Results

Figure 40:
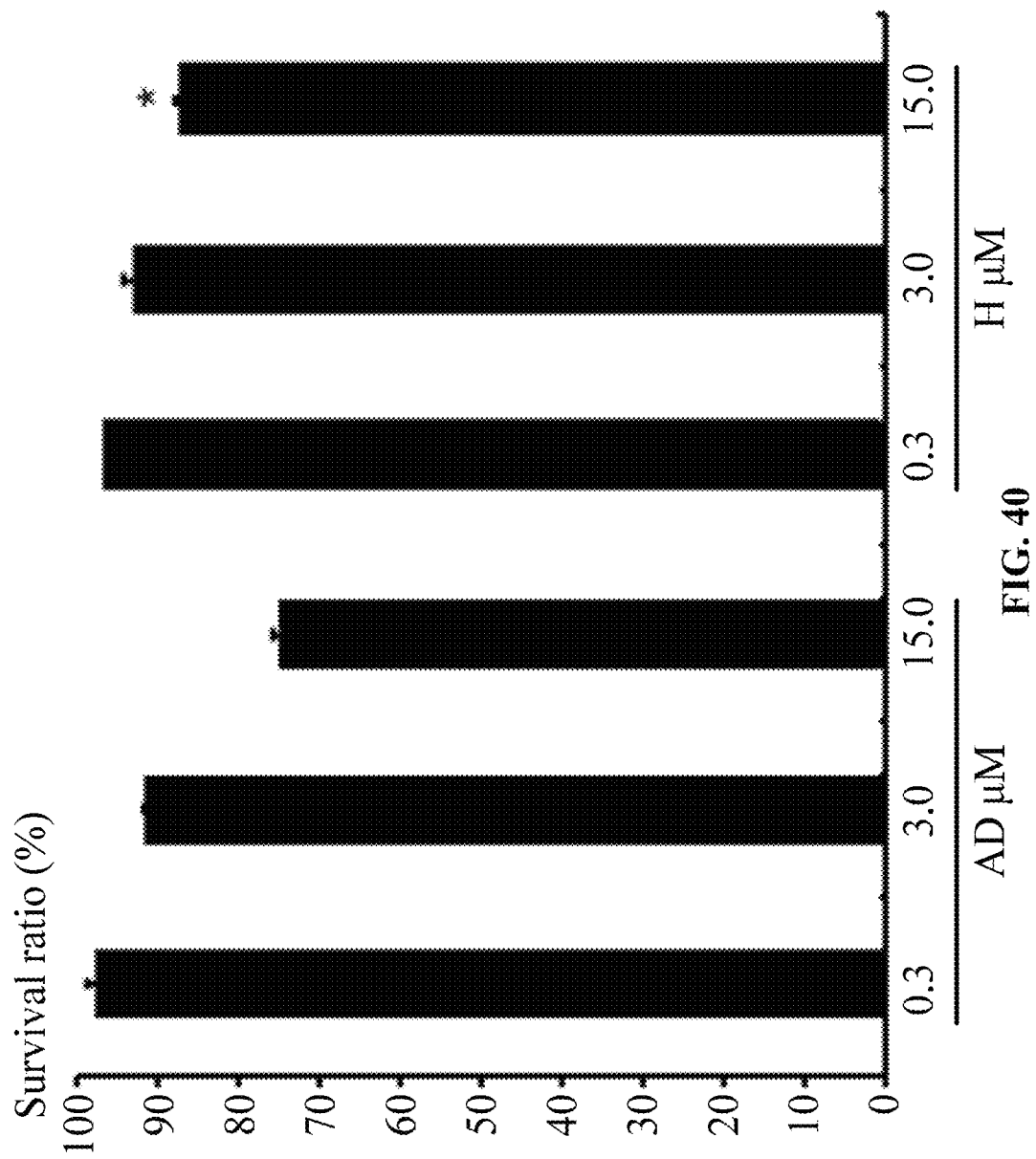
FIG. 40 is a graph showing the effect of AD and the representative compound H (0.3, 3.0 and 15.0 μM) of the disclosure on the proliferation of human primary myocardial fibrosis HCFB cells.
Figure 41:
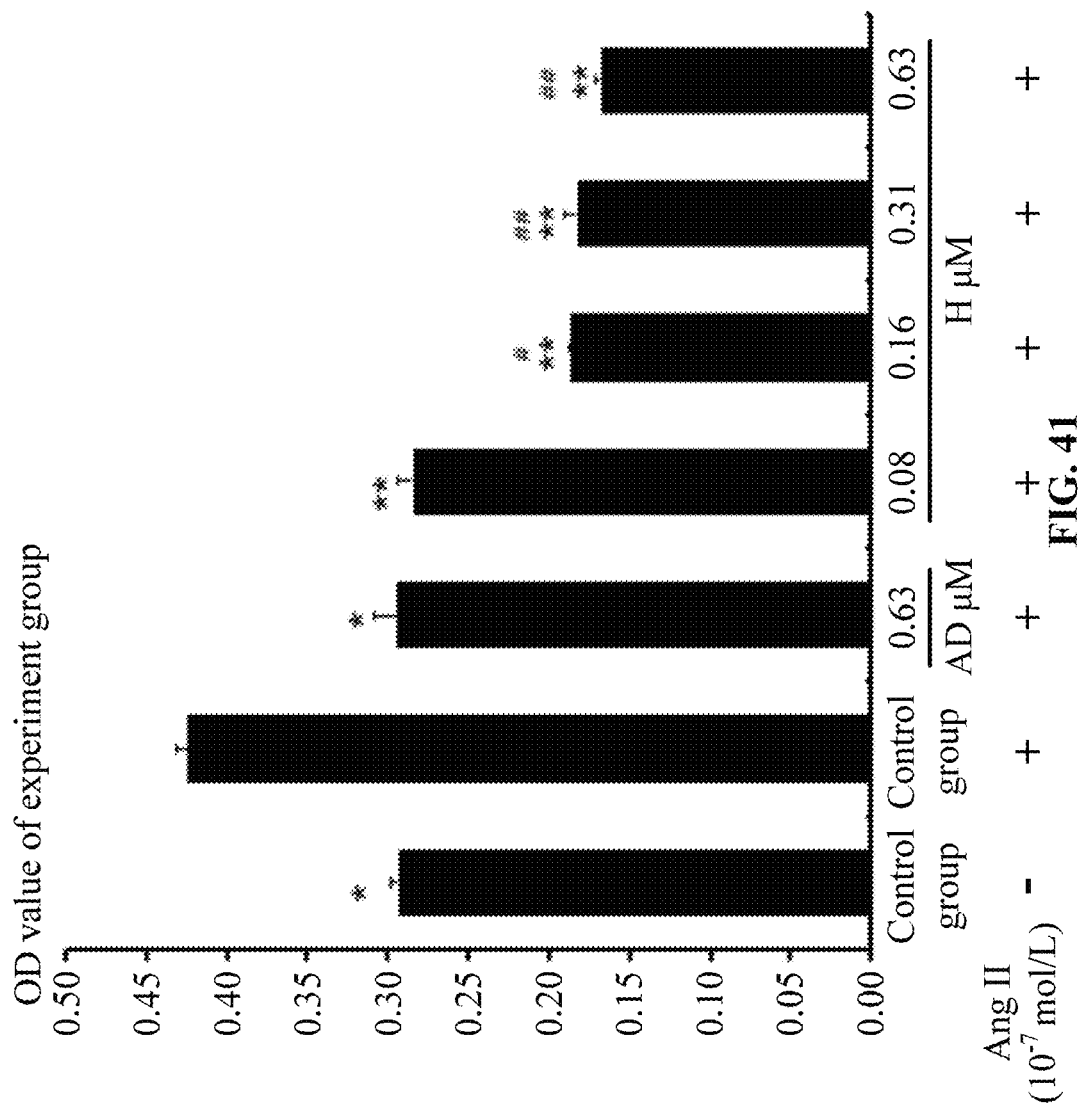
FIG. 41 is a graph showing that AD (0.63 μM) and the representative compound H (0.08 μM, 0.16 μM, 0.31 μM and 0.63 μM) of the disclosure inhibit angiotensin II (Ang II)-induced proliferation of human primary myocardial fibrosis HCFB cells; compared with the AngII group, *P<0.05, **P<0.01; compared with the AD group, #P<0.05, ##P<0.01.

FIG. 40 showed that the compound H of the disclosure showed no significant inhibitory effect on the proliferation of human primary cardiac fibroblast HCFB cells at a concentration of 15.0 μM. FIG. 41 showed that the compound H of the disclosure could significantly inhibit the proliferation of HCFB by AngII at a non-toxic concentration, and had a stronger inhibition effect on human HCFB proliferation and a higher safety index than AD.

It will be obvious to those skilled in the art that changes and modifications may be made, and therefore, the aim in the appended claims is to cover all such changes and modifications.

What is claimed is:

1. A method of treatment of fibrosis of human tissue or organ, the method comprising administering a patient in need thereof a compound of formula (I):

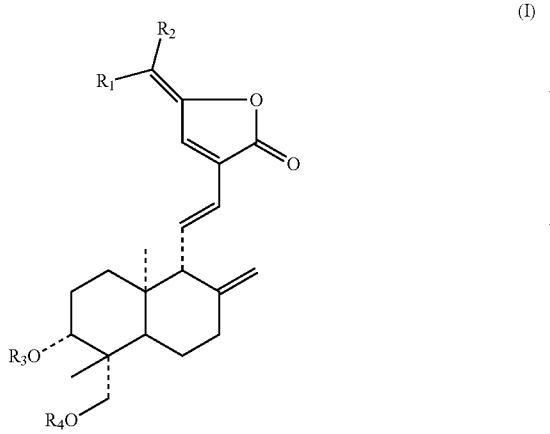

(I)

wherein:
$R_1$, $R_2$ independently, at each occurrence, represent H, a $C_{1-5}$ alkyl, a phenyl, 2-methoxyphenyl, 3-methoxyphenyl, 4-methoxyphenyl, 2,3,5-trimethoxyphenyl, 2-hydroxyphenyl, 3-hydroxyphenyl, 4-hydroxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4-dibromophenyl, 2-chloro-4-fluorophenyl, 2-bromo-4-fluorophenyl, 3-chloro-4-fluorophenyl, 3-bromo-4-fluorophenyl, 2-fluoro-4-bromophenyl, 2-chloro-4-bromophenyl, 3-fluoro-4-bromophenyl, 3-chloro-4-bromophenyl, 2,3,4-trichlorophenyl, 2-methoxy-4-chlorophenyl, 2-hydroxy-4-chlorophenyl, 2-hydroxy-4-methoxyphenyl, 3-amino-4-chlorophenyl, 2-amino-4-chlorophenyl, 2-nitro-4-fluorophenyl, 2-nitro-4-chlorophenyl, a $C_{1-5}$ alkyl substituted phenyl, a halogen and morpholinyl substituted phenyl, a halogen and methylpiperidine substituted phenyl, or N,N-dialkylaminophenyl; or pyridyl, furyl, thienyl, pyrrolyl, indoyl or halogen-substituted pyridyl, furyl, thienyl, pyrrolyl, indoyl; or benzofuranyl, benzimidazolyl, benzothiopyranyl, benzothiazolyl, benzotetrazolyl, benzisoxazolyl, benzisothiazolyl, benzimidazolyl, benzopyrazolyl, benzotriazolyl, benzothienyl, or benzoxazolyl; or $R_1$ and $R_2$ are taken together to form a cyclohexyl;

$R_1$ and $R_2$ are the same or different, but do not synchronously represent H; and $R_3$ and $R_4$ both represent H; or $R_3$ and $R_4$ independently, at each occurrence, represent a methylsulfonyl, a triphenylmethyl, a 3-pyridyl, $CH_2CH_2COOH$, $CH_2CH_2CH_2CH_2COOH$, $CH_2CH_2CH_2CH_2CH_2COOH$, or $CH_2CH_2CH_2CH_2CH_2CH_2CH_2COOH$; or $R_3$ and $R_4$ both represent $COR_5$, and $R_5$ is a 3-pyridyl, $CH_2CH_2COOH$, $CH_2CH_2CH_2CH_2COOH$, $CH_2CH_2CH_2CH_2CH_2COOH$, or $CH_2CH_2CH_2CH_2CH_2CH_2CH_2COOH$.

2. The method of claim 1, wherein:
when one of $R_1$ and $R_2$ is H, the other is selected from a methyl, ethyl or propyl, phenyl, 2-methoxyphenyl, 3-methoxyphenyl, 4-methoxyphenyl, 2-fluorophenyl, 2-chlorophenyl, 2-bromophenyl, 3-fluorophenyl, 3-chlorophenyl, 3-bromophenyl, 4-fluorophenyl, 4-chlorophenyl, 4-bromophenyl, 2-fluoro-3-methoxyphenyl, 3-methoxy-4-chlorophenyl, 2,4-difluorophenyl, 2,4-dichlorophenyl, 2,4-dibromophenyl, 2-fluoro-4-chlorophenyl, 2-bromo-4-chlorophenyl, 3-fluoro-4-chlorophenyl, 3-bromo-4-chlorophenyl, 3,4-difluorophenyl, 3,4-dichlorophenyl, 3,4 dibromophenyl, 2-chloro-4-fluorophenyl, 2-bromo-4-fluorophenyl, 3-chloro-4-fluorobenzene, 3-bromo-4-fluorophenyl, 2-fluoro-4-bromophenyl, 2-chloro-4-bromophenyl, 3-fluoro-4-bromophenyl, 3-chloro-4-bromophenyl, 2-methoxy-4-chlorophenyl, 4-n-propylphenyl, 4-isopropylphenyl, 4-isobutylphenyl, 4-(N,N-dimethylamino)phenyl, 3-fluoro-4-(4-morpholinyl)phenyl, 3-fluoro-4-(4-methylpiperazinyl)phenyl, 2-furyl, 2-pyrrolyl, 6-chloro-3-indolyl, 3-indolyl, 5-chloro-3-indolyl, 6-chloro-2-pyridyl, 3-pyridyl; or $R_1$ and $R_2$ are taken together to form a cyclohexyl; $R_3$ and $R_4$ both represent H; or $R_3$ and $R_4$ independently, at each occurrence, represent $CH_2CH_2COOH$, $CH_2CH_2CH_2CH_2COOH$, $CH_2CH_2CH_2CH_2CH_2COOH$, or $CH_2CH_2CH_2CH_2CH_2CH_2CH_2COOH$; or $R_3$ and $R_4$ both represent $COR_5$, and $R_5$ is a 3-pyridyl or $CH_2CH_2COOH$.

3. The method of claim 1, wherein $R_1$, $R_2$, $R_3$, and $R_4$ of the compound are defined as follows:
i): $R_1$=H, $R_2$=$C_6H_5$, $R_3$=$R_4$=H;
ii): $R_1$=H, $R_2$=2-F—$C_6H_4$, $R_3$=$R_4$=H;
iii): $R_1$=H, $R_2$=2-Cl—$C_6H_4$, $R_3$=$R_4$=H;

iv): $R_1$=H, $R_2$=2-Br—$C_6H_4$, $R_3$=$R_4$=H;
v): $R_1$=H, $R_2$=3-F—$C_6H_4$, $R_3$=$R_4$=H;
vi): $R_1$=H, $R_2$=3-Cl—$C_6H_4$, $R_3$=$R_4$=H;
vii): $R_1$=H, $R_2$=3-Br—$C_6H_4$, $R_3$=$R_4$=H;
viii): $R_1$=H, $R_2$=4-Cl—$C_6H_4$, $R_3$=$R_4$=H;
ix): $R_1$=H, $R_2$=4-F—$C_6H_4$, $R_3$=$R_4$=H;
x): $R_1$=H, $R_2$=4-Br—$C_6H_4$, $R_3$=$R_4$=H;
xi): $R_1$=H, $R_2$=4-$CH_3$O—$C_6H_4$, $R_3$=$R_4$=H;
xii): $R_1$=H, $R_2$=2-$CH_3$O-4-Cl—$C_6H_3$, $R_3$=$R_4$=H;
xiii): $R_2$=H, $R_1$=2-Br—$C_6H_4$, $R_3$=$R_4$=H;
xiv): $R_2$=H, $R_1$=3-Cl—$C_6H_4$, $R_3$=$R_4$=H;
xv): $R_2$=H, $R_1$=2-F-4-Cl—$C_6H_3$, $R_3$=$R_4$=H;
xvi): $R_2$=H, $R_1$=2, 4-diCl—$C_6H_3$, $R_3$=$R_4$=H;
xvii): $R_2$=H, $R_1$=4-F—$C_6H_4$, $R_3$=$R_4$=H;
xvii): $R_2$=H, $R_1$=$C_6H_5$, $R_3$=$R_4$=H;
xix): $R_1$=H, $R_2$=3-F-4-Cl—$C_6H_3$, $R_3$=$R_4$=H;
xx): $R_1$=H, $R_2$=2, 4-diF—$C_6H_3$, $R_3$=$R_4$=H;
xxi): $R_1$=H, $R_2$=3, 4-diCl—$C_6H_3$, $R_3$=$R_4$=H;
xxii): $R_1$=H, $R_2$=4-Cl—$C_6H_4$, $R_3$=$R_4$=$COR_5$, $R_5$=3-pyridyl;
xxiii): $R_1$=H, $R_2$=4-Cl—$C_6H_4$, $R_3$=$R_4$=$CH_2CH_2COOH$;
xxiv): $R_1$=H, $R_2$=4-Cl—$C_6H_4$, $R_3$=$R_4$=$COR_5$, $R_5$=$CH_2CH_2COOH$;
xxv): $R_2$=H, $R_1$=4-Cl—$C_6H_4$, $R_3$=$R_4$=H;
xxvi): $R_2$=H, $R_1$=4-Cl—$C_6H_4$, $R_3$=$R_4$=$COR_5$, $R_5$=3-pyridyl;
xxvii): $R_1$=$CH_3$, $R_2$=$CH_3$, $R_3$=$R_4$=H;
xxviii): 15-cyclohexylidene-14-deoxy-11,12-dehydro-andrographolide; $R_3$=$R_4$=H;
xxix): $R_1$=H, $R_2$=3-F-4-(4-methylpiperazine group)-$C_6H_3$, $R_3$=$R_4$=H;
xxx): $R_1$=H, $R_2$=

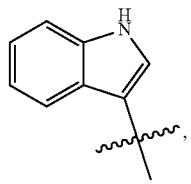 [SMILES: *c1c[nH]c2ccccc12]

$R_3$=$R_4$=H;
xxxi): $R_1$=H, $R_2$=

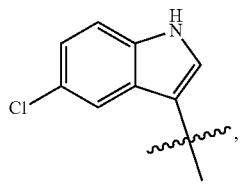 [SMILES: *c1c[nH]c2ccc(Cl)cc12]

$R_3$=$R_4$=H;
xxxii): $R_1$=H, $R_2$=

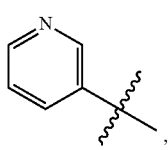

$R_3$=$R_4$=H;
xxxiii): $R_1$=H, $R_2$=

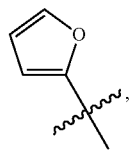

$R_3$=$R_4$=H;
xxxiv): $R_1$=H, $R_2$=

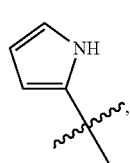

$R_3$=$R_4$=H;
xxxv): $R_1$=H, $R_2$=

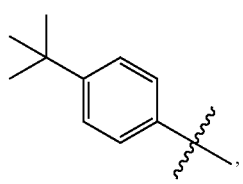 [SMILES: *c1ccc(C(C)(C)C)cc1]

$R_3$=$R_4$=H;
xxxvi): $R_1$=H, $R_2$=

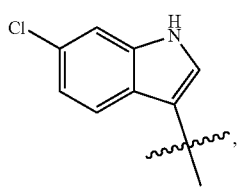

$R_3$=$R_4$=H; or
xxxvii): $R_1$=H, $R_2$=

$R_3$=$R_4$=H.

4. The method of claim 1, wherein the fibrosis of human tissue or organ comprises liver fibrosis, pulmonary fibrosis, renal fibrosis and myocardial fibrosis.

5. The method of claim 2, wherein the fibrosis of human tissue or organ comprises liver fibrosis, pulmonary fibrosis, renal fibrosis and myocardial fibrosis.

6. The method of claim 3, wherein the fibrosis of human tissue or organ comprises liver fibrosis, pulmonary fibrosis, renal fibrosis and myocardial fibrosis.

7. The method of claim 4, wherein the method further comprises mixing the compound with a pharmaceutically acceptable auxiliary to form a product, and formulating the product into an oral preparation or an injection preparation.

8. The method of claim 5, wherein the method further comprises mixing the compound with a pharmaceutically acceptable auxiliary to form a product, and formulating the product into an oral preparation or an injection preparation.

9. The method of claim 6, wherein the method further comprises mixing the compound with a pharmaceutically acceptable auxiliary to form a product, and formulating the product into an oral preparation or an injection preparation.

10. The method of claim 7, wherein the oral preparation is a tablet, a pill, a capsule, a granule or a syrup; the injection preparation is an aqueous injection or a freeze-dried powder injection.

11. The method of claim 8, wherein the oral preparation is a tablet, a pill, a capsule, a granule or a syrup; the injection preparation is an aqueous injection or a freeze-dried powder injection.

12. The method of claim 9, wherein the oral preparation is a tablet, a pill, a capsule, a granule or a syrup; the injection preparation is an aqueous injection or a freeze-dried powder injection.

* * * * *